US009079834B2

(12) United States Patent
Boyd et al.

(10) Patent No.: US 9,079,834 B2
(45) Date of Patent: Jul. 14, 2015

(54) HIV PROTEASE INHIBITORS

(75) Inventors: Michael John Boyd, Winchester, MA (US); Carmela Molinaro, Montreal (CA); Amelie Roy, Saint-Lazare (CA); Vouy-Linh Truong, Pierrefonds (CA)

(73) Assignee: Merck Canada Inc., Kirkland, Quebec (CA)

( * ) Notice: Subject to any disclaimer, the term of this patent is extended or adjusted under 35 U.S.C. 154(b) by 148 days.

(21) Appl. No.: 13/882,267

(22) PCT Filed: Oct. 27, 2011

(86) PCT No.: PCT/CA2011/001202
§ 371 (c)(1),
(2), (4) Date: Oct. 1, 2013

(87) PCT Pub. No.: WO2012/055031
PCT Pub. Date: May 3, 2012

(65) Prior Publication Data
US 2014/0018325 A1    Jan. 16, 2014

Related U.S. Application Data

(60) Provisional application No. 61/407,718, filed on Oct. 28, 2010.

(51) Int. Cl.
| C07C 311/42 | (2006.01) |
|---|---|
| C07D 277/82 | (2006.01) |
| C07D 417/12 | (2006.01) |
| C07C 311/39 | (2006.01) |
| C07C 311/29 | (2006.01) |
| C07C 311/41 | (2006.01) |
| C07D 277/62 | (2006.01) |
| C07D 413/12 | (2006.01) |

(52) U.S. Cl.
CPC ............ *C07C 311/39* (2013.01); *C07C 311/29* (2013.01); *C07C 311/41* (2013.01); *C07D 277/62* (2013.01); *C07D 413/12* (2013.01); *C07D 417/12* (2013.01)

(58) Field of Classification Search
None
See application file for complete search history.

(56) References Cited

U.S. PATENT DOCUMENTS

| 5,196,438 | A | 3/1993 | Martin et al. |
|---|---|---|---|
| 5,413,999 | A | 5/1995 | Vacca et al. |
| 5,484,801 | A | 1/1996 | Al-Razzak et al. |
| 5,484,926 | A | 1/1996 | Dressman et al. |
| 5,585,397 | A | 12/1996 | Tung et al. |
| 7,388,008 | B2 | 6/2008 | Stranix et al. |
| 8,497,383 | B2 | 7/2013 | Coburn et al. |
| 2010/0093811 | A1* | 4/2010 | Coburn et al. ............... 514/357 |
| 2010/0184974 | A1 | 7/2010 | Stranix et al. |

FOREIGN PATENT DOCUMENTS

| WO | WO0138332 A1 | 5/2001 |
|---|---|---|
| WO | WO0168593 A2 | 9/2001 |
| WO | WO0230930 A2 | 4/2002 |
| WO | 02064551 A1 | 8/2002 |
| WO | 03074467 A2 | 9/2003 |
| WO | 2004056764 A1 | 7/2004 |
| WO | 2006012725 A1 | 2/2006 |
| WO | 2006114001 A1 | 11/2006 |
| WO | WO2007062526 A1 | 6/2007 |
| WO | 2008023273 A2 | 2/2008 |
| WO | 2008078200 A2 | 7/2008 |
| WO | 2009042093 A1 | 4/2009 |
| WO | 2009042094 A2 | 4/2009 |
| WO | WO2012055031 A1 | 5/2012 |
| WO | WO2012055034 A1 | 5/2012 |
| WO | WO2013059928 A1 | 5/2013 |

OTHER PUBLICATIONS

Scott M. Hammer, et al, A Controlled Trial Of Two Nucleoside Analogues Plus Indinavir In Persons With Human Immunodeficiency Virus Infection And CD4 Cell Counts Of 200 Per Cubic Millimeter Or Less, The New England Journal of Medicine, 1997, pp. 725-733, vol. 337, No. 11, US.
Amanda C. Durow, et al, Total Synthesis of the Chlorinated, Organic Letters, 2006, pp. 5401-5404, vol. 8, No. 23, US.
C. Richard Nevill, Jr., et al, A Novel Three-step Hydroxy-deamination Sequence: Conversion of Lysine to, Tetrahedron Letters, 1998, pp. 5671-5674, vol. 39, US.
Hiroyuki Toh, et al, Close Structural Resemblance Between Putative Polymerase Of A Drosophila Transposable Genetic Element 17.5 and Pol Gene Product of Moloney Murine Leukaemia Virus, The EMBO Jounral, 1985, pp. 1267-1272, vol. 4, No. 5, US.
Laurence H. Pearl, et al, A Structural Model for the Retroviral Proteases, Nature, 1987, pp. 351-354, vol. 329, US.

(Continued)

*Primary Examiner* — Michael Barker
(74) *Attorney, Agent, or Firm* — Carol S. Quagliato; Laura M. Ginkel

(57) ABSTRACT

Compounds of Formula I are disclosed wherein $R^1$, $R^2$, $R^{3A}$, $R^{3B}$, $R^{4A}$, $R^{4B}$, $R^{5A}$, $R^{5B}$, $R^{6A}$, $R^{6B}$, $R^7$, $R^8$ and $R^9$ are defined herein. The compounds encompassed by Formula I include compounds which are HIV protease inhibitors and other compounds which can be metabolized in vivo to HIV protease inhibitors. The compounds and their pharmaceutically acceptable salts are useful for the prophylaxis or treatment of infection by HIV and the prophylaxis, treatment, or delay in the onset of AIDS. The compounds and their salts can be employed as ingredients in pharmaceutical compositions, optionally in combination with other antivirals, immunomodulators, antibiotics or vaccines.

(I)

20 Claims, No Drawings

(56) References Cited

OTHER PUBLICATIONS

Lee Ratner, et al, Complete Nucleotide Sequence Of AIDS Virus, HTLV-III, Nature, 1985, pp. 277-284, vol. 313, US.

Michael D. Power, et al, Nucleotide Sequence of SRV-1, a Type D Simian, Science, 1986, pp. -1572, vol. 231, US.

Nancy E. Kohl, et al, Active Human Immunodeficiency Virus Protease Is Required For Viral Infectivity, Proc. Natl. Acad. Sci., 1988, pp. 4686-4690, vol. 85, US.

Olugbeminiyi O. Fadeyi, et al, Rapid, General Access to Chiral Beta-Fluoroamines and Beta, Beta-Difluoroamines via Organocatalysis, Organic Letters, 2009, pp. 943-946, vol. 11, No. 4, US.

Roy M. Gulick, et al, Treatment With Indinavir, Zidovudine, and Lamivudine in Adults With Human Immunodeficiency Virus Infection and Prior Antiretroviral Therapy, New England Journal of Medicine, 1997, pp. 734-739, vol. 337, US.

\* cited by examiner

HIV PROTEASE INHIBITORS

CROSS-REFERENCE TO RELATED APPLICATIONS

This application claims the benefit of U.S. provisional application No. 61/407,718 filed on Oct. 28, 2010.

FIELD OF THE INVENTION

The present invention is directed to certain halogen lysinol compounds and their pharmaceutically acceptable salts. Some of these derivatives are compounds which are HIV protease inhibitors. The compounds are useful for the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

A retrovirus designated human immunodeficiency virus (HIV), particularly the strains known as HIV type 1 (HIV-1) virus and type 2 (HIV-2) virus, is the etiological agent of acquired immunodeficiency syndrome (AIDS), a disease characterized by the destruction of the immune system, particularly CD4 T-cells, with attendant susceptibility to opportunistic infections, and its precursor AIDS-related complex ("ARC"), a syndrome characterized by symptoms such as persistent generalized lymphadenopathy, fever and weight loss. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al. (*Proc. Natl Acad Sci.* 85: 4686-4690 (1988)) demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

The HIV genome is made up of single-stranded RNA which comprises several genes that code for structural proteins common to all retroviruses and additional genes that code for accessory proteins specific to HIV (A. D. Frankel and J. A. T. Young, *Annu. Rev. Biochem.* 67:1-25 (1998)). Open reading frames encoding structural proteins include the pol gene (Ratner et al., *Nature* 313: 277-284 (1985)), which encodes reverse transcriptase, integrase and HIV protease, the gag gene, which encodes the core proteins of the virion (Toh et al., *EMBO J* 4: 1267-1272 (1985); Power et al., *Science* 231: 1567-72 (1986); Pearl et al., *Nature* 329: 351-54 (1987)), and the env gene, which encodes gp120 (surface) and gp41 (TM/transmembrane).

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196, 438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitor also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 337: 725-733 (1997) and Gulick et al., *New England J. Med.* 337: 734-739 (1997).

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

References disclosing amino acid derivatives with HIV aspartyl protease inhibiting properties, processes for preparing the derivatives, and/or therapeutic uses of the derivatives include: WO 01/68593, WO 02/064551, WO 03/074467, WO 2004/056764, WO 2006/012725, WO 2006/114001, WO 2007/062526, WO 2008/023273, WO 2008/078200, WO 09/042093, WO 09/042094 and U.S. Pat. No. 7,388,008.

SUMMARY OF THE INVENTION

The present invention is directed to certain halogen lysinol compounds and their use in the inhibition of HIV protease, the prophylaxis of infection by HIV, the treatment of infection by HIV, and the prophylaxis, treatment, and delay in the onset or progression of AIDS. More particularly, the present invention includes compounds of Formula I:

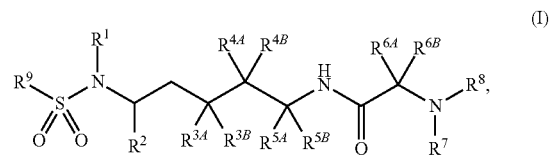

or a pharmaceutically acceptable salt thereof, wherein:
$R^1$ is $C_{1-6}$ alkyl, $C_{1-6}$ fluoroalkyl, CycA, AryA, $C_{1-6}$ alkyl substituted with CycA, HetA, $C_{1-6}$ alkyl substituted with HetA, or $C_{1-6}$-alkyl substituted with AryA;
$R^2$ is C(O)OH, C(O)NH$_2$, C(O)NH—$C_{1-6}$ alkyl, or CH(R$^J$)—Z, wherein:
Z is OH, NH$_2$, or OR$^P$;
$R^J$ is H, $C_{1-6}$ alkyl, $C_{1-6}$ fluoroalkyl, or $C_{1-6}$ alkyl substituted with $C_{3-5}$ cycloalkyl;
$R^P$ is PO(OH)O$^-$.M$^+$; PO(O$^-$)$_2$.2M$^+$; PO(O$^-$)$_2$.M$^{2+}$; or C(O)R$^Q$;
M$^+$ is a pharmaceutically acceptable monovalent counterion;
M$^{2+}$ is a pharmaceutically acceptable divalent counterion; and
R$^Q$ is:
 (1) $C_{1-6}$ alkyl,
 (2) $C_{3-6}$ cycloalkyl,
 (3) $C_{1-6}$ alkyl substituted with $C_{3-6}$ cycloalkyl,
 (4) O—$C_{1-6}$ alkyl,
 (5) O—$C_{1-6}$ alkyl substituted with O—$C_{1-6}$ alkyl, (6) O—$C_{1-6}$ fluoroalkyl,
(7) C(O)O—$C_{1-6}$ alkyl,
(8) C(O)—$C_{1-6}$ alkylene-N(H)—$C_{1-6}$ alkyl,
(9) C(O)—$C_{1-6}$ alkylene-N($C_{1-6}$ alkyl)$_2$,
(10) $C_{1-6}$ alkyl substituted with C(O)O—$C_{1-6}$ alkyl,
(11) $C_{1-6}$ alkyl substituted with C(O)OH,
(12) $C_{1-6}$ alkyl substituted with C(O)—$C_{1-6}$ alkyl,
(13) N(H)—$C_{1-6}$ alkyl,
(14) N(—$C_{1-6}$ alkyl)$_2$,
(15) $C_{1-6}$ alkyl substituted with $NH_2$, N(H)—$C_{1-6}$ alkyl, or N(—$C_{1-6}$ alkyl)$_2$,
(16) AryA,
(17) $C_{1-6}$ alkyl substituted with AryA,
(18) O—$C_{1-6}$ alkyl substituted with AryA,
(19) HetA,
(20) $C_{1-6}$ alkyl substituted with HetA,
(21) O—$C_{1-6}$ alkyl substituted with HetA,
(22) HetB, or
(23) O-HetB;

$R^{3A}$ and $R^{3B}$ are each independently H, Cl, F, $C_{1-6}$ alkyl, $C_{1-6}$ fluoroalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl;

$R^{4A}$ and $R^{4B}$ are each independently H, Cl, F, $C_{1-6}$ alkyl, $C_{1-6}$ fluoroalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl;

$R^{5A}$ and $R^{5B}$ are each independently H, $C_{1-6}$ alkyl, $C_{1-6}$ fluoroalkyl, $C_{1-6}$ alkyl substituted with OH, $C_{2-6}$ alkenyl, $C_{2-6}$ alkynyl, $C_{3-6}$ cycloalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl;

alternatively, $R^{5A}$ and $R^{5B}$ together with the carbon atom to which they are both attached form $C_{3-6}$ cycloalkyl;

and provided that at least one of $R^{3A}$, $R^{3B}$, $R^{4A}$, and $R^{4B}$ is F or Cl;

$R^{6A}$ is:

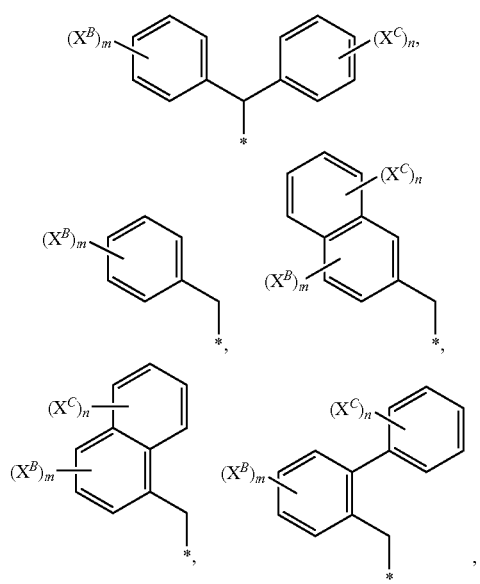

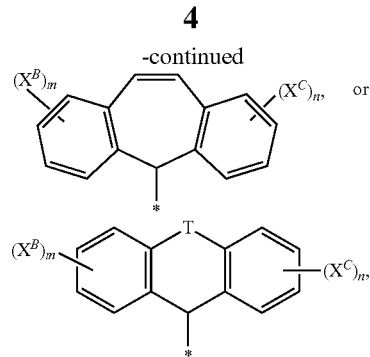

wherein the asterisk (*) denotes the point of attachment to the rest of the compound;

$R^{6B}$ is H or $C_{1-6}$ alkyl;

alternatively, $R^{6A}$ and $R^{6B}$ together with the carbon to which they are attached form a $C_{3-6}$ cycloalkyl which is unsubstituted, or substituted with phenyl, wherein the phenyl is unsubstituted, or substituted with from 1 to $3X^B$.

each $X^B$ and each $X^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) $SO_2H$,
(25) $SO_2$—$C_{1-6}$ alkyl; and
(26) $C_{1-6}$ alkyl substituted with:
 (a) $C_{1-6}$ haloalkyl,
 (b) OH
 (c) O—$C_{1-6}$ alkyl,
 (d) O—$C_{1-6}$ haloalkyl,
 (e) O—$C_{3-6}$ cycloalkyl,
 (f) SH,
 (g) S—$C_{1-6}$ alkyl,
 (h) halo,
 (i) CN,
 (j) $NO_2$,
 (k) $NH_2$,
 (l) N(H)—$C_{1-6}$ alkyl,
 (m) N(—$C_{1-6}$ alkyl)$_2$,
 (n) C(O)—$C_{1-6}$ alkyl,
 (o) C(O)OH,
 (p) C(O)O—$C_{1-6}$ alkyl, or
 (q) $SO_2$—$C_{1-6}$ alkyl;

T is O, S, S(O), or $SO_2$;
m is an integer equal to 0, 1, 2, or 3;
n is an integer equal to 0, 1, 2, or 3;
$R^7$ is H, $C_{1-6}$ alkyl, $C_{3-6}$ cycloalkyl, $C_{1-6}$ alkyl substituted with $C_{3-6}$ cycloalkyl, or C(O)—$R^K$;
$R^8$ is H or $C_{1-6}$ alkyl;
$R^K$ is:
  (1) $C_{1-6}$ alkyl,
  (2) $C_{3-6}$ cycloalkyl,
  (3) $C_{1-6}$ alkyl substituted with $C_{3-6}$ cycloalkyl,
  (4) O—$C_{1-6}$ alkyl,
  (5) O—$C_{1-6}$ alkyl substituted with O—$C_{1-6}$ alkyl,
  (6) O—$C_{1-6}$ fluoroalkyl,
  (7) C(O)O—$C_{1-6}$ alkyl,
  (8) $C_{1-6}$ alkyl substituted with C(O)O—$C_{1-6}$ alkyl,
  (9) $C_{1-6}$ alkyl substituted with C(O)OH,
  (10) $C_{1-6}$ alkyl substituted with C(O)—$C_{1-6}$ alkyl,
  (11) N(H)—$C_{1-6}$ alkyl,
  (12) N(—$C_{1-6}$ alkyl)$_2$,
  (13) $C_{1-6}$ alkyl substituted with $NH_2$, N(H)—$C_{1-6}$ alkyl, or N(—$C_{1-6}$ alkyl)$_2$,
  (14) AryA,
  (15) $C_{1-6}$ alkyl substituted with AryA,
  (16) O—$C_{1-6}$ alkyl substituted with AryA,
  (17) HetA,
  (18) $C_{1-6}$ alkyl substituted with HetA,
  (19) O—$C_{1-6}$ alkyl substituted with HetA,
  (20) HetB,
  (21) O-HetB, or
  (22) O—$C_{1-6}$ alkyl substituted with HetB;
$R^9$ is AryQ or HetQ;
AryQ is an aryl which is independently phenyl or naphthyl, wherein the phenyl or naphthyl is unsubstituted, or substituted with from 1 to 4$X^A$ each of which is independently:
  (1) $C_{1-6}$ alkyl,
  (2) $C_{3-6}$ cycloalkyl,
  (3) $C_{1-6}$ haloalkyl,
  (4) OH
  (5) O—$C_{1-6}$ alkyl,
  (6) O—$C_{1-6}$ haloalkyl,
  (7) O—$C_{3-6}$ cycloalkyl,
  (8) SH,
  (9) S—$C_{1-6}$ alkyl,
  (10) S—$C_{1-6}$ haloalkyl,
  (11) S—$C_{3-6}$ cycloalkyl,
  (12) halo,
  (13) CN,
  (14) $NO_2$,
  (15) $NH_2$,
  (16) N(H)—$C_{1-6}$ alkyl,
  (17) N(—$C_{1-6}$ alkyl)$_2$,
  (18) N(H)C(O)—$C_{1-6}$ alkyl,
  (19) N(H)CH(O),
  (20) CH(O),
  (21) C(O)—$C_{1-6}$ alkyl,
  (22) C(O)OH,
  (23) C(O)O—$C_{1-6}$ alkyl,
  (24) $SO_2$H,
  (25) $SO_2$—$C_{1-6}$ alkyl, or
  (26) $C_{1-6}$ alkyl substituted with:
    (a) $C_{3-6}$ cycloalkyl,
    (b) $C_{1-6}$ haloalkyl,
    (c) OH
    (d) O—$C_{1-6}$ alkyl,
    (e) O—$C_{1-6}$ haloalkyl,
    (f) O—$C_{3-6}$ cycloalkyl,
    (g) SH,
    (h) S—$C_{1-6}$ alkyl,
    (i) S—$C_{1-6}$ haloalkyl,
    (j) S—$C_{3-6}$ cycloalkyl,
    (k) halo,
    (l) CN,
    (m) $NO_2$,
    (n) $NH_2$,
    (o) N(H)—$C_{1-6}$ alkyl,
    (p) N(—$C_{1-6}$ alkyl)$_2$,
    (q) N(H)C(O)—$C_{1-6}$ alkyl,
    (r) N(H)CH(O),
    (s) CH(O),
    (t) C(O)—$C_{1-6}$ alkyl,
    (u) C(O)OH,
    (v) C(O)O—$C_{1-6}$ alkyl,
    (w) $SO_2$H, or
    (x) $SO_2$—$C_{1-6}$ alkyl;
HetQ is a heteroaryl which is independently (i) a 5- or 6-membered heteroaromatic ring containing from 1 to 4 heteroatoms independently selected from N, O and S, wherein each N is optionally in the form of an oxide or (ii) a 9- or 10-membered bicyclic, fused ring system containing from 1 to 4 heteroatoms independently selected from N, O and S, and wherein at least one of the rings is aromatic, each N in a ring is optionally in the form of an oxide, and each S is optionally S(O) or S(O)$_2$; and wherein the heteroaryl is unsubstituted, or substituted with from 1 to 4$X^A$ substituents each of which is independently as set forth in the definition of AryQ.
CycA is a $C_{3-7}$ cycloalkyl which is unsubstituted, or substituted with from 1 to 4 substituents each of which is independently Cl, F, or $C_{1-6}$ alkyl;
each AryA is an aryl which is independently phenyl or naphthyl, wherein the phenyl or naphthyl is unsubstituted, or substituted with from 1 to 4$Y^B$ wherein each $Y^B$ independently has the same definition as $X^B$;
each HetA is a heteroaryl which is independently (i) a 5- or 6-membered heteroaromatic ring containing from 1 to 4 heteroatoms independently selected from N, O and S, or (ii) is a fused, 9- or 10-membered heterobicyclic ring containing from 1 to 4 heteroatoms independently selected from N, O and S, and wherein at least one of the rings is aromatic, each N in a ring is optionally in the form of an oxide, and each S is optionally S(O) or S(O)$_2$; wherein the heteroaromatic ring (i) or the heterobicyclic ring (ii) is unsubstituted, or substituted with from 1 to 4$Y^C$ wherein each $Y^C$ independently has the same definition as $X^B$;
each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is unsubstituted, or substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)$NH_2$, C(O)N(H)—$C_{1-6}$ alkyl, C(O)N(—$C_{1-6}$ alkyl)$_2$, C(O)H, C(O)—$C_{1-6}$ alkyl, $CO_2$H, $CO_2$—$C_{1-6}$ alkyl, $SO_2$H, or $SO_2$—$C_{1-6}$ alkyl.

Other embodiments, aspects and features of the present invention are either further described herein or will be apparent from the ensuing description, examples and appended claims.

DETAILED DESCRIPTION OF THE INVENTION

The present invention includes compounds of Formula I above and pharmaceutically acceptable salts thereof. The compounds encompassed by Formula I include compounds which are HIV protease inhibitors and are useful for the prophylaxis of infection by HIV, the treatment of infection by HIV, and the prophylaxis, treatment, and delay in the onset or progression of AIDS.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

A first embodiment of the invention (Embodiment E1) is a compound of Formula I, or a pharmaceutically acceptable salt thereof, wherein $R^9$ is:
(i) AryQ, wherein AryQ is phenyl which is unsubstituted, or substituted with from 1 to $4X^A$; or
(ii) HetQ, wherein HetQ is a 9- or 10-membered bicyclic, fused ring system which is phenyl with a 5- or 6-membered, saturated or unsaturated heterocycle fused thereto, wherein the heterocycle contains from 1 to 2 heteroatoms independently selected from N, O and S, and wherein the fused ring system is unsubstituted, or substituted with from 1 to $4X^A$, wherein all other variables are as originally defined (i.e. as defined in Formula I in the Summary of the Invention).

A second embodiment of the invention (Embodiment E2) is a compound of Formula I (alternatively referred to as "Compound I"), or a pharmaceutically acceptable salt thereof, wherein $R^1$ is $C_{1-6}$ alkyl, $C_{1-6}$ fluoroalkyl, CycA, AryA, $C_{1-6}$ alkyl substituted with CycA, HetA, $C_{1-6}$ alkyl substituted with HetA, or $C_{1-6}$-alkyl substituted with AryA; and all other variables are as defined in Embodiment E1.

A third embodiment of the invention (Embodiment E3) is a compound of Formula I, or a pharmaceutically acceptable salt thereof, wherein $R^1$ is $C_{1-6}$ alkyl; and all other variables are as defined in Embodiment E1.

A fourth embodiment of the invention (Embodiment E4) is a compound of Formula I, or a pharmaceutically acceptable salt thereof, wherein $R^1$ is $C_{1-6}$ alkyl substituted with CycA, wherein CycA is as defined in the Summary of the Invention; and all other variables are as defined in Embodiment E1.

A fifth embodiment of the invention (Embodiment E5) is a compound of Formula I, or a pharmaceutically acceptable salt thereof, wherein $R^1$ is CycA, wherein CycA is as defined in the Summary of the Invention; and all other variables are as defined in Embodiment E1.

A sixth embodiment of the invention (Embodiment E6) is a compound of Formula I, or a pharmaceutically acceptable salt thereof, wherein $R^1$ is $CH_3$, $CH_2CH_3$, $CH(CH_3)_2$, $CH_2CH_2CH_3$, $CH_2CH_2CH_2CH_3$, $CH_2CH_2CH_2CH_2CH_3$, $CH_2CH(CH_3)_2$, $CH_2CH_2CH(CH_3)_2$, $CH_2CH_2CH_2F$, CycA, $CH_2$-CycA, or $CH_2$-HetA; and all other variables are as defined in Embodiment E1.

A seventh embodiment of the invention (Embodiment E7) is a compound of Formula I, or a pharmaceutically acceptable salt thereof, wherein $R^1$ is $CH_3$, $CH_2CH_3$, $CH(CH_3)_2$, $CH_2CH_2CH_3$, $CH_2CH_2CH_2CH_3$, $CH_2CH_2CH_2CH_2CH_3$, $CH_2CH(CH_3)_2$, $CH_2CH_2CH(CH_3)_2$, $CH_2CH_2CH_2F$, cyclobutyl, cyclohexyl, $CH_2$-cyclopropyl, $CH_2$-cyclobutyl in which the cyclobutyl is substituted with 1 or 2F, or CH2-pyrazolyl in which the pyrazolyl is substituted with 1 or $2CH_3$, and wherein all other variables are as defined in Embodiment E1.

An eighth embodiment of the invention (Embodiment E8) is a compound of Formula I, or a pharmaceutically acceptable salt thereof, wherein $R^1$ is $C_{1-6}$ alkyl, $C_{1-6}$ fluoroalkyl, CycA, $CH_2$-CycA, $CH_2$-AryA or $CH_2$-HetA, and wherein all other variables are as defined in Embodiment E1.

A ninth embodiment of the invention (Embodiment E9) is a compound of Formula I, or a pharmaceutically acceptable salt thereof, wherein $R^1$ is $C_{1-6}$ alkyl substituted with HetA, wherein and all other variables are as defined in Embodiment E1.

A tenth embodiment of the invention (Embodiment E10) is a compound of Formula I, or a pharmaceutically acceptable salt thereof, wherein $R^1$ is $C_{1-6}$ alkyl substituted with AryA, wherein and all other variables are as defined in Embodiment E1.

An eleventh embodiment (Embodiment E11) is a compound of Formula I, or a pharmaceutically acceptable salt thereof, wherein R1 is selected from the group consisting of $C_{1-6}$ alkyl, $C_{1-6}$ fluoroalkyl, $C_{3-6}$ cycloalkyl, or $C_{1-6}$ alkyl substituted with $C_{3-6}$ cycloalkyl and wherein all other variables are as defined in Embodiment E1.

A twelfth embodiment (Embodiment E12) is a compound of Formula I, or a pharmaceutically acceptable salt thereof, wherein R1 is selected from the group consisting of: $CH(CH_3)_2$, $CH_2CH(CH_3)_2$, $CH_2CH_2CH(CH_3)_2$, $CH_2CH_2CH_2CH_3$, $CH_2CH_2CH_2CH_2CH_3$, or

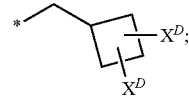

and each $X^D$ is independently H or F and wherein all other variables are as defined in Embodiment E1.

A thirteenth embodiment of the invention (Embodiment E13) is a compound of Formula I, or a pharmaceutically acceptable salt thereof, wherein $R^1$ is as defined in any preceding embodiment, $R^2$ is C(O)OH, C(O)$NH_2$, or CH($R^J$)—Z, C(O)OH or CH($R^J$)—Z, and all other variables are as defined in Embodiment E1.

A fourteenth embodiment of the invention (Embodiment E14) is a compound of Formula I, or a pharmaceutically acceptable salt thereof, wherein $R^1$ is as defined in any preceding embodiment, $R^2$ is C(O)OH, C(O)$NH_2$, $CH_2$—Z, $CH(CH_3)$—Z, $CH(CF_3)$—Z; wherein Z is OH, $NH_2$, or $OR^P$; and wherein $R^P$ is P(O)(OH)$_2$, P(O)(ONa)$_2$, P(O)(OK)$_2$, C(O)—$C_{1-6}$ alkyl, C(O)O—$C_{1-6}$ alkyl, C(O)N(—$C_{1-6}$ alkyl)$_2$, C(O)-pyridyl, or C(O)—$C_{1-6}$ alkylene-$NH_2$, and all other variables are as defined in Embodiment E1.

A fifteenth embodiment of the invention (Embodiment E15) is a compound of Formula I, or a pharmaceutically acceptable salt thereof, wherein $R^1$ is as defined in any preceding embodiment, $R^2$ is $CH_2OH$, C(O)$NH_2$, CH($CH_3$)OH, $CH_2NH_2$, CH($CH_3$)$NH_2$, $CH_2OR^P$, or CH($CH_3$)—$OR^P$; wherein $R^P$ is P(O)(OH)$_2$, P(O)(ONa)$_2$, or C(O)$CH_3$, and all other variables are as defined in Embodiment E1.

A sixteenth embodiment of the invention (Embodiment E16) is a compound of Formula I, or a pharmaceutically acceptable salt thereof, wherein $R^1$ is as defined in any preceding embodiment, $R^2$ is $CH_2OH$, C(O)$NH_2$, CH($CH_3$)OH, or $CH_2NH_2$, and all other variables are as defined in Embodiment E1.

A seventeenth embodiment of the invention (Embodiment E17) is a compound of Formula I, or a pharmaceutically acceptable salt thereof, wherein $R^1$ is as defined in any preceding embodiment, $R^2$ is $CH_2OH$ or C(O)$NH_2$, and all other variables are as defined in Embodiment E1. In some preferred embodiments, $R^2$ is $CH_2OH$.

An eighteenth embodiment of the invention (Embodiment E18) is a compound of Formula I, or a pharmaceutically acceptable salt thereof, wherein $R^1$ is defined in any preceding embodiment, $R^2$ is $CH(R^J)$—Z, and all other variables are as defined in Embodiment E1.

A nineteenth embodiment of the invention (Embodiment E19) is a compound of Formula I, or a pharmaceutically acceptable salt thereof, wherein $R^1$ and $R^2$ are as defined in any preceding embodiment, $R^{3A}$ and $R^{3B}$ are each independently H, Cl, F, $C_{1-6}$ alkyl, $C_{1-6}$ fluoroalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl; with the proviso that at least one of $R^{3A}$, $R^{3B}$, $R^{4A}$, and $R^{4B}$ is F or Cl, and all other variables are as defined in Embodiment E1.

A twentieth embodiment of the invention (Embodiment E20) is a compound of Formula I, or a pharmaceutically acceptable salt thereof, wherein $R^1$ and $R^2$ are as defined in any preceding embodiment, $R^{3A}$ is H, Cl, F, $C_{1-4}$ alkyl, $C_{1-4}$ fluoroalkyl, or $CH_2$—$C_{3-5}$ cycloalkyl, wherein the cycloalkyl is unsubstituted, or substituted with from 1 to 3 substituents each of which is independently F or $C_{1-6}$ alkyl; $R^{3B}$ is H, F, or Cl, and all other variables are as defined in Embodiment E1, with the proviso that at least one of $R^{3A}$, $R^{3B}$, $R^{4A}$, and $R^{4B}$ is F or Cl.

A twenty-first embodiment of the invention (Embodiment E21) is a compound of Formula I, or a pharmaceutically acceptable salt thereof, wherein $R^1$ and $R^2$ are as defined in any preceding embodiment, $R^{3A}$ is H, F, Cl, or $CH_3$; $R^{3B}$ is H, F, or Cl, and all other variables are as defined in Embodiment E1, with the proviso that at least one of $R^{3A}$, $R^{3B}$, $R^{4A}$, and $R^{4B}$ is F or Cl.

A twenty-second embodiment of the invention (Embodiment E22) is a compound of Formula I, or a pharmaceutically acceptable salt thereof, wherein $R^1$ and $R^2$ are as defined in any preceding embodiment, $R^{3A}$ is H, F, or Cl; $R^{3B}$ is H, F, or Cl, and all other variables are as defined in Embodiment E1, with the proviso that at least one of $R^{3A}$, $R^{3B}$, $R^{4A}$, and $R^{4B}$ is F or Cl.

A twenty-third embodiment of the invention (Embodiment E23) is a compound of Formula I, or a pharmaceutically acceptable salt thereof, wherein $R^1$ and $R^2$ are as defined in any preceding embodiment, and wherein the definitions of $R^{3A}$, $R^{3B}$, $R^{4A}$, and $R^{4B}$ are selected from the group consisting of sets (a) to (d) as follows:
(a) $R^{3A}$ is F; $R^{3B}$ is H; $R^{4A}$ is H; and $R^{4B}$ is H;
(b) $R^{3A}$ is F; $R^{3B}$ is F; $R^{4A}$ is H; and $R^{4B}$ is H;
(c) $R^{3A}$ is H; $R^{3B}$ is H; $R^{4A}$ is F; and $R^{4B}$ is H; and
(d) $R^{3A}$ is H; $R^{3B}$ is H; $R^{4A}$ is F; and $R^{4B}$ is F.
and all other variables are as defined in Embodiment E1. In one preferred embodiment, $R^{3A}$ is H; $R^{3B}$ is H, $R^{4A}$ is F, and $R^{4B}$ is F or H.

A twenty-fourth embodiment of the invention (Embodiment E24) is a compound of Formula I, or a pharmaceutically acceptable salt thereof, wherein $R^1$ and $R^2$ are as defined in any preceding embodiment, and wherein the definitions of $R^{3A}$, $R^{3B}$, $R^{4A}$, and $R^{4B}$ are selected from the group consisting of sets (a) to (d) as follows:
(a) $R^{3A}$ is Cl; $R^{3B}$ is H; $R^{4A}$ is H; and $R^{4B}$ is H;
(b) $R^{3A}$ is Cl; $R^{3B}$ is Cl; $R^{4A}$ is H; and $R^{4B}$ is H;
(c) $R^{3A}$ is H; $R^{3B}$ is H; $R^{4A}$ is Cl; and $R^{4B}$ is H; and
(d) $R^{3A}$ is H; $R^{3B}$ is H; $R^{4A}$ is Cl; and $R^{4B}$ is Cl.
and all other variables are as defined in Embodiment E1. In one preferred embodiment, $R^{3A}$ is H; $R^{3B}$ is H, $R^{4A}$ is Cl, and $R^{4B}$ is Cl or H.

A twenty-fifth embodiment of the invention (Embodiment E25) is a compound of Formula I, or a pharmaceutically acceptable salt thereof, wherein $R^1$, $R^2$, $R^{3A}$ and $R^{3B}$ are as defined in any preceding embodiment, $R^{4A}$ and $R^{4B}$ are each independently H, Cl, F, $C_{1-6}$ alkyl, $C_{1-6}$ fluoroalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl, and all other variables are as defined in Embodiment E1, with the proviso that at least one of $R^{3A}$, $R^{3B}$, $R^{4A}$, and $R^{4B}$ is F or Cl.

A twenty-sixth embodiment of the invention (Embodiment E26) is a compound of Formula I, or a pharmaceutically acceptable salt thereof, wherein $R^1$, $R^2$, $R^{3A}$ and $R^{3B}$ are as defined in any preceding embodiment, $R^{4A}$ is H, Cl, F, $C_{1-4}$ alkyl, $C_{1-4}$ fluoroalkyl, or $CH_2$—$C_{3-5}$ cycloalkyl, wherein the cycloalkyl, is unsubstituted, or substituted with from 1 to 3 substituents each of which is independently F or $C_{1-6}$ alkyl; $R^{4B}$ is H, F, or Cl, and all other variables are as defined in Embodiment E1, with the proviso that at least one of $R^{3A}$, $R^{3B}$, $R^{4A}$, and $R^{4B}$ is F or Cl.

A twenty-seventh embodiment of the invention (Embodiment E27) is a compound of Formula I, or a pharmaceutically acceptable salt thereof, wherein $R^1$, $R^2$, $R^{3A}$ and $R^{3B}$ are as defined in any preceding embodiment, $R^{4A}$ is H, F, Cl, or $CH_3$; $R^{4B}$ is H, F, or Cl, and all other variables are as defined in Embodiment E1, with the proviso that at least one of $R^{3A}$, $R^{3B}$, $R^{4A}$, and $R^{4B}$ is F or Cl.

A twenty-eighth embodiment of the invention (Embodiment E28) is a compound of Formula I, or a pharmaceutically acceptable salt thereof, wherein $R^1$, $R^2$, $R^{3A}$, $R^{3B}$, $R^{4A}$ and $R^{4B}$ are as defined in any preceding embodiment, $R^{5A}$ and $R^{5B}$ are each independently H, $C_{1-6}$ alkyl, $C_{1-6}$ fluoroalkyl, $C_{1-6}$ alkyl substituted with OH, $C_{2-6}$ alkenyl, $C_{2-6}$ alkynyl, $C_{3-6}$ cycloalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl; and all other variables are as defined in Embodiment E1.

A twenty-ninth embodiment of the invention (Embodiment E29) is a compound of Formula I, or a pharmaceutically acceptable salt thereof, wherein $R^1$, $R^2$, $R^{3A}$, $R^{3B}$, $R^{4A}$ and $R^{4B}$ are as defined in any preceding embodiment, $R^{5A}$ and $R^{5B}$ together with the carbon atom to which they are both attached form $C_{3-6}$ cycloalkyl; and all other variables are as defined in Embodiment E1.

A thirtieth embodiment of the invention (Embodiment E30) is a compound of Formula I, or a pharmaceutically acceptable salt thereof, wherein $R^1$, $R^2$, $R^{3A}$, $R^{3B}$, $R^{4A}$ and $R^{4B}$ are as defined in any preceding embodiment, $R^{5A}$ is H, $C_{1-4}$ alkyl, $C_{1-4}$ fluoroalkyl, or $CH_2$—$C_{3-5}$ cycloalkyl, wherein the cycloalkyl, is unsubstituted, or substituted with from 1 to 3 substituents each of which is independently F or $C_{1-6}$ alkyl; $R^{5B}$ is H or $C_{1-6}$ alkyl; and all other variables are as defined in Embodiment E1.

A thirty-first embodiment of the invention (Embodiment E31) is a compound of Formula I, or a pharmaceutically acceptable salt thereof, wherein $R^1$, $R^2$, $R^{3A}$, $R^{3B}$, $R^{4A}$ and $R^{4B}$ are as defined in any preceding embodiment, $R^{5A}$ and $R^{5B}$ are H; and all other variables are as defined in Embodiment E1.

A thirty-second embodiment of the invention (Embodiment E32) is a compound of Formula I, or a pharmaceutically acceptable salt thereof, wherein $R^1$, $R^2$, $R^{3A}$, $R^{3B}$, $R^{4A}$, $R^{4B}$, $R^{5A}$ and $R^{5B}$ are as defined in any preceding embodiment; $R^{6A}$ is selected from the group consisting of:

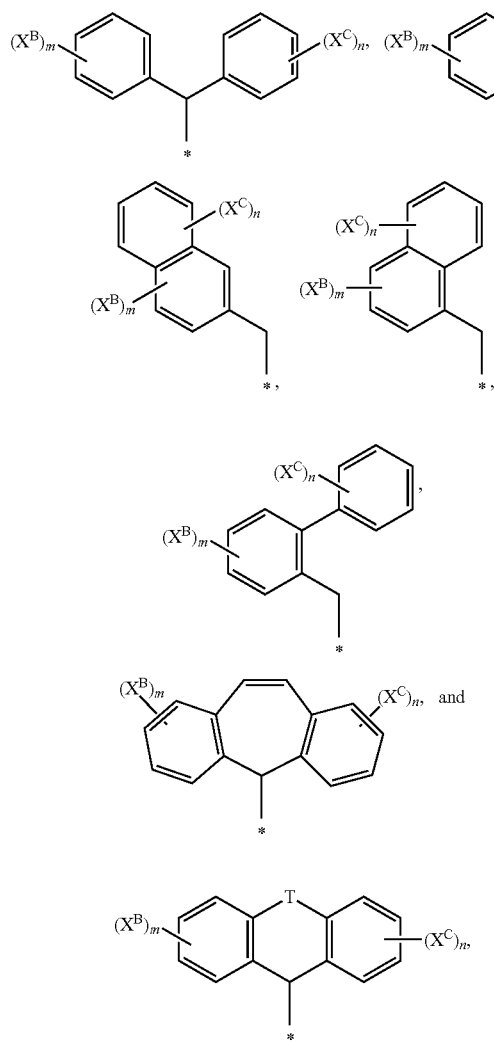

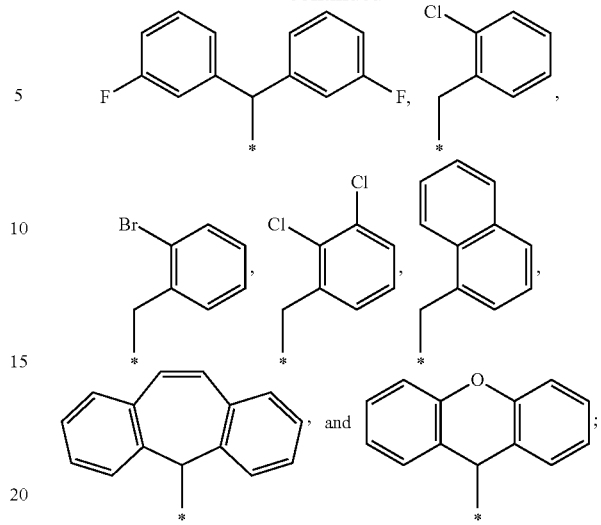

wherein the asterisk (*) denotes the point of attachment to the rest of the compound;

$R^{6B}$ is H or $C_{1-6}$ alkyl; and all other variables are as defined in Embodiment E1.

A thirty-third embodiment of the invention (Embodiment E33) is a compound of Formula I, or a pharmaceutically acceptable salt thereof, wherein $R^1$, $R^2$, $R^{3A}$, $R^{3B}$, $R^{4A}$, $R^{4B}$, $R^{5A}$ and $R^{5B}$ are as defined in any preceding embodiment; $R^{6A}$ is selected from the group consisting of:

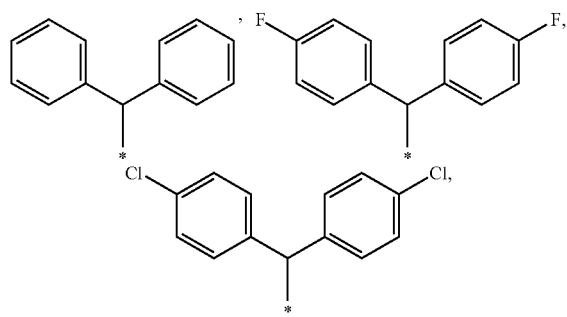

and all other variables are as defined in Embodiment E1.

A thirty-fourth embodiment of the invention (Embodiment E34) is a compound of Formula I, or a pharmaceutically acceptable salt thereof, wherein $R^1$, $R^2$, $R^{3A}$, $R^{3B}$, $R^{4A}$, $R^{4B}$, $R^{5A}$ and $R^{5B}$ are as defined in any preceding embodiment; $R^{6A}$ is:

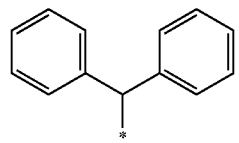 [SMILES: *C(c1ccccc1)c1ccccc1]

$R^{6B}$ is H, and all other variables are as defined in Embodiment E1.

A thirty-fifth embodiment of the invention (Embodiment E35) is a compound of Formula I, or a pharmaceutically acceptable salt thereof wherein $R^1$, $R^2$, $R^{3A}$, $R^{3B}$, $R^{4A}$, $R^{4B}$, $R^{5A}$ and $R^{5B}$ are as defined in any preceding embodiment; $R^{6A}$ and $R^{6B}$ together with the carbon to which they are attached form a $C_{3-6}$ cycloalkyl which is unsubstituted, or substituted with phenyl, wherein the phenyl is unsubstituted, or substituted with from 1 to 3 $X^B$, and all other variables are as defined in Embodiment E1.

A thirty-sixth embodiment of the invention (Embodiment E36) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$ and $R^{6B}$ are as defined in any preceding embodiment, $R^7$ is H, $C_{1-6}$ alkyl, $C_{3-6}$ cycloalkyl, $C_{1-6}$ alkyl substituted with $C_{3-6}$ cycloalkyl, or C(O)—$R^K$ and all other variables are as defined in Embodiment E1.

A thirty-seventh embodiment of the invention (Embodiment E37) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$ and $R^{6B}$ are as defined in any preceding embodiment, $R^7$ is H, $C_{1-6}$ alkyl, C(O)—$C_{1-6}$ alkyl, C(O)O—$C_{1-6}$ alkyl, C(O)N(—$C_{1-6}$ alkyl)$_2$, C(O)-HetA, C(O)OCH$_2$-HetA, C(O)-HetB, or C(O)OCH$_2$-HetB, and all other variables are as defined in Embodiment E1.

A thirty-eighth embodiment of the invention (Embodiment E38) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$ and $R^{6B}$ are as defined in any preceding embodiment, $R^7$ is H, $CH_3$, $C(O)CH_3$, $C(O)OCH_3$, $C(O)OC(CH_3)_3$, $C(O)N(CH_3)_2$, C(O)-morpholinyl, C(O)-pyridyl, or $C(O)O$—$CH_2$-pyridyl, and all other variables are as defined in Embodiment E1.

A thirty-ninth embodiment of the invention (Embodiment E39) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$ and $R^{6B}$ are as defined in any preceding embodiment, $R^7$ is $C(O)OCH_3$, and all other variables are as defined in Embodiment E1.

A fortieth embodiment of the invention (Embodiment E40) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$ and $R^7$ are as defined in any preceding embodiment, $R^8$ is H or $C_{1-6}$ alkyl, and all other variables are as defined in Embodiment E1.

A forty-first embodiment of the invention (Embodiment E41) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$ and $R^7$ are as defined in any preceding embodiment, $R^8$ is H or $C_{1-4}$ alkyl, and all other variables are as defined in Embodiment E1.

A forty-second embodiment of the invention (Embodiment E42) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$ and $R^7$ are as defined in any preceding embodiment, $R^8$ is H or $CH_3$, and all other variables are as defined in Embodiment E1.

A forty-third embodiment of the invention (Embodiment E43) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$ and $R^7$ are as defined in any preceding embodiment, $R^8$ is H, and all other variables are as defined in Embodiment E1.

A forty-fourth embodiment of the invention (Embodiment E44) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$, $R^7$ and $R^8$ are as defined in any preceding embodiment, $R^9$ is AryQ or HetQ, and all other variables are as originally defined.

A forty-fifth embodiment of the invention (Embodiment E45) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$, $R^7$ and $R^8$ are as defined in any preceding embodiment, $R^9$ is phenyl or benzothiazolyl, either of which is unsubstituted, or substituted with 1 or $2X^A$, wherein each $X^A$ is independently selected from the group consisting of: (1) $C_{1-3}$ alkyl, (2) cyclopropyl, (3) $CF_3$, (4) OH, (5) O—$C_{1-3}$ alkyl, (6) $OCF_3$, (7) Cl, (8) Br, (9) F, (10) CN, (11) $NO_2$, (12) $NH_2$, (13) N(H)—$C_{1-3}$ alkyl, (14) N(—$C_{1-3}$ alkyl)$_2$, (15) C(O)—$C_{1-3}$ alkyl, (16) $CO_2H$, (17) C(O)O—$C_{1-3}$ alkyl, and (18) $C_{1-3}$ alkyl substituted with (a) cyclopropyl, (b) $CF_3$, (c) OH, (d) O—$C_{1-3}$ alkyl, (e) $OCF_3$, (f) Cl, (g) Br, (h) F, (i) CN, (j) $NO_2$, (k) $NH_2$, (l) N(H)—$C_{1-3}$ alkyl, (m) N(—$C_{1-3}$ alkyl)$_2$, (n) C(O)—$C_{1-3}$ alkyl, (o) $CO_2H$, or (p) C(O)O—$C_{1-3}$ alkyl; and all other variables are as originally defined.

A forty-sixth embodiment of the invention (Embodiment E46) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$, $R^7$ and $R^8$ are as defined in any preceding embodiment, $R^9$ is phenyl or benzothiaolyl, wherein the benzothioazolyl is unsubstituted and the phenyl is unsubstituted, or substituted with 1 or 2 $X^A$, wherein each $X^A$ is independently selected from the group consisting of: (1) $CH_3$, (2) $CH_2CH_3$, (3) $CF_3$, (4) OH, (5) $OCH_3$, (6) $OCF_3$, (7) Cl, (8) Br, (9) F, (10) CN, (11) $NH_2$, (12) N(H)$CH_3$, (13) N($CH_3$)$_2$, (14) C(O)$CH_3$, (15) C(O)O$CH_3$, (16) $CH_2OH$, (17) $CH_2OCH_3$, (18) $CH_2NH_2$, (19) $CH_2N(H)CH_3$, (20) $CH_2N(CH_3)_2$, (21) CH($CH_3$)OH, (22) CH($CH_3$)$OCH_3$, (23) CH($CH_3$)$NH_2$, (24) CH($CH_3$)N(H)$CH_3$, or (25) CH($CH_3$)N($CH_3$)$_2$; and all other variables are as originally defined.

A forty-seventh embodiment of the invention (Embodiment E47) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$, $R^7$ and $R^8$ are as defined in any preceding embodiment, $R^9$ is:

(i) phenyl substituted with 1 or $2X^A$, wherein one $X^A$ is in the para position on the phenyl ring and is $CH_3$, Cl, Br, F, $NH_2$, C(O)$CH_3$, $CH_2OH$, or CH($CH_3$)OH; and the other, optional $X^A$ is in the meta position on the phenyl ring and is Cl, Br, or F; or (ii)

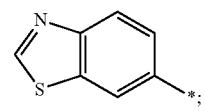

wherein the asterisk (*) denotes the point of attachment to the rest of the compound, and all other variables are as originally defined.

A forty-eighth embodiment of the invention (Embodiment E48) is a compound of Formula I, or a pharmaceutically acceptable salt thereof, wherein $R^1$, $R^2$, $R^{3A}$, $R^{3B}$, $R^{4A}$, $R^{4B}$, $R^{5A}$, $R^{5B}$; $R^{6A}$, $R^{6B}$, $R^7$ and $R^8$ are as defined in any preceding embodiment, $R^9$ is:

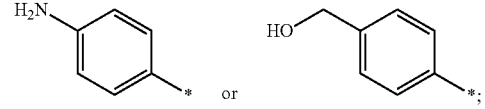

wherein the asterisk (*) denotes the point of attachment to the rest of the compound, and all other variables are as originally defined.

In alternative embodiments of Embodiment E2 through Embodiment E32, each $X^B$ and each $X^C$ are independently selected from the group consisting of:
(1) $C_{1-3}$ alkyl,
(2) cyclopropyl,
(3) $CF_3$,
(4) OH,
(5) O—$C_{1-3}$ alkyl,
(6) $OCF_3$,
(7) Cl,
(8) Br;
(9) F,
(10) CN,
(11) $NO_2$,
(12) $NH_2$,
(13) N(H)—$C_{1-3}$ alkyl,
(14) N(—$C_{1-3}$ alkyl)$_2$,
(15) C(O)—$C_{1-3}$ alkyl,
(16) $CO_2H$,
(17) C(O)O—$C_{1-3}$ alkyl,
(18) $CH_2OH$, and
(19) $CH_2O$—$C_{1-3}$ alkyl; and all other variables are as defined in the original Embodiments E2 through E32.

In further alternative embodiments of Embodiment E2 through Embodiment E32, each $X^B$ and each $X^C$ are independently selected from the group consisting of:

(1) CH$_3$,
(2) CH$_2$CH$_3$,
(3) CF$_3$,
(4) OH,
(5) OCH$_3$,
(6) OCF$_3$,
(7) Cl,
(8) Br,
(9) F,
(10) CN,
(11) NH$_2$,
(12) N(H)CH$_3$,
(13) N(CH$_3$)$_2$,
(14) C(O)CH$_3$,
(15) C(O)OCH$_3$,
(16) CH$_2$OH, and
(17) CH$_2$OCH$_3$; and all other variables are as defined in the original Embodiments E2 through E32.

In additional embodiments of Embodiment E1 through Embodiment E44, $X^A$ is defined as: (1) C$_{1-3}$ alkyl, (2) cyclopropyl, (3) CF$_3$, (4) OH, (5) O—C$_{1-3}$ alkyl, (6) OCF$_3$, (7) Cl, (8) Br, (9) F, (10) CN, (11) NO$_2$, (12) NH$_2$, (13) N(H)—C$_{1-3}$ alkyl, (14) N(—C$_{1-3}$ alkyl)$_2$, (15) C(O)—C$_{1-3}$ alkyl, (16) CO$_2$H, (17) C(O)O—C$_{1-3}$ alkyl, or (18) C$_{1-3}$ alkyl substituted with (a) cyclopropyl, (b) CF$_3$, (c) OH, (d) O—C$_{1-3}$ alkyl, (e) OCF$_3$, (f) Cl, (g) Br, (h) F, (i) CN, (j) NO$_2$, (k) NH$_2$, (l) N(H)—C$_{1-3}$ alkyl, (m) N(—C$_{1-3}$ alkyl)$_2$, (n) C(O)—C$_{1-3}$ alkyl, (o) CO$_2$H, or (p) C(O)O—C$_{1-3}$ alkyl; and all other variables are as defined in original Embodiments E1 through E44.

In further additional embodiments of Embodiment E1 through Embodiment E44, $X^A$ is defined as: (1) CH$_3$, (2) CH$_2$CH$_3$, (3) CF$_3$, (4) OH, (5) OCH$_3$, (6) OCF$_3$, (7) Cl, (8) Br, (9) F, (10) CN, (11) NH$_2$, (12) N(H)CH$_3$, (13) N(CH$_3$)$_2$, (14) C(O)CH$_3$, (15) C(O)OCH$_3$, (16) CH$_2$OH, (17) CH$_2$OCH$_3$, (18) CH$_2$NH$_2$, (19) CH$_2$N(H)CH$_3$, (20) CH$_2$N(CH$_3$)$_2$, (21) CH(CH$_3$)OH, (22) CH(CH$_3$)OCH$_3$, (23) CH(CH$_3$)NH$_2$, (24) CH(CH$_3$)N(H)CH$_3$, or (25) CH(CH$_3$)N(CH$_3$)$_2$; and all other variables are as defined in original Embodiments E1 through E44.

In still further additional embodiments of Embodiment E1 through Embodiment E44, $X^A$ is defined as: (1) NH$_2$, C(O)CH$_3$, CH$_2$OH, or CH(CH$_3$)OH; and all other variables are as defined in original Embodiments E1 through E44.

One class of compounds of the present invention (alternatively referred to as Class C1) includes compounds of Formula II:

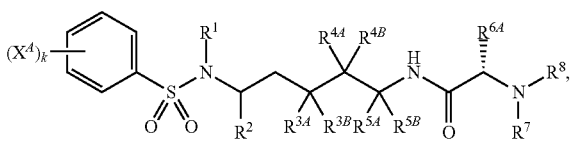

(II)

and pharmaceutically acceptable salts thereof, wherein:
$R^1$ is C$_{1-6}$ alkyl, C$_{1-6}$ fluoroalkyl, C$_{3-6}$ cycloalkyl, or C$_{1-6}$ alkyl substituted with C$_{3-6}$ cycloalkyl;
$R^2$ is CH(R$^J$)—Z;
$R^{5A}$ is H, C$_{1-4}$ alkyl, C$_{1-4}$ fluoroalkyl, C$_{1-4}$ alkyl substituted with OH, C$_{2-4}$ alkenyl, C$_{2-4}$ alkynyl, C$_{3-5}$ cycloalkyl, or CH$_2$—C$_{3-5}$ cycloalkyl;
$R^{5B}$ is H or C$_{1-6}$ alkyl; and
alternatively, $R^{5A}$ and $R^{5B}$ together with the carbon atom to which they are both attached form C$_{3-5}$ cycloalkyl; wherein all other variable are as originally defined (i.e. as defined in the Summary of the Invention).

Another class of compounds of the invention (alternatively referred to as Class C2) includes compounds of Formula III:

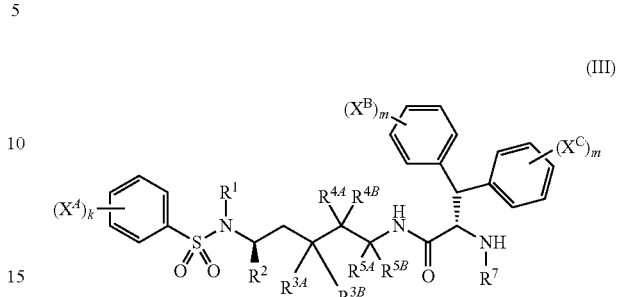

(III)

and pharmaceutically acceptable salts thereof, wherein all variables are as defined in Class C1.

A first subclass of Class C2 (alternatively referred to as Subclass C2-1) includes compounds of Formula IV:

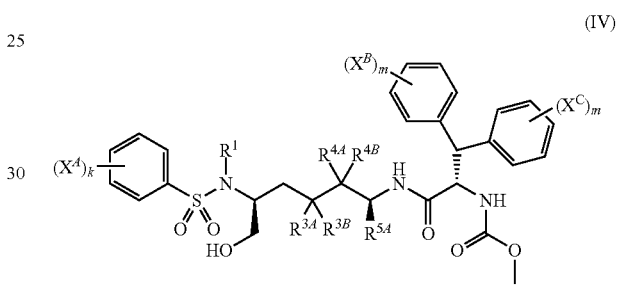

(IV)

and pharmaceutically acceptable salts thereof, wherein all variables are as defined in Class C2.

A second subclass of class C2 (alternatively referred to as Subclass C2-2) includes compounds of Formula V:

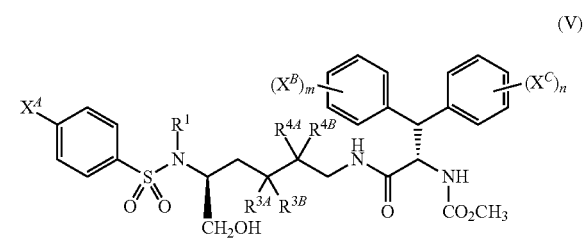

(V)

and pharmaceutically acceptable salts thereof, wherein:
$R^1$ is CH$_3$, CH$_2$CH$_3$, CH(CH$_3$)$_2$, CH$_2$CH$_2$CH$_3$, CH$_2$CH$_2$CH$_2$CH$_3$, CH$_2$CH(CH$_3$)$_2$, CH$_2$CH$_2$CH(CH$_3$)$_2$, CH$_2$CH$_2$CH$_2$F, cyclobutyl, CH$_2$-cyclopropyl, or CH$_2$-cyclobutyl substituted with 1 or 2F;
$R^{3A}$ is H or F;
$R^{3B}$ is H or F;
$R^{4A}$ is H or F;
$R^{4B}$ is H or F;
and provided that at least one of $R^{3A}$, $R^{3B}$, $R^{4A}$ and $R^{4B}$ is F;
$X^A$ is NH$_2$, C(O)CH$_3$, CH$_2$OH, or CH(CH$_3$)OH;
each $X^B$ and each $X^C$ are independently selected from the group consisting of:
(1) CH$_3$,
(2) CH$_2$CH$_3$, (3) CF$_3$,
(4) OH,
(5) OCH$_3$,
(6) OCF$_3$,
(7) Cl,
(8) Br,
(9) F,
(10) CN,
(11) NH$_2$,
(12) N(H)CH$_3$,
(13) N(CH$_3$)$_2$,
(14) C(O)CH$_3$,
(15) C(O)OCH$_3$,
(16) CH$_2$OH, and
(17) CH$_2$OCH$_3$;

m is an integer equal to 0, 1, or 2; and
n is an integer equal to 0, 1, or 2.

In some embodiments of Class C2, Subclass C2-1 and Subclass C2-2 the definitions of $R^{3A}$, $R^{3B}$, $R^{4A}$ and $R^{4B}$ are selected from the group consisting of sets (a) to (d) as follows:
(a) $R^{3A}$ is F; $R^{3B}$ is H; $R^{4A}$ is H; and $R^{4B}$ is H;
(b) $R^{3A}$ is F; $R^{3B}$ is F; $R^{4A}$ is H; and $R^{4B}$ is H;
(c) $R^{3A}$ is H; $R^{3B}$ is H; $R^{4A}$ is F; and $R^{4B}$ is H; and
(d) $R^{3A}$ is H; $R^{3B}$ is H; $R^{4A}$ is F; and $R^{4B}$ is F.

The invention also includes embodiments of Class C2, Subclass C2-1 and Subclass C2-2, and pharmaceutically acceptable salts thereof, wherein $R^1$ is CH(CH$_3$)$_2$, CH$_2$CH(CH$_3$)$_2$, CH$_2$CH$_2$CH(CH$_3$)$_2$, CH$_2$CH$_2$CH$_2$CH$_3$, or

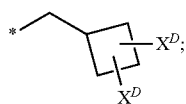

and each $X^D$ is independently H or F.

In further embodiments of Class C2, Subclass C2-1 and Subclass C2-2, m and n are either both 0 or both 1; and $X^B$ and $X^C$ are (i) both F and both para substituents, (ii) both F and both meta substituents, or (iii) both Cl and both para substituents.

Another embodiment of the present invention is a compound selected from the group consisting of:
N-[(5S)-5-{[(4-aminophenyl)sulfonyl](propan-2-yl)amino}-3,3-difluoro-6-hydroxyhexyl]-Nα-(methoxycarbonyl)-β-phenyl-L-phenylalaninamide;
N-{(5S)-2-fluoro-6-hydroxy-5-[{[4-(hydroxymethyl)phenyl]sulfonyl}(pentyl)amino]hexyl}-Nα-(methoxycarbonyl)-β-phenyl-L-phenylalaninamide;
N-[(5S)-5-{(1,3-benzothiazol-6-ylsulfonyl)[(3,3-difluorocyclobutyl)methyl]amino}-2,2-difluoro-6-hydroxyhexyl]-Nα-(methoxycarbonyl)-β-phenyl-L-phenylalaninamide;
N-{(5S)-5-[(1,3-benzothiazol-6-ylsulfonyl)(1H-pyrazol-4-ylmethyl)amino]-2,2-difluoro-6-hydroxyhexyl}-Nα-(methoxycarbonyl)-β-phenyl-L-phenylalaninamide;
N-{(5S)-5-[(1,3-benzothiazol-6-ylsulfonyl)(4,4-difluorocyclohexyl)amino]-2,2-difluoro-6-hydroxyhexyl}-Nα-(methoxycarbonyl)-β-phenyl-L-phenylalaninamide;
N$^6$—[N-(methoxycarbonyl)-β-phenyl-L-phenylalanyl]-N$^2$-(1,3-benzothiazol-6-ylsulfonyl)-N$^2$-[(3,3-difluorocyclobutyl)methyl]-5,5-difluoro-L-lysinamide;
N-[(5S)-5-{[(4-aminophenyl)sulfonyl](propan-2-yl)amino}-3,3-difluoro-6-hydroxyhexyl]-Nα-(methoxycarbonyl)-β-phenyl-L-phenylalaninamide;
N-[(5S)-5-{(1,3-benzothiazol-6-ylsulfonyl)[(3,3-difluorocyclobutyl)methyl]amino}-3,3-difluoro-6-hydroxyhexyl]-Nα-(methoxycarbonyl)-β-phenyl-L-phenylalaninamide; and
N-[(5S)-5-{[(4-aminophenyl)sulfonyl](propan-2-yl)amino}-3-fluoro-6-hydroxyhexyl]-Nα-(methoxycarbonyl)-β-phenyl-L-phenylalaninamide;
and pharmaceutically acceptable salts thereof.

Yet another embodiment of the present invention is a compound selected from:
N-[(2R,5S)-5-{[(4-aminophenyl)sulfonyl](3-methylbutyl)amino}-2-fluoro-6-hydroxyhexyl]-Nα-(methoxycarbonyl)-β-phenyl-L-phenylalaninamide; and
N-[(2S,5S)-5-{[(4-aminophenyl)sulfonyl](3-methylbutyl)amino}-2-fluoro-6-hydroxyhexyl]-Nα-(methoxycarbonyl)-β-phenyl-L-phenylalaninamide, and pharmaceutically acceptable salts thereof.

Another embodiment of the present invention is a compound of Formula I, or a pharmaceutically acceptable salt thereof, as originally defined or as defined in any of the foregoing embodiments, aspects, classes, or subclasses, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. The compounds of the invention have two or more asymmetric centers and can occur as mixtures of stereoisomers. It is understood that a substantially pure compound can be either a substantially pure mixture of stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c) or (d) or the combination of (e) or (f).

(q) A method for the prophylaxis or treatment of infection by HIV (e.g., HIV-1) in a subject in need thereof which comprises administering to the subject the pharmaceutical composition of (a), (b), (c), (d) or (e).

(r) A method for the prophylaxis, treatment, or delay in the onset or progression of AIDS in a subject in need thereof which comprises administering to the subject the pharmaceutical composition of (a), (b), (c), (d) or (e).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

An asterisk ("*") as the end of an open bond in a chemical group denotes the point of attachment of the group to the rest of the compound.

The term "aryl" refers to phenyl and naphthyl. An aryl of particular interest is phenyl.

The term "heteroaryl" refers to (i) a 5- or 6-membered heteroaromatic ring containing from 1 to 4 heteroatoms independently selected from N, O and S, wherein each N is optionally in the form of an oxide or (ii) is a 9- or 10-membered bicyclic, fused ring system containing from 1 to 4 heteroatoms independently selected from N, O and S, and wherein at least one of the rings is aromatic, each N in a ring is optionally in the form of an oxide, and each S is optionally S(O) or $S(O)_2$; and wherein the heteroaryl is unsubstituted, or substituted with from 1 to $4X^A$ substituents each of which is independently as set forth in the definition of AryQ.

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as unsubstituted, or substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^A$ or $X^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (i.e., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like.

Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |

TABLE A-continued

Antiviral Agents for Treating HIV infection or AIDS

| Name | Type |
| --- | --- |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, 57th edition (2003), the 58th edition (2004), or the 59th edition (2005). The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

Abbreviations employed herein include the following: Bn=benzyl; BOC (or Boc)=t-butyloxycarbonyl; Boc$_2$O=di-t-butyl carbonate; BOP=benzotriazol-1-yloxytris-(dimethylamino)phosphonium; BSA=bovine serum albumin; Cbz=benzyloxycarbonyl; DCM=dichloromethane; Dibal-H=diisobutylaluminum hydride; DMAP=4-dimethylaminopyridine; DMF=dimethylformamide; DMSO=dimethyl sulfoxide; Et=ethyl; EtOAc=ethyl acetate; EtOH=ethanol; Et$_3$N=triethylamine; HPLC=high performance liquid chromatography; i-PrOH=isopropanol; LCMS=liquid chromatography coupled with mass spectrometry; Me=methyl; Ms=mesyl or methanesulfonyl; NMR=nuclear magnetic resonance; Pd/C=palladium on carbon; PG=protecting group; Ph=phenyl; p-TsOH=p-toluenesulfonic acid; TBAF=tetrabutylammonium fluoride; TBS=tert-butyldimethylsilyl; TBS—Cl=t-butyldimethylsilyl chloride; TEA=triethylamine; TFA=trifluoroacetic acid; THF=tetrahydrofuran; TLC=thin layer chromatography; CF$_3$-TMS=trimethyl(trifluoromethyl)silane; TPAP=tetrapropylammonium perruthenate, and Ts=tosylate.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl unsubstituted, or substituted with one or more $X^4$.

Scheme A depicts a first method for the synthesis of halogen lysinol compounds of the invention, wherein amine can be protected as carbamate A1 which can then be reduced with an appropriate reducing reagent to provide A2. Alcohol A2 can be protected as a silyl ether to afford intermediate 3. According to *Tetrahedron Lett*. 1998, 39, 5671, selective RuO$_4$ mediated oxidation of A3, followed by the reduction of the resulting acyl carbamate provides alcohol A5. Boc removal and reductive amination with an appropriate aldehyde R$^1$CHO afford the desired compounds of type A6. Amine protection, followed by primary alcohol oxidation provides the corresponding aldehyde A8 which can be fluorinated (see *Organic Lett*. 2009, 11, 943) or chlorinated (see *Organic Lett*. 2006, 8, 5401) for the introduction of R$^4$ halogen group (R$^{4A}$ and/or R$^{4B}$ are F or Cl). Reductive amination, followed by selective N-deprotection affords compounds of type A11. Coupling of A11 with an appropriately substituted amino acid derivative and Cbz removal provide the desired compounds of type A13. Sulfonylation of A13 with an appropriate arylsulfonyl halide in presence of a base such as tertiary amine (e.g., TEA), a hydroxide (e.g., NaOH), or a carbonate (e.g., Na$_2$CO$_3$) gives the compounds of type A14. Removal of silyl ether can afford the desired compounds of type A15.

Scheme A:

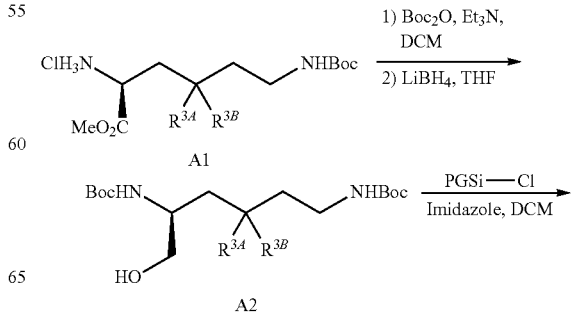

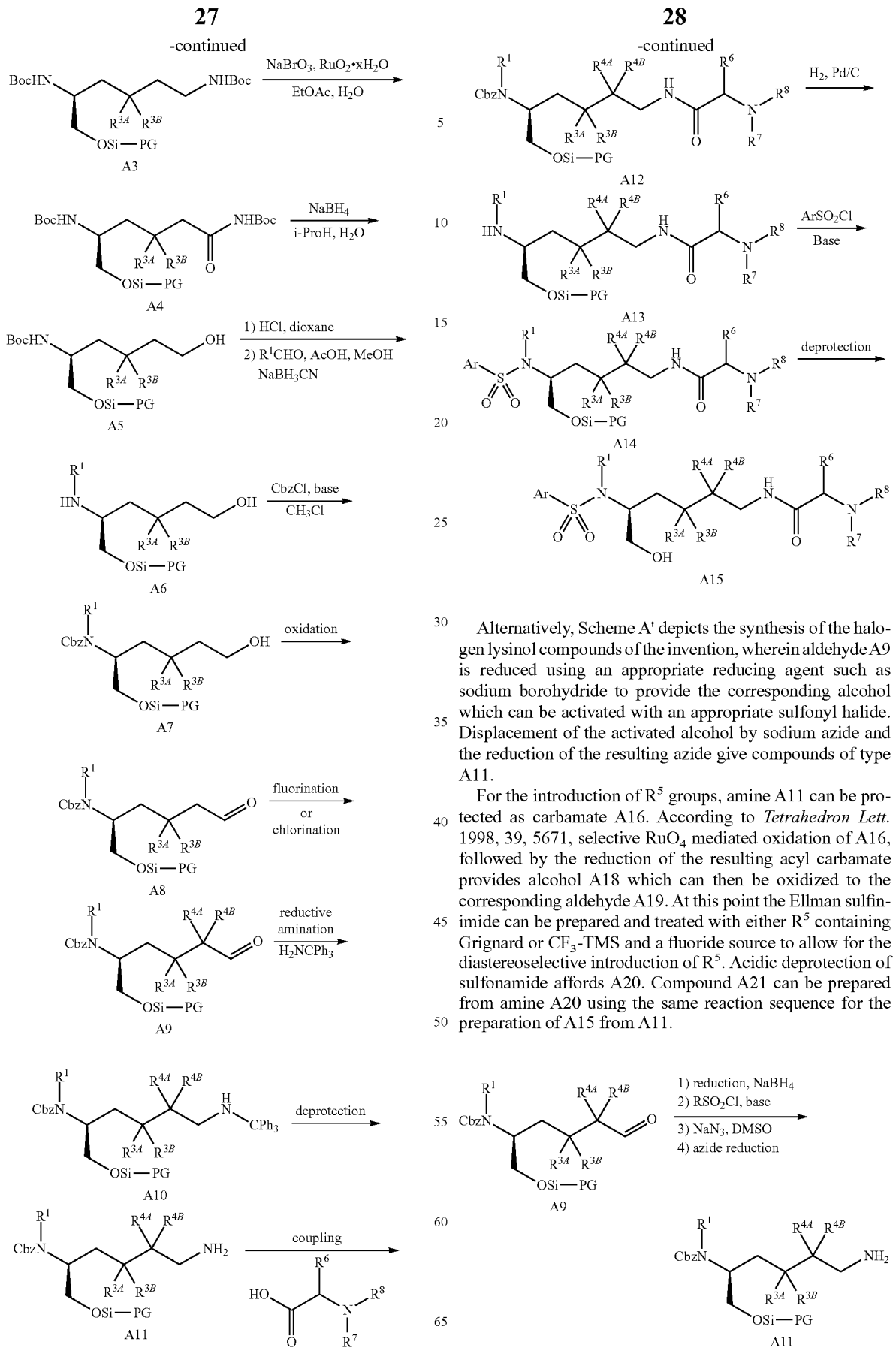

Alternatively, Scheme A' depicts the synthesis of the halogen lysinol compounds of the invention, wherein aldehyde A9 is reduced using an appropriate reducing agent such as sodium borohydride to provide the corresponding alcohol which can be activated with an appropriate sulfonyl halide. Displacement of the activated alcohol by sodium azide and the reduction of the resulting azide give compounds of type A11.

For the introduction of $R^5$ groups, amine A11 can be protected as carbamate A16. According to *Tetrahedron Lett.* 1998, 39, 5671, selective $RuO_4$ mediated oxidation of A16, followed by the reduction of the resulting acyl carbamate provides alcohol A18 which can then be oxidized to the corresponding aldehyde A19. At this point the Ellman sulfinimide can be prepared and treated with either $R^5$ containing Grignard or $CF_3$-TMS and a fluoride source to allow for the diastereoselective introduction of $R^5$. Acidic deprotection of sulfonamide affords A20. Compound A21 can be prepared from amine A20 using the same reaction sequence for the preparation of A15 from A11.

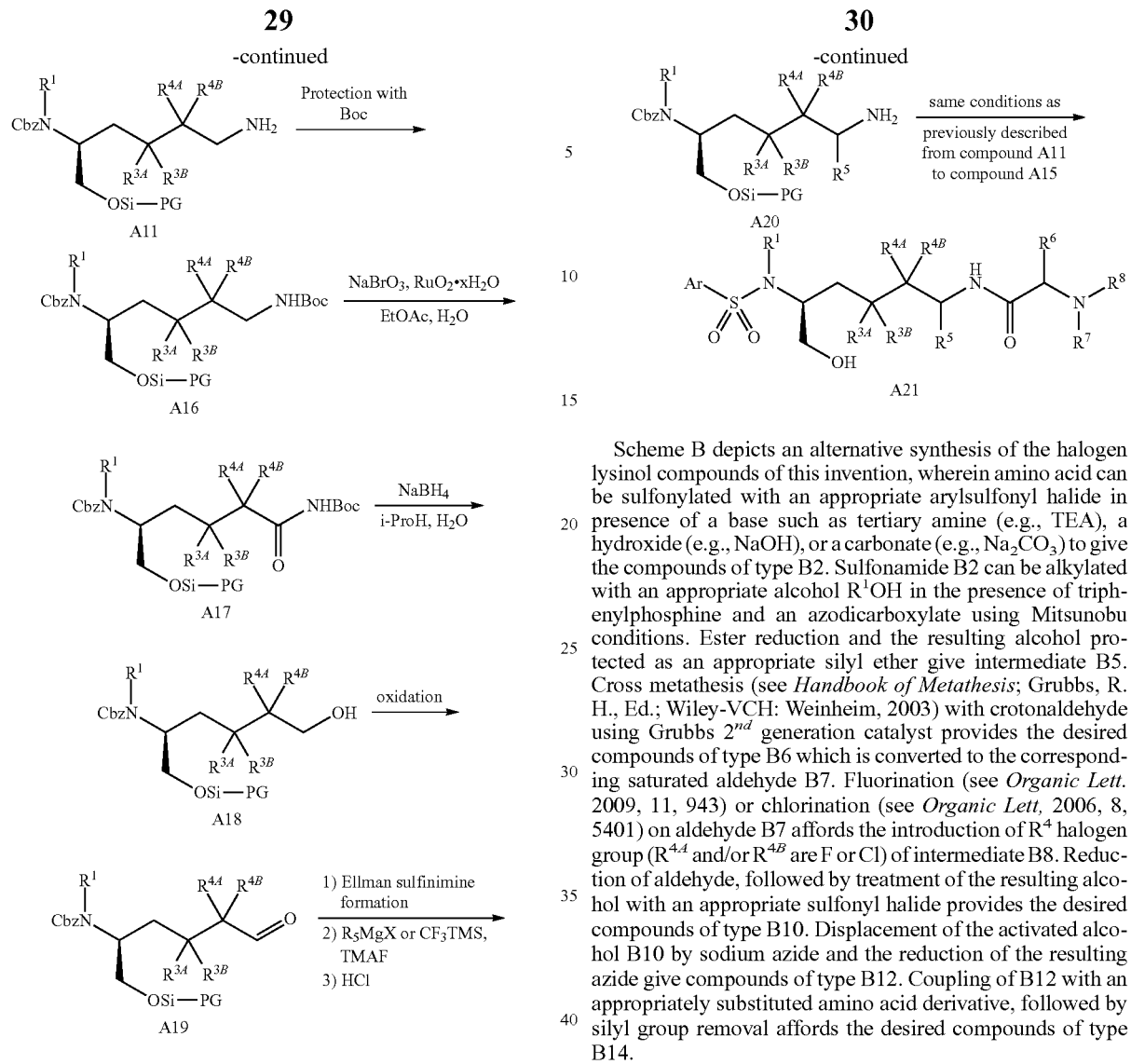

Scheme B depicts an alternative synthesis of the halogen lysinol compounds of this invention, wherein amino acid can be sulfonylated with an appropriate arylsulfonyl halide in presence of a base such as tertiary amine (e.g., TEA), a hydroxide (e.g., NaOH), or a carbonate (e.g., $Na_2CO_3$) to give the compounds of type B2. Sulfonamide B2 can be alkylated with an appropriate alcohol $R^1OH$ in the presence of triphenylphosphine and an azodicarboxylate using Mitsunobu conditions. Ester reduction and the resulting alcohol protected as an appropriate silyl ether give intermediate B5. Cross metathesis (see *Handbook of Metathesis*; Grubbs, R. H., Ed.; Wiley-VCH: Weinheim, 2003) with crotonaldehyde using Grubbs $2^{nd}$ generation catalyst provides the desired compounds of type B6 which is converted to the corresponding saturated aldehyde B7. Fluorination (see *Organic Lett.* 2009, 11, 943) or chlorination (see *Organic Lett,* 2006, 8, 5401) on aldehyde B7 affords the introduction of $R^4$ halogen group ($R^{4A}$ and/or $R^{4B}$ are F or Cl) of intermediate B8. Reduction of aldehyde, followed by treatment of the resulting alcohol with an appropriate sulfonyl halide provides the desired compounds of type B10. Displacement of the activated alcohol B10 by sodium azide and the reduction of the resulting azide give compounds of type B12. Coupling of B12 with an appropriately substituted amino acid derivative, followed by silyl group removal affords the desired compounds of type B14.

Scheme B:

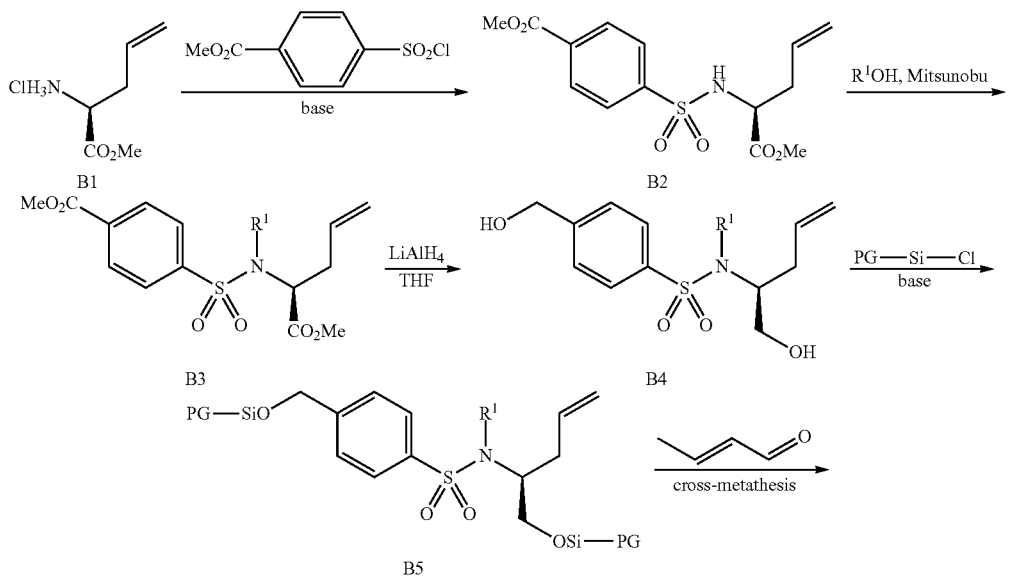

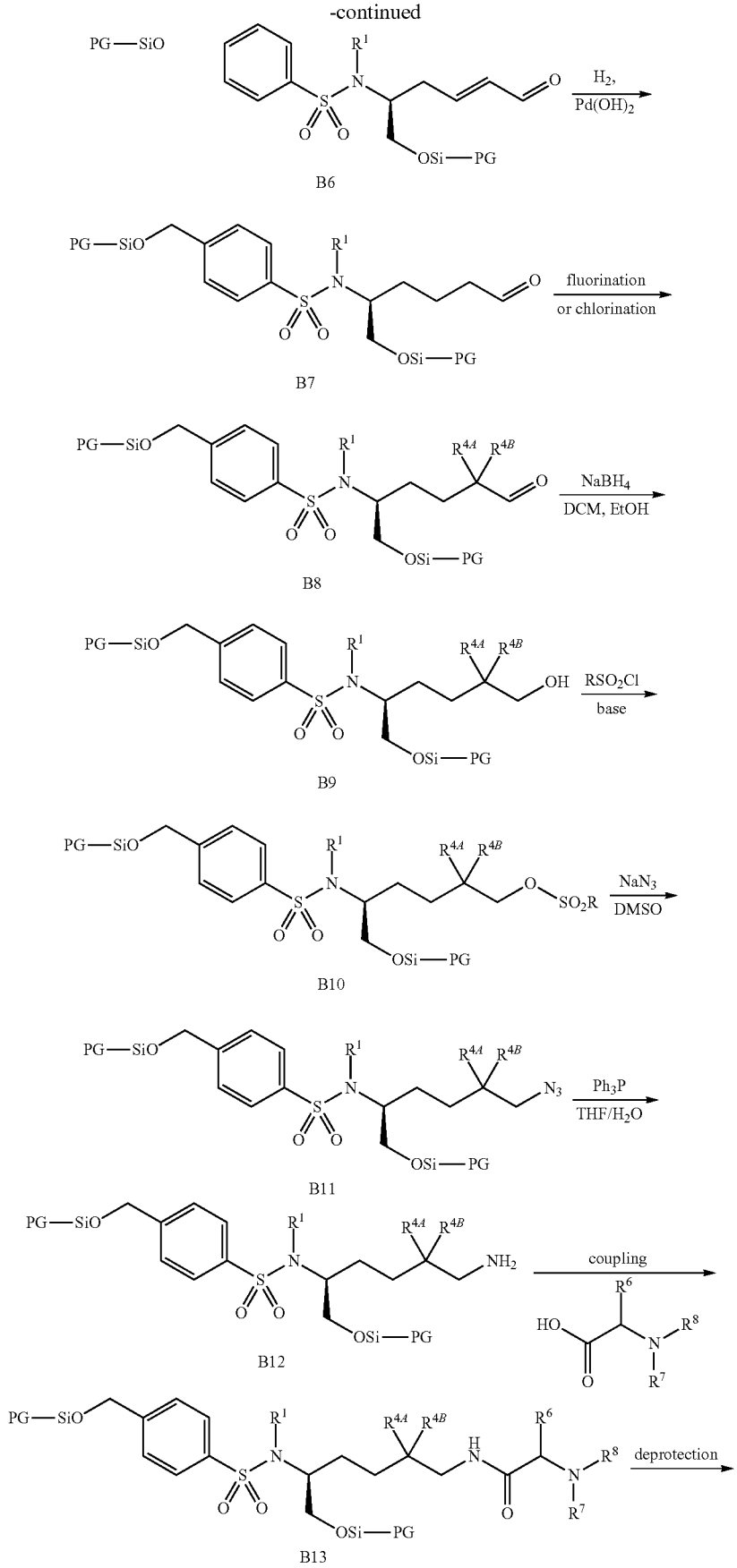

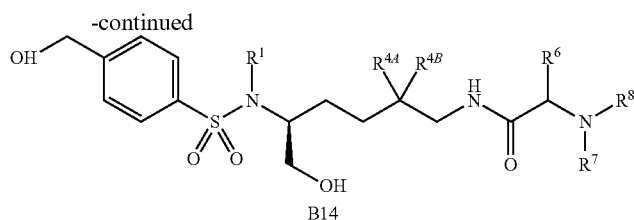

B14

Alternatively, Scheme B' depicts a synthesis wherein aldehyde B7 can be treated under reductive amination conditions, followed by N-deprotection affords the desired compounds of type B12.

Scheme B':

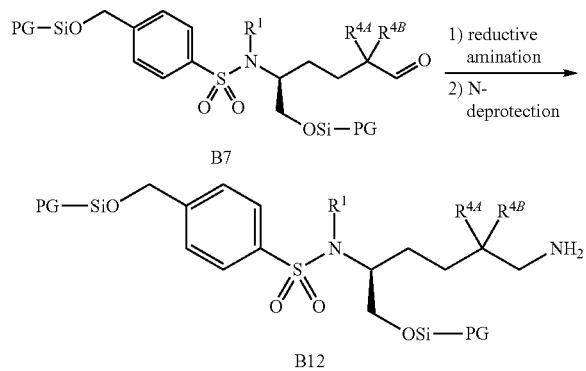

For the introduction of $R^5$ groups, aldehyde B8 can be converted to sulfinimide using Ellman chiral reagent and this sulfinimide can be treated with either $R^5$ containing Grignard or $CF_3$-TMS and a fluoride source to allow for the diastereoselective introduction of $R^5$. Acidic deprotection of sulfonamide affords B15. Compound B16 can be prepared from amine B15 using the same reaction sequence for the preparation of B14 from B12.

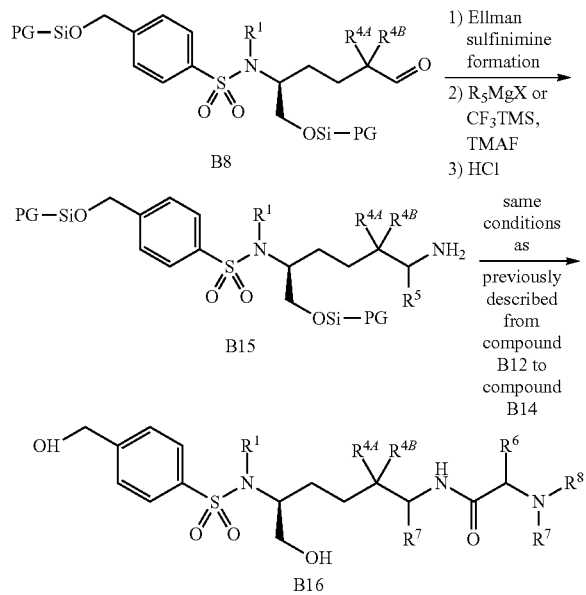

Scheme C depicts yet another methodology for the synthesis of the halogen lysional compounds of the invention that is similar to the methodology described in Scheme A and B, but which allows for the later introduction of the aryl sulfonamide and $R^1$ groups. Amino acid C1 is converted to the corresponding methyl or ethyl ester and the resulting amine C2 was fully protected as a bis-Boc. C3 can be selectively reduced using an appropriate reducing agent such as diisobutylaluminum hydride to provide aldehyde C4. Fluorination (see *Organic Lett.* 2009, 11, 943) or chlorination (see *Organic Lett* 2006, 8, 5401) on aldehyde C4 affords the introduction of $R^4$ halogen group ($R^{4A}$ and/or $R^{4B}$ are F or Cl) of intermediate C5 after reduction of aldehyde using an appropriate reducing agent such as sodium borohydride. Alcohol C5 is reacted with an appropriate sulfonyl halide, followed by treatment with sodium azide provides intermediate of type C7 which can be reduced to amine C8. Coupling of C8 with an appropriately substituted amino acid derivative, followed by Boc removal affords the desired compounds of type C10. The resulting amine can be sulfonylated with an appropriate arylsulfonyl halide in the presence of a base such as tertiary amine (e.g., TEA), a hydroxide (e.g., NaOH), or a carbonate (e.g., $Na_2CO_3$) to give the compounds of type C11. Sulfonamide C11 can be alkylated with an appropriate alcohol $R^1OH$ in the presence of triphenylphosphine and an azodicarboxylate using Mitsunobu conditions to afford, after saponification of ester with a hydroxide base such as LiOH or NaOH, intermediate C13. Acid C13 is activated as mixed anhydride with an appropriate alkyl chloroformate and the resulting mixed anhydride can be reduced using an appropriate reducing agent such as sodium borohydride to provide primary alcohol C14. Acid C13 can be also coupled with an appropriate amine to give the desired compounds of type C15. If the functionalities on Ar are compatible with the reduction conditions, ester C12 can be directly reduced to alcohol C14 using an appropriate reducing agent such as lithium borohydride.

Scheme C:

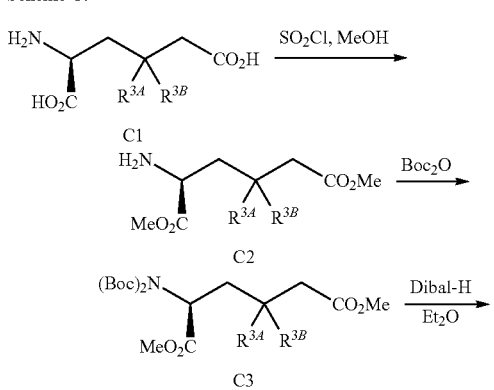

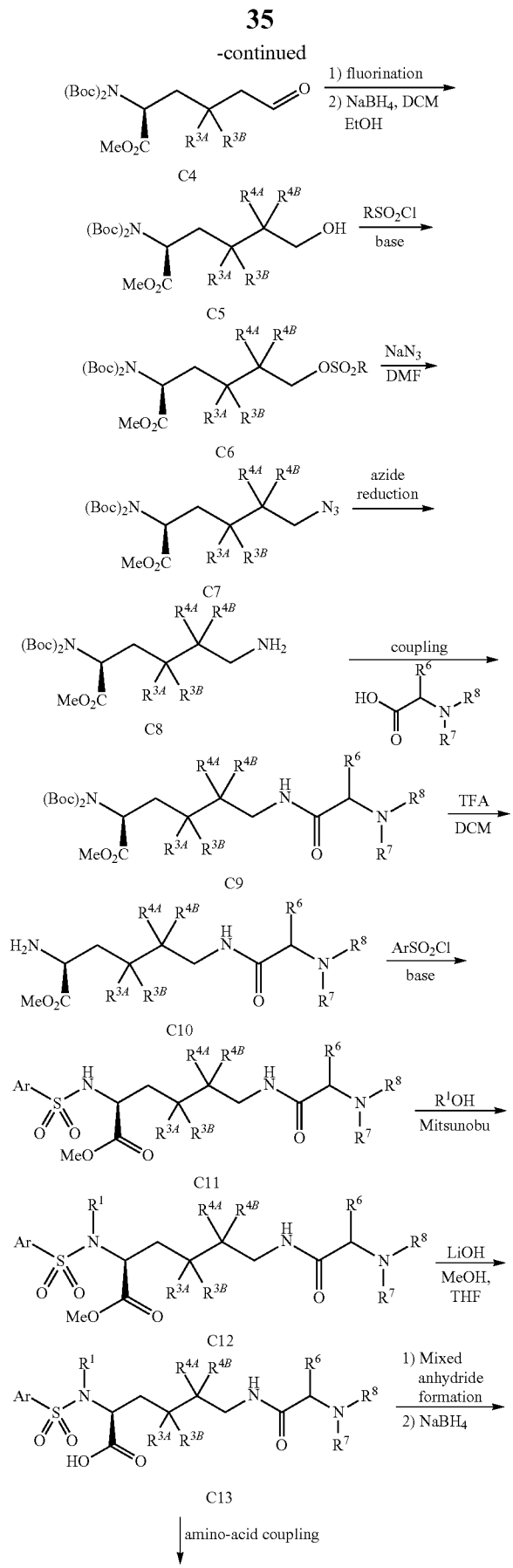

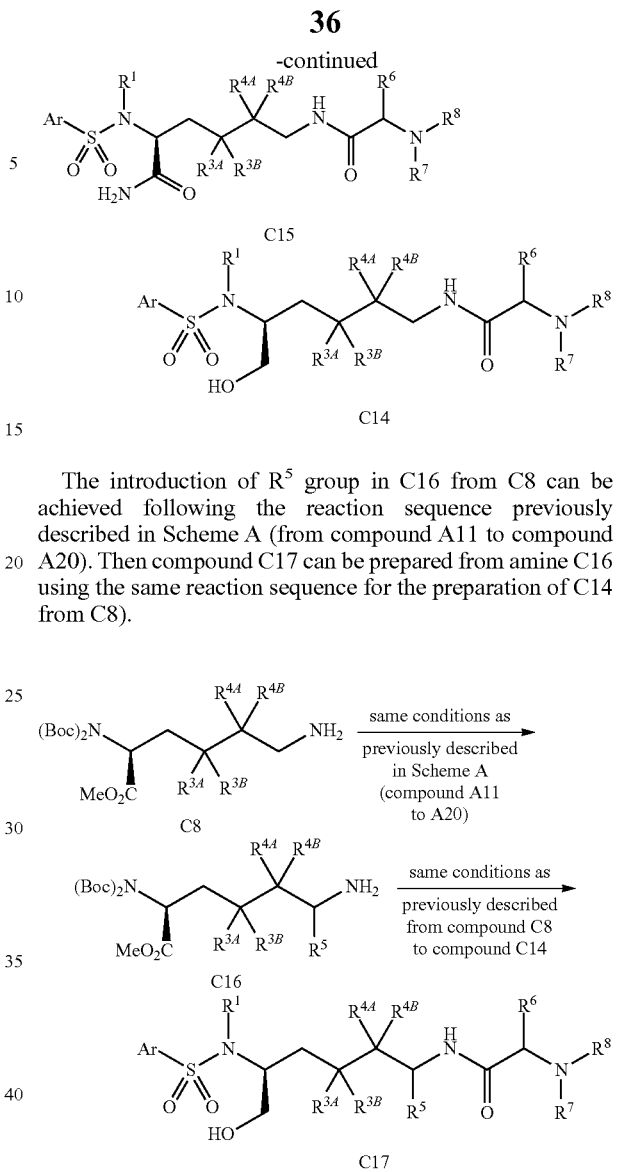

The introduction of $R^5$ group in C16 from C8 can be achieved following the reaction sequence previously described in Scheme A (from compound A11 to compound A20). Then compound C17 can be prepared from amine C16 using the same reaction sequence for the preparation of C14 from C8).

Scheme D depicts an alternative synthesis of halogen lysinol compounds of this invention, wherein amino diester D1 is fully protected as a bis-Boc. D2 which can be selectively reduced using an appropriate reducing agent such as diisobutylaluminum hydride to provide aldehyde D3. Fluorination (see *Organic Lett.* 2009, 11, 943) or chlorination (see *Organic Lett.* 2006, 8, 5401) on the resulting aldehyde for the introduction of $R^3$ halogen group ($R^{3A}$ and/or $R^{3B}$ are F or Cl), followed by Henry reaction (see *Comp. Org. Syn.* 1991, 2, 321) by treatment with an appropriately substituted nitroalkyl group and a catalytic base such as tetramethylguanidine gives Henry intermediate D4. The olefine in D4 can be reduced with an appropriate reducing agent to give the intermediate of type D5 in which the nitro group was reduced to the corresponding amine D6 by hydrogenation in the presence of a palladium source. Coupling of D6 with an appropriately substituted amino acid derivative, followed by Boc removal affords the desired compounds of type D8. The resulting amine can be sulfonylated with an appropriate arylsulfonyl halide in the presence, of a base such as tertiary amine (e.g., TEA), a hydroxide (e.g., NaOH), or a carbonate (e.g., $Na_2CO_3$) to give the compounds of type D9. Sulfonamide D9 can be alkylated with an appropriate alcohol $R^1OH$ in the presence of triphenylphosphine and an azodicarboxylate using Mitsunobu conditions to afford D10. Reduction of nitro or ester functionalities on Ar, followed by reduction of amino ester provides the desired compounds of type D11.

Scheme D:

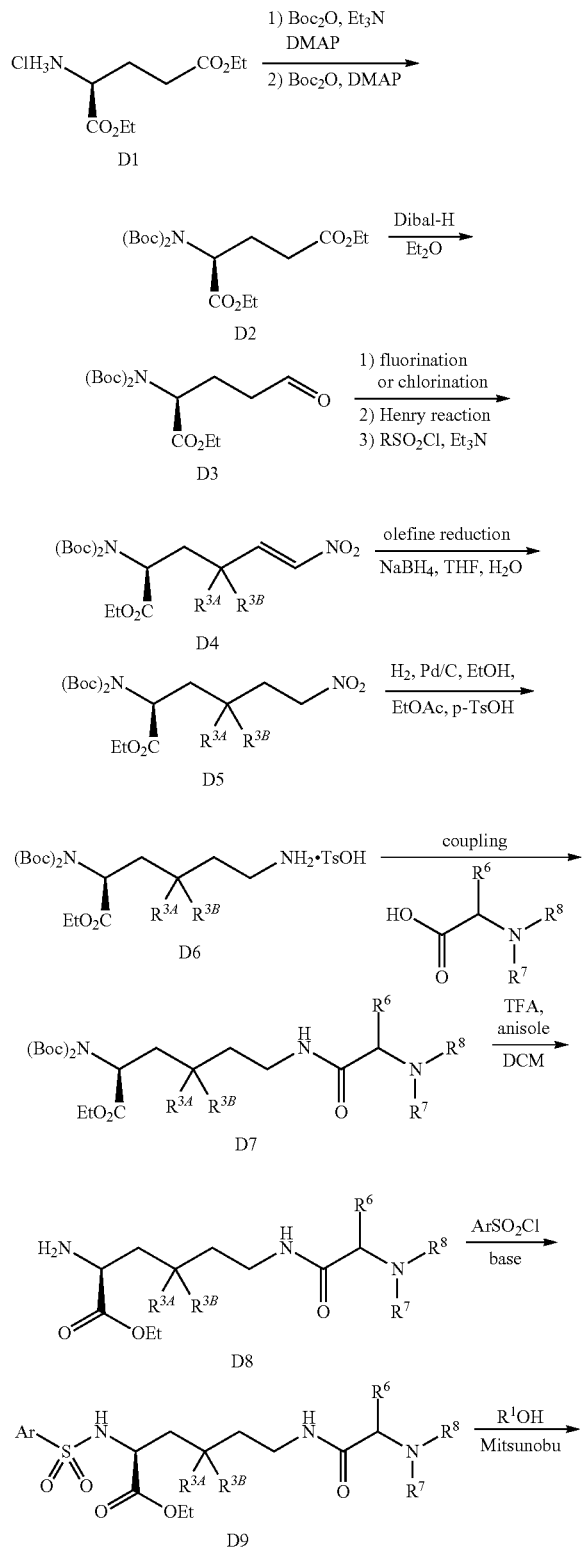

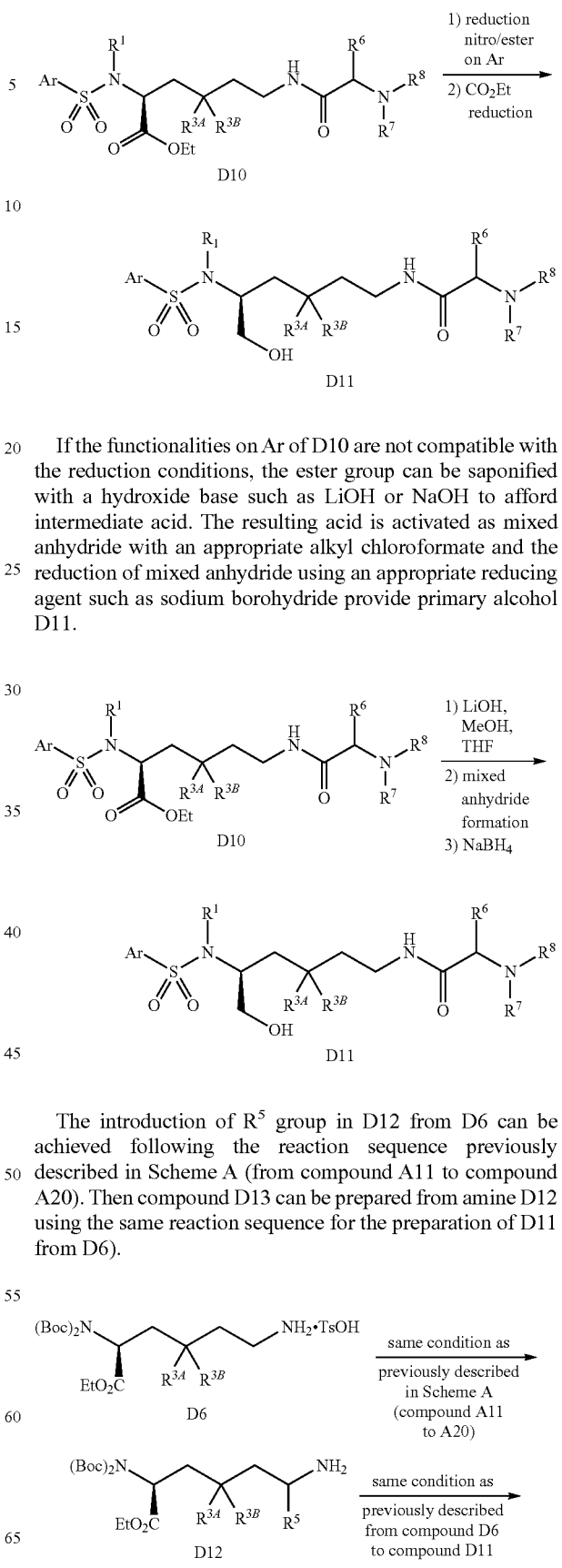

If the functionalities on Ar of D10 are not compatible with the reduction conditions, the ester group can be saponified with a hydroxide base such as LiOH or NaOH to afford intermediate acid. The resulting acid is activated as mixed anhydride with an appropriate alkyl chloroformate and the reduction of mixed anhydride using an appropriate reducing agent such as sodium borohydride provide primary alcohol D11.

The introduction of $R^5$ group in D12 from D6 can be achieved following the reaction sequence previously described in Scheme A (from compound A11 to compound A20). Then compound D13 can be prepared from amine D12 using the same reaction sequence for the preparation of D11 from D6).

-continued

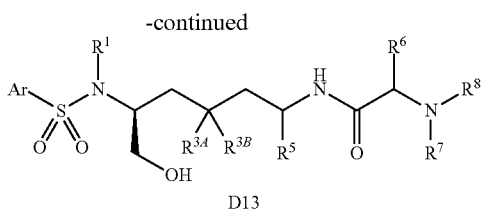

D13

Having described preferred embodiments of the invention, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

The term "room temperature" in the examples refers to the ambient temperature which was typically in the range of about 19° C. to 26° C.

Example 1

Preparation of N-[(5S)-5-{[(4-aminophenyl)sulfonyl](3-methylbutyl)amino}-2-fluoro-6-hydroxyhexyl]-Nα-(methoxycarbonyl)-β-phenyl-L-phenylalaninamide

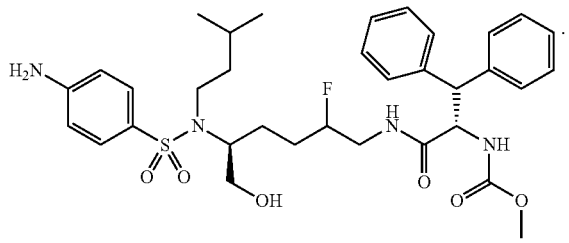 [SMILES: COC(=O)N[C@H](C(=O)NCC(F)CC[C@@H](CO)N(CCC(C)C)S(=O)(=O)c1ccc(N)cc1)C(c1ccccc1)c1ccccc1]

Step 1: preparation of tert-butyl{(2S)-6-[(tert-butoxycarbonyl)amino]-1-hydroxyhexan-2-yl}carbamate

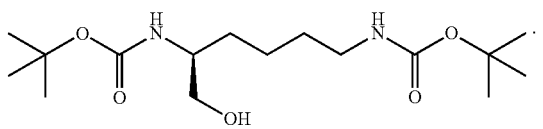 [SMILES: CC(C)(C)OC(=O)NCCCC[C@@H](CO)NC(=O)OC(C)(C)C]

To a solution of methyl $N^6$-(tert-butoxycarbonyl)-L-lysinate hydrochloride (5.0 g, 16.85 mmol) and triethylamine (2.82 mL, 20.22 mol) in dichloromethane (84 mL) was added a solution of di-tert-butyl dicarbonate (3.7 g, 16.85 mmol) in dichloromethane (10 mL). The reaction mixture was stirred at room temperature overnight, poured into 10% $KHSO_4$, and extracted with dichloromethane (2×). The combined organics were washed with saturated aqueous $NaHCO_3$, brine, dried over $MgSO_4$, filtered and concentrated to yield 6.1 g of methyl $N^2,N^6$-bis(tert-butoxycarbonyl)-L-lysinate as an off white solid. MS: M+Na=383. The residue was dissolved in THF (85 mL), and the solution was cooled to 0° C. 2 M of $LiBH_4$ in THF (12.69 mL, 25.4 mmol) was slowly added. The reaction mixture was stirred at room temperature for 1 hour, then at 50° C. for 1 hour. It was then cooled to 0° C. and methanol was carefully added (1.5 mL). The reaction temperature was allowed to stand at room temperature, and 1 N NaOH (2 mL) was added followed by the addition of brine. The reaction mixture was vigorously stirred at room temperature for 30 min, then extracted with EtOAc (2×). The combined organics were washed with brine, dried over $MgSO_4$, filtered and concentrated to yield 5.8 g of bis-Boc-lysinol material as a colorless viscous oil. MS (M+Na)=355.

Step 2: preparation of tert-butyl[(5S)-5-[(tert-butoxycarbonyl)amino]-6-{[tert-butyl(diphenyl)silyl]oxy}hexyl]carbamate

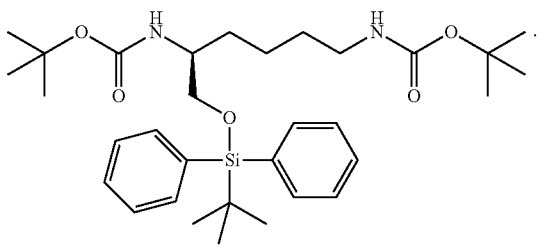 [SMILES: CC(C)(C)OC(=O)NCCCC[C@@H](CO[Si](c1ccccc1)(c1ccccc1)C(C)(C)C)NC(=O)OC(C)(C)C]

To a stirred solution of the material from Step 1 (212 g, 637 mmol) in dichloromethane (2500 mL) at 0° C. were added imidazole (86 g, 1263 mmol) and tert-butylchlorodiphenylsilane (200 mL, 779 mmol). The reaction mixture was stirred at room temperature overnight, poured into water and extracted with dichloromethane (2×). The combined organics were washed with brine, dried over $MgSO_4$, filtered and concentrated. The residue was purified by flash chromatography on silica gel using EtOAc-hexanes to afford 340 g of the title compound. $^1$H NMR ($CHCl_3$-d): δ 7.65-7.60 (m, 4H), 7.46-7.34 (m, 6H), 4.73-4.61 (b, 1H), 4.51-4.50 (b, 1H), 3.73-3.61 (m, 2H), 3.58-3.51 (m, 1H), 3.17-3.05 (m, 2H), 1.55-1.41 (m, 2H), 1.45 (s, 18H, 1.37-1.22 (m, 4H), 1.03 (s, 9H).

Step 3: preparation of tert-butyl[(5S)-5-[(tert-butoxycarbonyl)amino]-6-{[tert-butyl(diphenyl)silyl]oxy}hexanoyl]carbamate

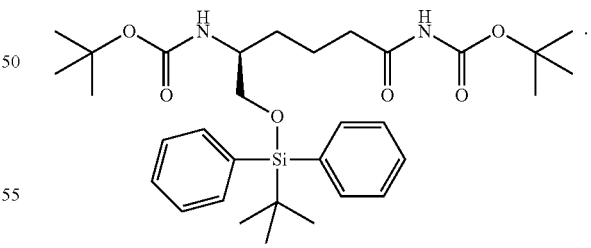

To a stirred solution of the material from Step 2 (339.5 g, 595 mmol) in EtOAc (1000 mL) and $H_2O$ (1400 mL) at room temperature were added sodium bromate (250 g, 1657 mmol) and ruthenium oxide hydrate (3 g, 19.86 mmol). The reaction mixture was stirred at room temperature overnight, 50% of conversion. The mixture was then heated at 55° C. overnight. Additional sodium bromate (100 g) was added and the resulting mixture was heated at 40° C. for 12 hours. Upon cooling to room temperature, the reaction mixture was filtered through celite. The filtrate was extracted with EtOAc (2×). The combined organics were then washed with aqueous sodium bisulfite and brine, and dried over MgSO₄. The filtrate was treated with charcoal (Darco® G-60, Norit Americas Inc., Marshall, Tex.) and filtered through a pad of silica gel. The filtrate was concentrated in vacuo and the residue was purified by flash chromatography on silica gel using EtOAc-hexanes to yield 128 g of the title compound as a colorless viscous oil. $^1$H NMR (CHCl₃-d): δ 7.67-7.62 (m, 4H), 7.58-7.52 (b, 1H), 7.42-7.35 (m, 6H), 4.72-4.65 (b, 1H), 3.70-3.62 (m, 2H), 3.58-3.52 (m, 1H), 2.76-2.62 (m, 2H), 1.75-1.55 (m, 2H), 1.48 (s, 9H), 1.42 (s, 9H), 1.32-1.23 (m, 2H), 1.05 (s, 9H).

Step 4: preparation of tert-butyl[(2S)-1-{[tert-butyl (diphenyl)silyl]oxy}-6-hydroxyhexan-2-yl]carbamate

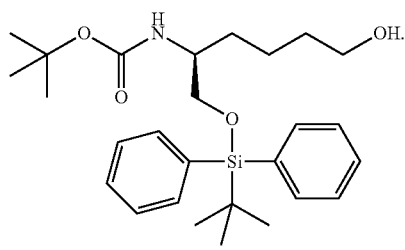 [SMILES: CC(C)(C)OC(=O)N[C@@H](CCCCO)CO[Si](c1ccccc1)(c1ccccc1)C(C)(C)C]

To a stirred solution of the material from Step 3 (128 g, 219 mmol) in 2-propanol (1800 mL) and water (180 mL) at room temperature was added sodium borohydride (8.28 g, 219 mmol). The reaction mixture was stirred at room temperature overnight. Additional 2 g of sodium borohydride was added and stirred at room temperature for an additional 4 hours. The reaction mixture was concentrated to ⅓ volume and diluted with EtOAc and 1 N NaOH (100 mL). The reaction mixture was partitioned, and extracted with EtOAc. The combined organics were washed with brine, dried over MgSO₄, filtered and concentrated. The residue was purified by flash chromatography on silica gel using EtOAc-hexanes (0 to 50%) to afford 65 g of the title compound. $^1$H NMR (CHCl₃-d): δ 7.67-7.62 (m, 4H), 7.45-7.35 (m, 6H), 4.72-4.65 (b, 1H), 3.72-3.62 (m, 2H), 3.60-3.52 (m, 3H), 1.62-1.42 (m, 4H), 1.42 (s, 9H), 1.42-1.23 (m, 2H), 1.05 (s, 9H).

Step 5: preparation of (5S)-6-{[tert-butyl(diphenyl) silyl]oxy}-5-[(3-methylbutyl)amino]hexan-1-ol

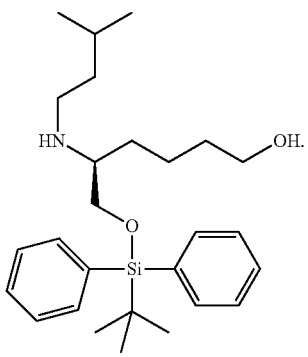 [SMILES: CC(C)CCN[C@@H](CCCCO)CO[Si](c1ccccc1)(c1ccccc1)C(C)(C)C]

Material from Step 4 (9.8 g, 20.78 mmol) was dissolved in a solution of 4 M HCl (51.9 mL, 208 mmol) in dioxane. The reaction mixture was stirred at room temperature for 1 hour. It was concentrated in vacuo, then dichloromethane was added and concentrated again in vacuo. The residue (1.75 g, 4.29 mmol) was dissolved in methanol (30 mL), and isovaleraldehyde (0.35 mL, 4.50 mmol) and acetic acid (0.25 mL, 4.29 mmol) were added. The reaction mixture was stirred at room temperature for 30 minutes. Sodium cyanoborohydride (0.323 g, 5.15 mmol) was then added to the mixture and it was stirred at room temperature overnight. The reaction mixture was concentrated, and partitioned between EtOAc and saturated aqueous NaHCO₃ and extracted with EtOAc. The combined organics were washed with brine, dried over MgSO₄, filtered and concentrated in vacuo to yield the title compound, which was used without further purification.

Step 6: preparation of benzyl[(2S)-1-{[tert-butyl (diphenyl)silyl]oxy}-6-hydroxyhexan-2-yl](3-methylbutyl)carbamate

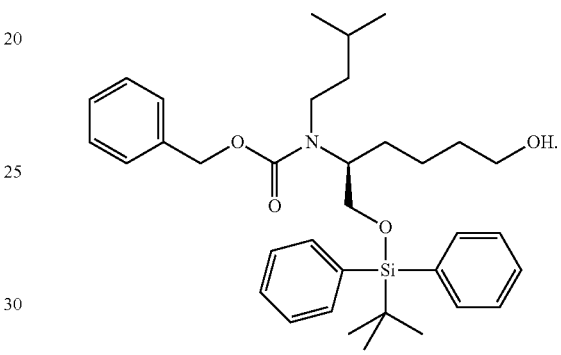

To a stirred solution of the material from Step 5 (8 g, 18.11 mmol) in a 2:1 mixture of chloroform and saturated aqueous NaHCO₃ (271 mL) was added benzyl chloroformate (2.59 mL, 118.11 mmol). The reaction mixture was stirred at room temperature for 1 hour, partitioned and extracted with chloroform. The combined organics were washed with brine, dried over MgSO₄, filtered and concentrated in vacuo. The residue was purified by flash chromatography on silica gel using EtOAc-hexanes (10 to 70%) to yield 7 g of the title compound. LCMS (M+1)=576

Step 7: preparation of benzyl[(2S)-1-{[tert-butyl (diphenyl)silyl]oxy}-6-oxohexan-2-yl](3-methylbutyl)carbamate

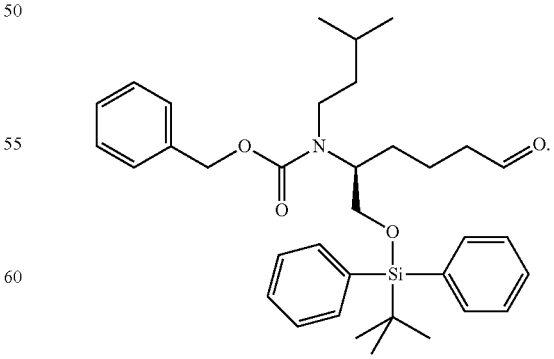

To a stirred solution of the material from Step 6 (3.27 g, 5.68 mmol) in dichloromethane (57 mL) were added 4-methylmorpholine N-oxide (0.8 g, 6.81 mmol), and activated 4

Å molecular sieves. After stirring at room temperature for 10 minutes, TPAP (0.1 g, 0.28 mmol) was added portionwise. The reaction mixture was stirred at room temperature for 3 hours, and then filtered through a silica gel plug. The filtrate was concentrated in vacuo to afford the title compound which was used directly at Step 8.

Step 8: preparation of benzyl[(2S)-1-{[tert-butyl (diphenyl)silyl]oxy}-5-fluoro-6-oxohexan-2-yl](3-methylbutyl)carbamate

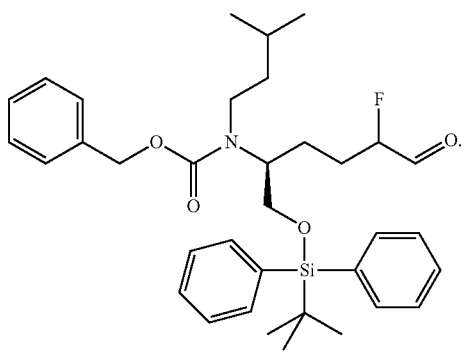 [SMILES: CC(C)CCN(C(=O)OCc1ccccc1)[C@@H](CCC(F)C=O)CO[Si](c1ccccc1)(c1ccccc1)C(C)(C)C]

Racemic 5-benzyl-2-2,3-trimethylimidazolidin-4-one dichloroacetic acid (109 mg, 0.314 mmol) and N-fluorobenzenesulfonimide (593 mg, 1.88 mmol) were dissolved in 10% i-PrOH-THF (3.75 mL). The reaction mixture was cooled to −20° C., and the compound from Step 7 (900 mg, 1.57 mmol) in 1.25 mL of 10% i-PrOH-THF was added. The reaction mixture was stirred at −20° C. for 24 hours, 2 volumes of ether were added, and the resulting mixture was vigorously stirred, filtered through Davisil® silica (W.R. Grace & Co.-Conn.), and eluted with ether. 5 mL of methyl sulfide was added to the eluted reaction mixture. The reaction mixture was partitioned between EtOAc and saturated aqueous NaHCO$_3$ and extracted with EtOAc (2×). The combined organics were washed with brine, dried over MgSO$_4$, filtered and concentrated in vacuo to afford the title compound which was used directly at Step 9. $^1$H NMR (DMSO-d$_6$): δ7.66-7.52 (m, 5H), 7.51-7.25 (m, 10H), 5.08 (s, 2H), 4.90-4.83 (m, 1H), 3.70-3.55 (m, 1H), 3.53-3.36 (m, 2H), 3.17-2.99 (m, 2H), 1.63-1.32 (m, 7H), 0.96 (s, 9H), 0.88-0.72 (m 6H), aldehyde signal missing due to hydrate form.

Step 9: preparation of benzyl[(2S)-1-{[tert-butyl (diphenyl)silyl]oxy}-5-fluoro-6-(tritylamino)hexan-2-yl](3-methylbutyl)carbamate

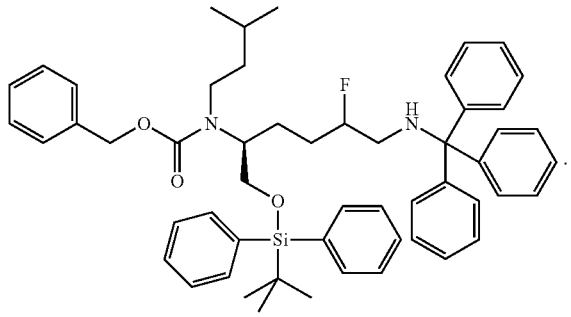 [SMILES: CC(C)CCN(C(=O)OCc1ccccc1)[C@@H](CCC(F)CNC(c1ccccc1)(c1ccccc1)c1ccccc1)CO[Si](c1ccccc1)(c1ccccc1)C(C)(C)C]

To a stirred solution of the material from Step 8 (900 mg, 1.52 mmol) in dichloroethane (15 mL) at room temperature were added tritylamine (394 mg, 1.52 mmol) and sodium triacetoxyborohydride (483 mg, 2.28 mmol). The reaction mixture was stirred at room temperature overnight, poured into saturated aqueous NaHCO$_3$, and extracted with dichloromethane (2×). The combined organics were dried over MgSO$_4$, filtered and concentrated in vacuo. The residue was purified by flash chromatography on silica gel using EtOAc-hexanes to yield 1.2 g of the title compound.

Step 10: preparation of benzyl[(2S)-6-amino-1-{[tert-butyl(diphenyl)silyl]oxy}-5-fluorohexan-2-yl] (3-methylbutyl)carbamate

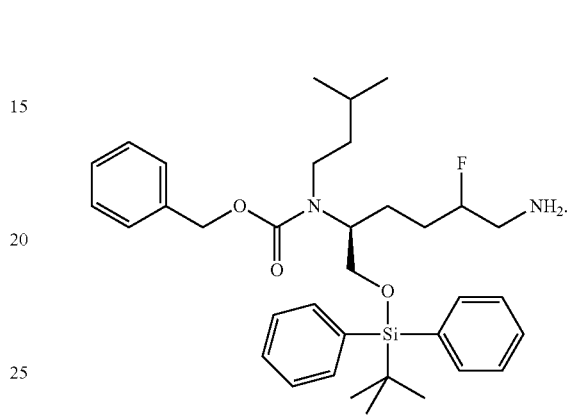

To a stirred solution of the material from Step 9 (225 mg, 0.27 mmol) in dichloroethane (1.3 mL) at 0° C. was added trifluoroacetic acid (500 μL, 6.49 mmol). The reaction mixture was stirred at 0° C. for 1 hour, poured into saturated aqueous NaHCO$_3$, and extracted with dichloromethane (2×). The combined organics were dried over MgSO$_4$, filtered and concentrated in vacuo. The residue was purified by flash chromatography on silica gel using EtOAc-hexanes to afford 160 mg of the title compound. LCMS (M+1)=593.

Step 11: preparation of benzyl[(2S)-1-{[tert-butyl (diphenyl)silyl]oxy}-5-fluoro-6-{[N-(methoxycarbonyl)-β-phenyl-L-phenylalanyl]amino}hexan-2-yl](3-methylbutyl)carbamate

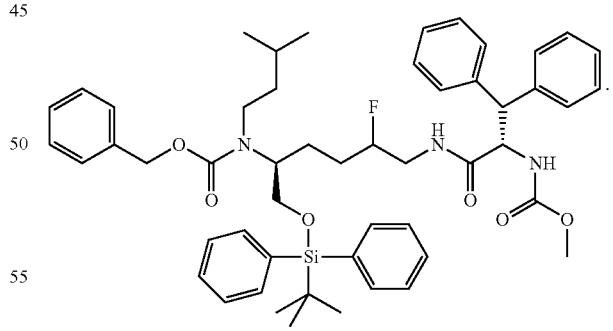

To a stirred solution of the material from Step 10 (86 mg, 0.145 mmol) in THF (1 mL) and water (333 μL) at 0° C. was added NaHCO$_3$ (49 mg, 0.58 mmol) and followed by portionwise addition of 2,5-dioxopyrrolidin-1-yl N-(methoxycarbonyl)-β-phenyl-L-phenylalaninate (63 mg, 0.16 mmol). The reaction mixture was stirred at room temperature overnight, poured into brine, and extracted with EtOAc (2×). The combined organics were dried over MgSO$_4$, filtered and concentrated in vacuo. The residue was purified by flash chromatography on silica gel using EtOAc-hexanes to afford 110 mg of the title compound. $^1$H NMR (DMSO-d$_6$): δ 8.24-8.12 (m, 1H), 7.67-7.53 (m, 4H), 7.51-7.37 (m, 6H), 7.37-7.20 (m, 11H), 7.19-7.07 (m, 2H), 7.03-6.91 (m, 1H), 5.15-4.90 (m, 3H), 4.29-4.19 (m, 1H), 3.96-3.76 (m, 1H), 3.74-3.47 (m, 2H), 3.06 (s, 3H), 3.16-2.97 (m, 4H), 2.96-2.76 (m, 1H), 1.55-1.28 (m, 5H), 1.27-1.01 (m, 2H), 0.97 (s, 9H), 0.85 (d, J=4.2 Hz, 3H), 0.77 (d, J=4.20 Hz, 3H).

Step 12: preparation of N-{(5S)-6-{[tert-butyl(diphenyl)silyl]oxy}-2-fluoro-5-[(3-methylbutyl)amino]hexyl}-Nα-(methoxycarbonyl)-β-phenyl-L-phenylalaninamide

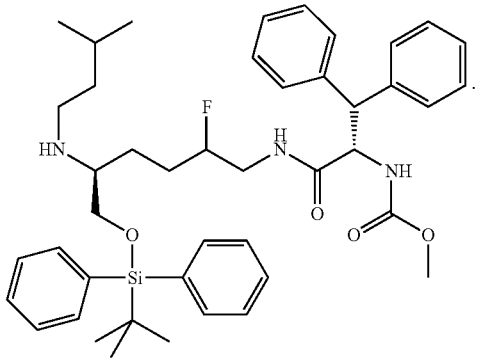 [SMILES: COC(=O)N[C@H](C(=O)NCC(F)CC[C@@H](CO[Si](c1ccccc1)(c1ccccc1)C(C)(C)C)NCCC(C)C)C(c1ccccc1)c1ccccc1]

A solution of the material from Step 11 (110 mg, 0.126 mmol) in methanol (1 mL) was degassed with nitrogen, then 10% Pd/C (14 mg, 0.013 mmol) was added. The reaction mixture was stirred under hydrogen (1 atm) for 3 hours. The mixture was filtered through celite and washed with dichloromethane. The filtrate was concentrated in vacuo to afford 86 mg of the title compound which was used directly at Step 13. LCMS (M+1)=740

Step 13: preparation of N-[(5S)-6-{[tert-butyl(diphenyl)silyl]oxy}-2-fluoro-5-{(3-methylbutyl)[(4-nitrophenyl)sulfonyl]amino}hexyl]-Nα-(methoxycarbonyl)-β-phenyl-L-phenylalaninamide

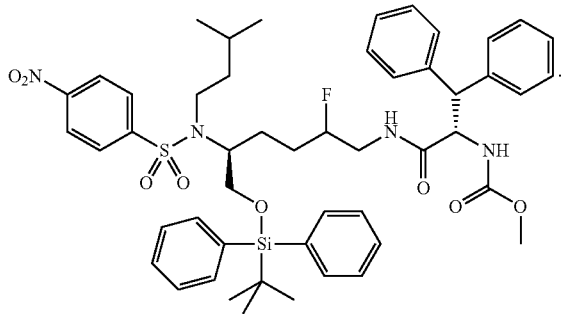 [SMILES: COC(=O)N[C@H](C(=O)NCC(F)CC[C@@H](CO[Si](c1ccccc1)(c1ccccc1)C(C)(C)C)N(CCC(C)C)S(=O)(=O)c1ccc([N+](=O)[O-])cc1)C(c1ccccc1)c1ccccc1]

To a stirred solution of the material from Step 12 (85 mg, 0.12 mmol) in dichloromethane (1.1 mL) were added N,N-diisopropylethylamine (30 μL, 0.172 mmol) and 4-nitrobenzenesulfonyl chloride (28 mg, 0.126 mmol). The reaction mixture was stirred at room temperature overnight. Additional N,N-diisopropylethylamine (30 μL, 0.172 mmol) and 4-nitrobenzenesulfonyl chloride (6 mg, 0.03 mmol) were added, stirred at room temperature for 2 hours. The reaction mixture was concentrated in vacuo, and the residue was purified by flash chromatography on silica gel using EtOAc-hexanes to afford 85 mg of the title compound. LCMS (M+1)=947

Step 14: preparation of N-[(5S)-2-fluoro-6-hydroxy-5-{(3-methylbutyl)[(4-nitrophenyl)sulfonyl]amino}hexyl]-Nα-(methoxycarbonyl)-β-phenyl-L-phenylalaninamide

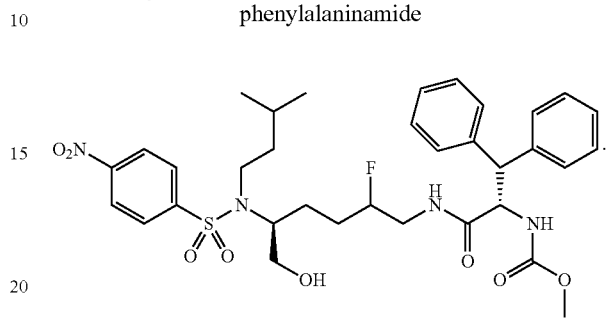

To a stirred solution of the material from Step 13 (80 mg, 0.086 mmol) in THF (1.7 mL) was added 1.0 M TBAF (104 μL, 0.104 mmol) in THF. The reaction mixture was stirred at room temperature overnight. The reaction mixture was concentrated in vacuo, and the residue was purified by flash chromatography on silica gel using EtOAc-hexanes to afford 45 mg of the title compound. LCMS (M+1)=687.

Step 15: preparation of N-[(5S)-5-{[(4-aminophenyl)sulfonyl](3-methylbutyl)amino}-2-fluoro-6-hydroxyhexyl]-Nα-(methoxycarbonyl)-β-phenyl-L-phenylalaninamide

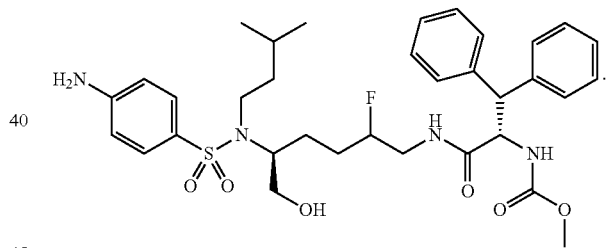

A solution of the material from Step 14 (45 mg, 0.065 mmol) in (1:1) in ethyl acetate-ethanol (1 mL) was degassed with nitrogen, then 20% palladium hydroxide on carbon (4.6 mg, 0.007 mmol) was added. The reaction mixture was stirred under hydrogen (1 atm) for 3 hours. The reaction mixture was filtered through celite and washed with dichloromethane to afford 30 mg of the title compound. $^1$H NMR (DMSO-d$_6$): δ 8.17 (d, J=6.98 Hz, 1H), 7.46-7.38 (m, 3H), 7.35-7.22 (m, 6H), 7.23-7.10 (m, 4H), 6.60 (dd, J=8.50, 3.17 Hz, 2H), 5.94 (s, 2H), 5.03-4.94 (m, 1H), 4.71-4.64 (m, 1H), 4.26 (d, J=11.45 Hz, 1H), 3.94-3.66 (m, 1H), 3.55-3.39 (m, 1H), 3.42 (s, 3H), 3.29-3.22 (m, 2H), 3.13-2.77 (m, 4H), 1.67-1.01 (m, 7H), 0.84 (dd, J=6.31, 3.38 Hz, 6H). The mixture of diastereomers was separated by SFC (AD-H, 4.6×250 mm, 30% i-PrOH in CO$_2$, 2.4 mL/min, 100 bar, 40° C.

Example 1-1

First eluting isomer eluted at 10.96 min. N-[(2R or S,5S)-5-{[(4-aminophenyl)sulfonyl](3-methylbutyl)amino}-2-fluoro-6-hydroxyhexyl]-Nα-(methoxycarbonyl)-β-phenyl-L-phenylalaninamide. LCMS (M+1)=657.

Example 1-2

Second eluting isomer eluted at: 13.25 min. N-[(2R or S,5S)-5-{[(4-aminophenyl)sulfonyl](3-methylbutyl)amino}-2-fluoro-6-hydroxyhexyl]-Nα-(methoxycarbonyl)-β-phenyl-L-phenylalaninamide. LCMS (M+1)=657 LCMS (M+1)=657.

Example 2

Preparation of N-{(5S)-2-fluoro-6-hydroxy-5-[{[4-(hydroxymethyl)phenyl]sulfonyl}(pentyl)amino]hexyl}-Nα-(methoxycarbonyl)-β-phenyl-L-phenylalaninamide

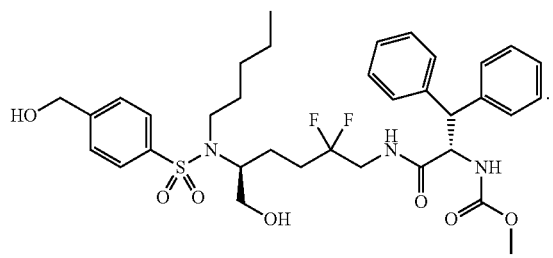 [SMILES: CCCCCN([C@H](CO)CCC(F)(F)CNC(=O)[C@@H](NC(=O)OC)C(c1ccccc1)c1ccccc1)S(=O)(=O)c1ccc(CO)cc1]

Step 1: preparation of methyl 4-{[(2S)-1-methoxy-1-oxopent-4-en-2-yl](pentyl)sulfamoyl}benzoate

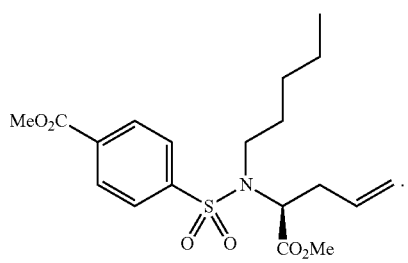 [SMILES: C=CC[C@@H](C(=O)OC)N(CCCCC)S(=O)(=O)c1ccc(C(=O)OC)cc1]

To a stirred solution of methyl 4-{[(2S)-1-methoxy-1-oxopent-4-en-2-yl]sulfamoyl}benzoate (10.5 g, 32.1 mmol); prepared as described in Vacca et al. (WO 2009/042094 A2), 1-pentahol (8.48 g, 96 mmol) and triphenylphosphine (12.62 g, 48.1 mmol) in THF (321 mL) was slowly added diisopropyl azodicarboxylate (9.35 mL, 48.1 mmol). The reaction mixture was stirred at room temperature overnight and concentrated to dryness in vacuo. The residue was purified by flash chromatography on silica gel using EtOAc-hexanes to afford 11.5 g of the title compound. $^1$H NMR (DMSO-d$_6$): δ 8.14 (d, J=8.16 Hz, 2H), 7.95 (d, J=8.18 Hz, 2H), 5.71-5.61 (m, 1H), 5.10 (d, J=17.20 Hz, 1H), 5.02 (d, J=10.31 Hz, 1H), 4.57 (dd, J=9.21, 5.98 Hz, 1H), 3.91 (s, 3H), 3.42 (s, 3H), 3.25-3.02 (m, 1H), 2.70-2.57 (m, 1H), 2.46-2.36 (m, 1H), 1.58-1.41 (m, 2H), 1.29-1.13 (m, 6H), 0.83 (t, J=7.15 Hz, 3H).

Step 2: preparation of 4-(hydroxymethyl)-N-[(2S)-1-hydroxypent-4-en-2-yl]-N-pentylbenzenesulfonamide

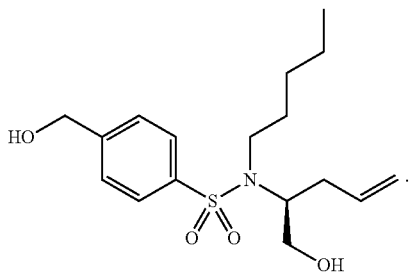 [SMILES: C=CC[C@@H](CO)N(CCCCC)S(=O)(=O)c1ccc(CO)cc1]

To a stirred solution of the material from Step 1 (2 g, 5.03 mmol) in THF (33.5 mL) at 0° C. was slowly added 1.0 M lithium aluminum hydride (10 mL, 10.06 mmol). The reaction mixture was stirred at 0° C. for 20 minutes. Water (383 μL) was carefully added, followed by the slow addition of 15% NaOH (383 μL) and water (1.2 mL). The reaction mixture was vigorously stirred for 10 minutes. It was filtered through celite and washed with ether and EtOAc. The filtrate was concentrated in vacuo to afford 1.7 g of the title compound which was directly used at Step 2. LCMS (M+Na)=364.

Step 3: preparation of 4-({[tert-butyl(dimethyl)silyl]oxy}methyl)-N-[(2S)-1-{[tert-butyl(dimethyl)silyl]oxy}pent-4-en-2-yl]-N-pentylbenzenesulfonamide

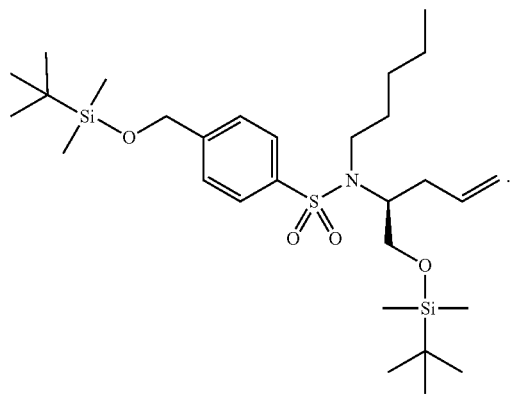 [SMILES: C=CC[C@@H](CO[Si](C)(C)C(C)(C)C)N(CCCCC)S(=O)(=O)c1ccc(CO[Si](C)(C)C(C)(C)C)cc1]

To a stirred solution of the material from Step 2 (10.5 g, 30.7 mmol), imidazole (4.61 g, 67.6 mmol) and DMAP (0.376 g, 3.07 mmol) in dichloromethane (307 mL) was added TBS—Cl (9.50 g, 63.0 mmol). The reaction mixture was stirred at room temperature for 5 hours, it was then concentrated to ⅓ volume, poured into 10% KHSO$_4$, extracted with ether and EtOAc. Water (383 μL) was carefully added, followed by the slow addition of 15% NaOH (383 μL) and water (1.2 mL). The combined organics were washed with saturated aqueous NaHCO$_3$ and brine, dried over MgSO$_4$, filtered and concentrated in vacuo. The residue was purified by flash chromatography on silica gel using EtOAc-hexanes to afford 12 g of the title compound. ¹H NMR (DMSO-d₆): δ 7.78 (d, J=8.05 Hz, 2H), 7.50 (d, J=8.05 Hz, 2H), 5.67-5.50 (m, 1H), 5.02-4.96 (m, 1H), 4.95-4.90 (m, 1H), 4.79 (s, 2H), 3.76-3.73 (m, 1H), 3.56-3.49 (m, 2H), 3.21-3.13 (m, 1H), 3.09-2.99 (m, 1H), 2.35-2.29 (m, 1H), 2.11-2.06 (m, 1H), 1.60-1.47 (m, 2H), 1.30-1.15 (m, 4H), 0.91 (s, 9H), 0.89-0.83 (m, 3H), 0.81 (s, 9H), 0.09 (s, 6H), −0.04 (s, 6H).

Step 4: preparation of 4-({[tert-butyl(dimethyl)silyl]oxy}methyl)-N-[(2S,4E)-1-{[tert-butyl(dimethyl)silyl]oxy}-6-oxohex-4-en-2-yl]-N-pentylbenzenesulfonamide

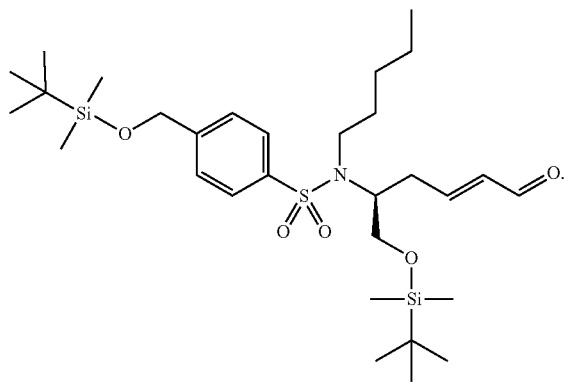 [SMILES: CCCCCN([C@@H](C/C=C/C=O)CO[Si](C)(C)C(C)(C)C)S(=O)(=O)c1ccc(CO[Si](C)(C)C(C)(C)C)cc1]

A solution of the material from Step 3 (9.5 g, 16.67 mmol) and crotonaldehyde (6.90 mL, 83 mmol) in dichloromethane (183 mL) was heated at reflux. Grubbs' 2$^{nd}$ Generation catalyst (0.71 g, 0.833 mmol) was added, and the reaction mixture was stirred at reflux for 4 hours. The reaction mixture was concentrated to dryness in vacuo and the residue was purified by flash chromatography on silica gel using EtOAc-hexanes to afford 7.4 g of the title compound. LCMS (M+Na)=620.

Step 5: preparation of 4-({[tert-butyl(dimethyl)silyl]oxy}methyl)-N-[(2S)-1-{[tert-butyl(dimethyl)silyl]oxy}-6-oxohexan-2-yl]-N-pentylbenzenesulfonamide

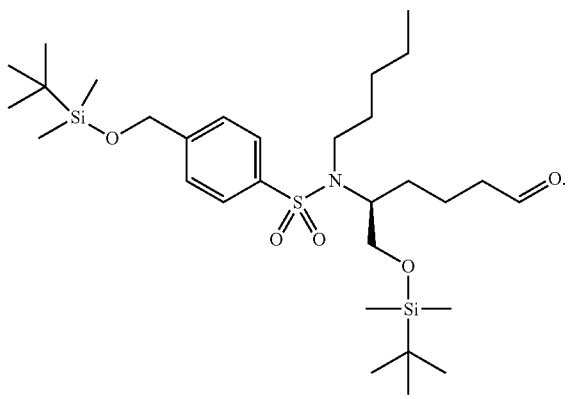 [SMILES: CCCCCN([C@@H](CCCC=O)CO[Si](C)(C)C(C)(C)C)S(=O)(=O)c1ccc(CO[Si](C)(C)C(C)(C)C)cc1]

A solution of the material from Step 4 (7.2 g, 12.04 mmol) in (1:1) EtOAc-ethanol (232 mL) was degassed with nitrogen, and 20% palladium hydroxide on carbon (0.72 g, 1.03 mmol) was added. The reaction mixture was stirred under hydrogen (1 atm) for 2 hours. The reaction mixture was filtered through celite and washed with dichloromethane. The filtrate was concentrated in vacuo and the residue was purified by flash chromatography on silica gel using EtOAc-hexanes to afford 4 g of the title compound. ¹H NMR (DMSO-d₆): δ 9.60 (s, 1H), 7.79 (d, J=7.96 Hz, 2H), 7.50 (d, J=7.99 Hz, 2H), 4.79 (s, 2H), 3.68-3.60 (m, 1H), 3.45 (t, J=20.48 Hz, 2H), 3.23-3.09 (m, 1H), 3.08-2.98 (m, 1H), 2.37 (d, J=7.09 Hz, 2H), 1.62-1.06 (m, 10H), 0.91 (s, 9H), 0.84 (t, J=6.94 Hz, 3H), 0.80 (s, 9H), 0.09 (s, 6H), −0.06 (s, 6H).

Step 6: preparation of N-[(2S)-1-{[tert-butyl(dimethyl)silyl]oxy}-5,5-difluoro-6-oxohexan-2-yl]-4-({[tert-butyl(dimethyl)silyl]oxy}methyl)-N-pentylbenzenesulfonamide

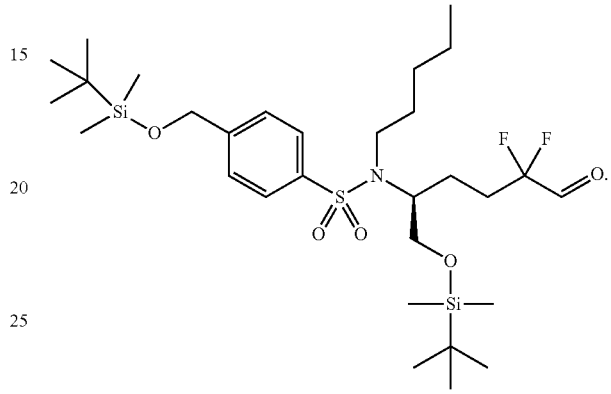

To a stirred suspension of DL-proline (84 mg, 0.733 mmol) and N-fluorobenzenesulfonimide (1.27 g, 4.03 mmol) in 10% i-PrOH-THF (4.6 mL) at room temperature was added a solution of the material from Step 5 (1.1 g, 1.833 mmol) in 10% i-PrOH-THF (1.5 mL). The reaction mixture was stirred at room temperature for 24 hours. Additional N-fluorobenzenesulfonimide (1.27 g, 4.03 mmol) was added and stirred at room temperature for 72 hours. The reaction mixture was cooled to −78° C. and ether (12.2 mL) was added. It was vigorously stirred, filtered through Davisil® silica, and eluted with ether. 5 mL of methyl sulfide was added. The reaction mixture was partitioned between ether and saturated aqueous NaHCO₃, extracted with ether (2×). The combined organics were washed with brine, dried over MgSO₄, filtered and concentrated in vacuo to afford the title compound which was used directly at Step 7.

Step 7: preparation of N-[(2S)-1-{[tert-butyl(dimethyl)silyl]oxy}-5,5-difluoro-6-hydroxyhexan-2-yl]-4-({[tert-butyl(dimethyl)silyl]oxy}methyl)-N-pentylbenzenesulfonamide

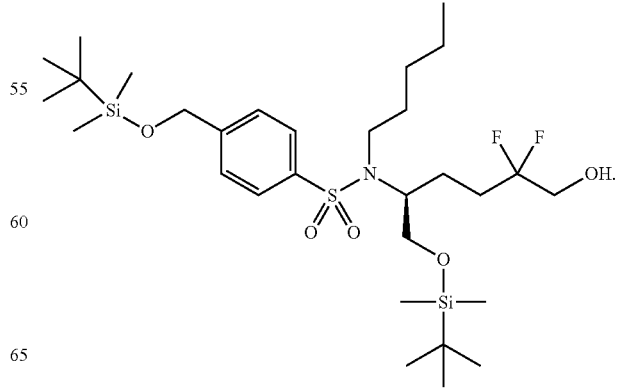

To a stirred solution of the material from Step 6 (1.17 g, 1.833 mmol) in dichloromethane (22 mL) and ethanol (14 mL) was added sodium borohydride (347 mg, 9.17 mmol). The reaction mixture was stirred at room temperature for 2 hours, poured into saturated aqueous NH$_4$Cl and extracted with dichloromethane (2×). The combined organics were washed with saturated aqueous NaHCO$_3$ and brine, dried over MgSO$_4$, filtered and concentrated in vacuo. The residue was purified by flash chromatography on silica gel using EtOAc-hexanes to afford 625 mg of the title compound. LCMS (M+Na)=660.

Step 8: preparation of (5S)-6-{[tert-butyl(dimethyl) silyl]oxy}-5-[{[4-({[tert-butyl(dimethyl)silyl] oxy}methyl)phenyl]sulfonyl}(pentyl)amino]-2,2- difluorohexyl methanesulfonate

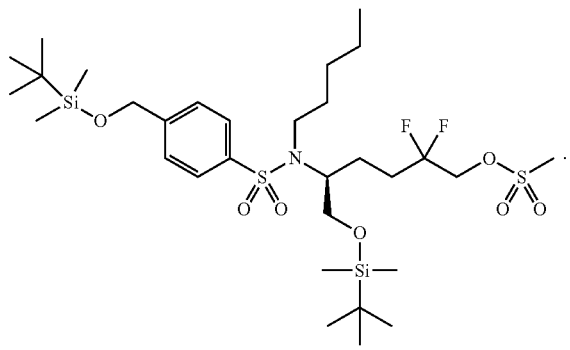 [SMILES: CCCCCN([C@@H](CCC(F)(F)COS(C)(=O)=O)CO[Si](C)(C)C(C)(C)C)S(=O)(=O)c1ccc(CO[Si](C)(C)C(C)(C)C)cc1]

To a stirred solution of the material from Step 7 (242 mg, 0.38 mmol) in dichloromethane (3.8 mL) at 0° C. were added N,N-diisopropylaethylamine (99 μL, 0.57 mmol) and methanesulfonyl chloride (33 μL, 0.417 mmol). The reaction mixture was stirred at room temperature overnight, poured into saturated aqueous NH$_4$Cl and extracted with dichloromethane (2×). The combined organics were washed with brine, dried over MgSO$_4$, filtered and concentrated in vacuo. The residue was purified by flash chromatography on silica gel using EtOAc-hexanes to afford 167 mg of the title compound. LCMS (M+Na)=738.

Step 9: preparation of N-[(2S)-6-azido-1-{[tert-butyl (dimethyl)silyl]oxy}-5,5-difluorohexan-2-yl]-4- ({[tert-butyl(dimethyl)silyl]oxy}methyl)-N-pentyl- benzenesulfonamide

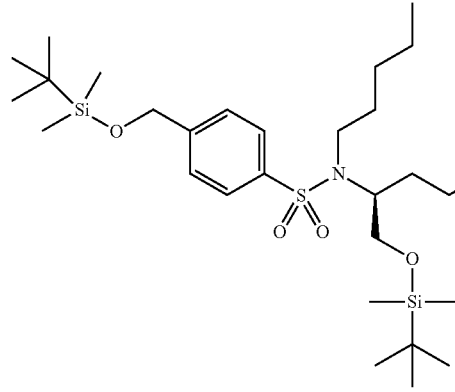

To a stirred solution of the material from Step 8 (167 mg, 0.233 mmol) in DMSO (2.3 mL) were added sodium azide (23 mg, 0.35 mmol) and 18-crown-6 (3 mg, 0.012 mmol). The reaction mixture was stirred at 125° C. for 24 hours. Upon cooling to room temperature, the reaction mixture was concentrated to dryness in vacuo. LCMS showed that TBS group was removed. The residue was dissolved in dichloromethane (2.3 mL). Imidazole (32 mg, 0.465 mmol), DMAP (1 mg, 0.008 mmol) and TBS—Cl (70 mg, 0.465 mmol) were added. The reaction mixture was stirred at room temperature overnight, poured into water and extracted with dichloromethane (2×). The combined organics were washed with 1 N HCl, saturated aqueous NaHCO$_3$ and brine, dried over MgSO$_4$, filtered and concentrated in vacuo. The residue was purified by flash chromatography on silica gel using EtOAc-hexanes to afford 60 mg of the title compound.

Step 10: preparation of N-[(2S)-6-amino-1-{[tert- butyl(dimethyl)silyl]oxy}-5,5-difluorohexan-2-yl]-4- ({[tert-butyl(dimethyl)silyl]oxy}methyl)-N-pentyl- benzenesulfonamide

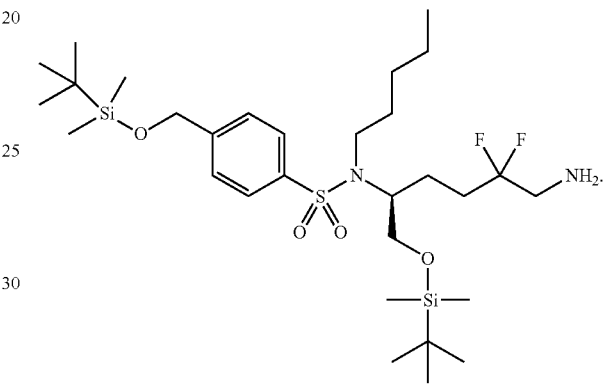

To a stirred solution of the material from Step 9 (60 mg, 0.09 mmol) in THF (1.7 mL) and water (86 μL) was added triphenylphosphine (50 mg, 0.19 mmol). The reaction mixture was stirred at room temperature for 2 hours. Then additional water (86 μL) was added, the reaction mixture was heated at reflux for 5 hours. Upon cooling to room temperature, the reaction mixture was concentrated to dryness in vacuo and the residue was purified by flash chromatography on silica gel using EtOAc-hexanes to afford 42 mg of the title compound. LCMS (M+Na)=637.

Step 11: preparation of N-{(5S)-6-{[tert-butyl(dim- ethyl)silyl]oxy}-5-[{[4-({[tert-butyl(dimethyl)silyl] oxy}methyl)phenyl]sulfonyl}(pentyl)amino]-2,2- difluorohexyl}-Nα-(methoxycarbonyl)-β-phenyl-L- phenylalaninamide

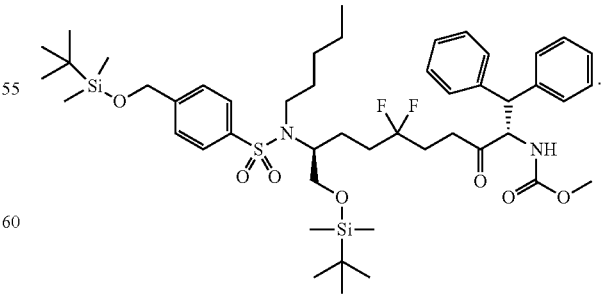

To a stirred solution of the material from Step 10 (42 mg, 0.066 mmol), N-(methoxycarbonyl)-β-phenyl-L-phenylalanine (39 mg, 0.132 mmol), and N,N-diisopropylethylamine (46 μL, 0.264 mmol) in 1 mL of DMF was added BOP (58 mg, 0.132 mmol). The reaction mixture was stirred at room temperature overnight, poured into saturated aqueous NaHCO₃, and extracted with EtOAc (2×). The combined organics were washed with brine, dried over MgSO₄, filtered and concentrated in vacuo. The residue was purified by flash chromatography on silica gel using EtOAc-hexanes (0 to 100%) to afford the title compound.

Step 12: preparation of N-{(5S)-2,2-difluoro-6-hydroxy-5-[{[4-(hydroxymethyl)phenyl]sulfonyl}(pentyl)amino]hexyl}-Nα-(methoxycarbonyl)-β-phenyl-L-phenylalaninamide

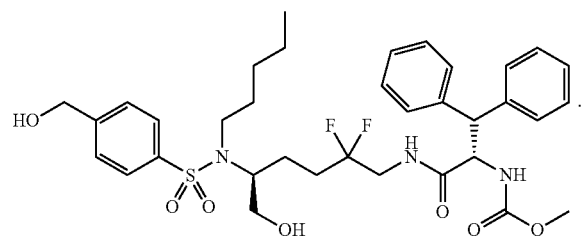 [SMILES: CCCCCN([C@H](CO)CCC(F)(F)CNC(=O)[C@@H](NC(=O)OC)C(c1ccccc1)c1ccccc1)S(=O)(=O)c1ccc(CO)cc1]

To a stirred solution of the material from Step 11 (51 mg, 0.056 mmol) in THF (1 mL) at 0° C. was added 1.0 M TBAF (111 µL, 0.11 mmol) in THF. The reaction mixture was stirred at room temperature overnight, concentrated to dryness in vacuo, and the residue was purified by flash chromatography on silica gel using EtOAc-hexanes to afford 30 mg of the title compound. ¹H NMR (DMSO-d₆): δ 8.37 (b, 1H), 7.76 (d, J=7.92 Hz, 2H), 7.49 (d, J=7.92 Hz, 2H), 7.46 (d, J=9.20 Hz, 1H), 7.37-7.30 (m, 4H), 7.30-7.18 (m, 4H), 7.17-7.09 (m, 2H), 5.41 (t, J=5.68 Hz, 1H), 5.10-5.00 (m, 1H), 4.74 (b, 1H), 4.59 (d, J=5.61 Hz, 2H), 4.27 (d, J=11.54 Hz, 1H), 3.63-3.51 (m, 1H), 3.42 (s, 3H), 3.39-3.15 (m, 2H), 3.27-3.20 (m, 2H), 3.12-2.90 (m, 2H), 1.65-1.06 (m, 10H), 0.84 (t, J=7.24 Hz, 3H).

Example 3

Preparation of methyl N²,N²-bis(tert-butoxycarbonyl)-5-fluoro-L-lysinate 4-methylbenzenesulfonate

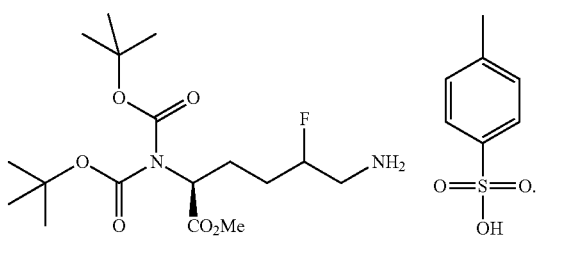 [SMILES: COC(=O)[C@H](CCC(F)CN)N(C(=O)OC(C)(C)C)C(=O)OC(C)(C)C ; Cc1ccc(S(=O)(=O)O)cc1]

Step 1: preparation of dimethyl(2S)-2-aminohexanedioate

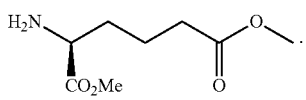

To a solution of L-2-aminoadipic acid (25 g, 155 mmol) in MeOH (500 mL) at 0° C. was added thionyl chloride (45.3 mL, 621 mmol) via an addition funnel over 30 minutes (internal temperature <12° C.). The reaction mixture was stirred at room temperature overnight, and concentrated to dryness in vacuo. Dichloromethane and saturated aqueous NaHCO₃ were added to the mixture. The reaction mixture was partitioned and extracted with dichloromethane (2×). The combined organics were washed with brine, dried over Na₂SO₄, filtered and concentrated in vacuo to afford 19.6 g of the title compound that was used without further purification.

Step 2: preparation of dimethyl(2S)-2-[bis(tert-butoxycarbonyl)amino]hexanedioate

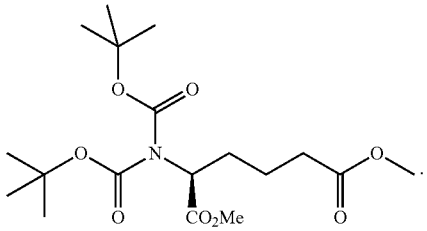 [SMILES: COC(=O)CCC[C@@H](C(=O)OC)N(C(=O)OC(C)(C)C)C(=O)OC(C)(C)C]

To a solution of the material from Step 1 (19.6 g, 104 mmol) in dichloromethane (200 mL) at room temperature was added di-tert-butyl dicarbonate (56.5 g, 259 mmol) and DMAP (1.27 g, 10.36 mmol). The reaction mixture was stirred at room temperature overnight, concentrated to dryness in vacuo, and the residue was purified by flash chromatography on silica gel using EtOAc-hexanes. The material was dissolved in acetonitrile (100 mL), di-tert-butyl dicarbonate (28 g, 128 mmol) and DMAP (0.5 g, 4.1 mmol) were added. The reaction mixture was stirred at room temperature overnight, concentrated to dryness in vacuo, and the residue was purified by flash chromatography on silica gel using EtOAc-hexanes to afford 8.34 g of the title compound. ¹H NMR (Acetone-d₆): δ 5.25-5.18 (b, 1H), 3.99 (s, 3H), 3.93 (s, 3H), 3.16-3.08 (m, 2H), 2.45-2.33 (m, 3H), 2.32-2.21 (m, 1H), 1.80 (s, 18H).

Step 3: preparation of methyl N,N-bis(tert-butoxycarbonyl)-6-oxo-L-norleucinate

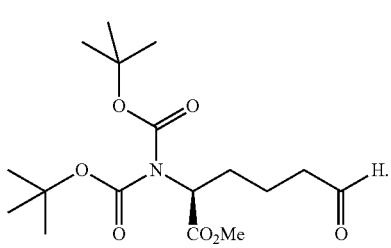

To a solution of the material from Step 2 (7.51 g, 19.08 mmol) in diethyl ether (95 mL) at −78° C. was slowly added 1.0 M Dibal-H (26.7 mL, 26.7 mmol) in hexanes. The reaction mixture was stirred at −70° C. for 90 minutes. Water (10 mL) was slowly added, and the reaction mixture was allowed to warm up to room temperature and aged for 30 minutes. Additional water (20 mL) was added, aged for 10 minutes with vigorous stirring. 8 g of celite was added to the reaction mixture, aged at room temperature for 5 minutes, filtered on a short pad of celite, rinsed with tert-butyl methyl ether (10×). The filtrate was washed with brine, dried over MgSO₄, filtered and concentrated in vacuo to afford 7.06 g of the title compound that was used without further purification.

Step 4: preparation of methyl N,N-bis(tert-butoxy-carbonyl)-5,5-difluoro-6-hydroxy-L-norleucinate and methyl N,N-bis(tert-butoxycarbonyl)-5-fluoro-6-hydroxy-L-norleucinate

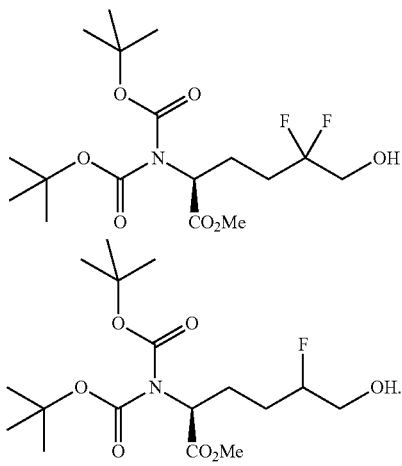

To a suspension of DL-proline (832 mg, 7.23 mmol) and N-fluorobenzenesulfonimide (11.45 g, 36.3 mmol) in 10% i-PrOH-THF (75 mL) at 0° C. was added a solution of the material from Step 3 (6.35 g, 16.43 mmol) in 10% i-PrOH-THF (15 mL). The reaction mixture was stirred at room temperature for 24 hours. The reaction mixture was cooled to −78° C. and ether (200 mL) was added. It was vigorously stirred, filtered through Davisil® silica, and eluted with ether. 30 mL of methyl sulfide was added. The reaction mixture was partitioned between ether and saturated aqueous NaHCO$_3$, extracted with ether (2×). The combined organics were washed with brine, dried over MgSO$_4$, filtered and concentrated in vacuo. The residue was dissolved in 40% ethanol-dichloromethane (100 mL), cooled at 0° C., and sodium borohydride (932 mg, 24.65 mmol) was added. The reaction mixture was stirred at room temperature for 90 minutes, poured into 1 N NaHCO$_3$, and extracted with dichloromethane. The combined organics were washed brine, dried over MgSO$_4$, filtered and concentrated in vacuo. The residue was purified by flash chromatography on silica gel using EtOAc-hexanes (15 to 50%) to afford 1.18 g of methyl N,N-bis(tert-butoxycarbonyl)-5,5-difluoro-6-hydroxy-L-norleucinate, and 2.32 g of methyl N,N-bis(tert-butoxycarbonyl)-5-fluoro-6-hydroxy-L-norleucinate. $^1$H NMR of methyl N,N-bis(tert-butoxycarbonyl)-5,5-difluoro-6-hydroxy-L-norleucinate: $^1$H NMR (CHCl$_3$-d): δ 4.22-3.99 (b, 1H), 3.82-3.68 (m, 2H), 3.73 (s, 3H), 2.42-2.29 (m, 1H), 2.14-1.89 (m, 3H), 1.48 (s, 18H). $^1$H NMR of methyl N,N-bis(tert-butoxycarbonyl)-5-fluoro-6-hydroxy-L-norleucinate: $^1$H NMR (CHCl$_3$-d): δ 4.91-4.84 (m, 1H), 4.73-4.50 (m, 1H), 3.81-3.61 (m, 2H), 3.72 (s, 3H), 2.39-2.17 (m, 2H), 2.00-1.68 (m, 2H), 1.49 (s, 18H).

Step 5: preparation of methyl N,N-bis(tert-butoxycarbonyl)-5-fluoro-6-[(methylsulfonyl)oxy]-L-norleucinate

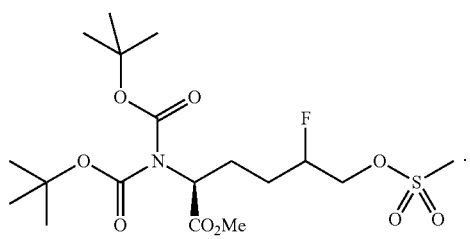 [SMILES: COC(=O)[C@H](CCC(F)COS(C)(=O)=O)N(C(=O)OC(C)(C)C)C(=O)OC(C)(C)C]

To a solution of the material from Step 4 (2.32 g, 5.55 mmol) in dichloromethane (20 mL) at 0° C. were added triethylamine (2.3 mL, 16.64 mmol) and methanesulfonyl chloride (865 µL, 11.10 mmol). The reaction mixture was stirred at room temperature for 70 minutes, poured into brine, and extracted with dichloromethane (2×). The combined organics were dried over MgSO$_4$, filtered and concentrated in vacuo. $^1$H NMR revealed presence of Et$_3$N.HCl. The residue was dissolved in EtOAc, water was added, and partitioned. The organic layer was washed with water, dried over MgSO$_4$, filtered and concentrated in vacuo to afford 2.822 g of the title compound that was used without further purification.

Step 6: preparation of methyl 6-azido-N,N-bis(tert-butoxycarbonyl)-5-fluoro-L-norleucinate

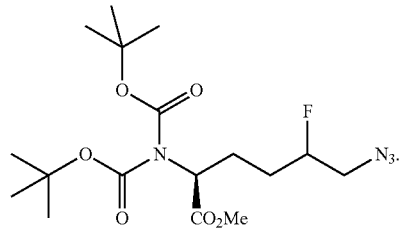 [SMILES: COC(=O)[C@H](CCC(F)CN=[N+]=[N-])N(C(=O)OC(C)(C)C)C(=O)OC(C)(C)C]

To a solution of the material from Step 1 (2.822 g, 5.57 mmol) in DMF (30 mL) at room temperature was added sodium azide (5.43 g, 84 mmol). The reaction mixture was stirred at 80° C. for 4 hours, poured into water, and extracted with tert-butylmethyl ether (2×). The combined organics were washed with water (2×) and brine, dried over MgSO$_4$, filtered and concentrated in vacuo to afford 2.38 g of the title compound that was used without further purification.

Step 7: preparation of methyl N$^2$,N$^2$-bis(tert-butoxycarbonyl)-5-fluoro-L-lysinate 4-methylbenzenesulfonate

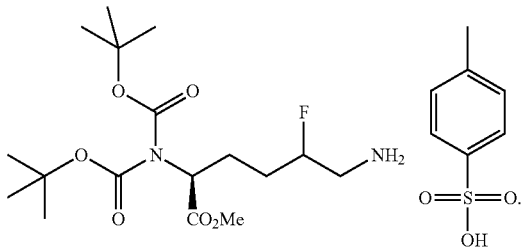

A solution of the material from Step 2 (2.2 g, 5.57 mmol), p-toluenesulfonic acid monohydrate (0.967 g, 5.09 mmol) in EtOAc (16 mL) and ethanol (16 mL) was purged with nitrogen, then 10% palladium on carbon (1.082 g, 1.017 mmol) was added. The reaction mixture was stirred under hydrogen (1 atm) for 5 hours, filtered through celite, rinsed with EtOAc, and the filtrate was concentrated in vacuo to afford 2.778 g of the title compound. $^1$H NMR (CDCl$_3$): δ 8.14-7.92 (b, 2H), 7.84-7.63 (b, 2H), 7.24-7.11 (b, 2H), 4.92-4.60 (b, 1H) 4.80-4.73 (m, 1H), 3.69 (s, 3H), 3.18-2.83 (b, 2H), 2.36 (s, 3H), 2.31-2.02 (b, 2H), 2.01-1.69 (b, 2H), 1.48 (s, 18H).

Example 4

Preparation of N-[(5S)-5-{(1,3-benzothiazol-6-ylsulfonyl)[(3,3-difluorocyclobutyl)methyl]amino}-2,2-difluoro-6-hydroxyhexyl]-Nα-(methoxycarbonyl)-β-phenyl-L-phenylalaninamide

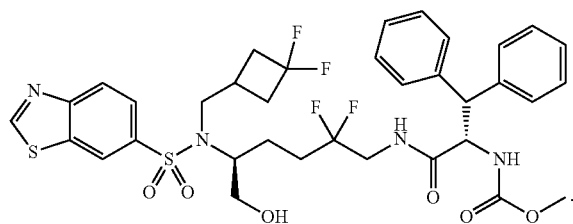 [SMILES: COC(=O)N[C@H](C(=O)NCC(F)(F)CC[C@@H](CO)N(CC1CC(F)(F)C1)S(=O)(=O)c1ccc2ncsc2c1)C(c1ccccc1)c1ccccc1]

Step 1: preparation of methyl N,N-bis(tert-butoxycarbonyl)-5,5-difluoro-6-{[(trifluoromethyl)sulfonyl]oxy}-L-norleucinate

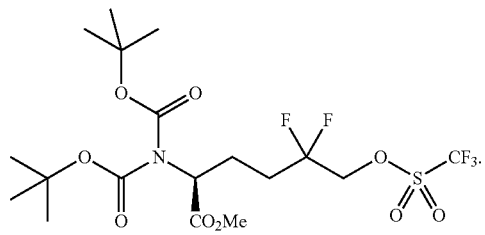 [SMILES: COC(=O)[C@H](CCC(F)(F)COS(=O)(=O)C(F)(F)F)N(C(=O)OC(C)(C)C)C(=O)OC(C)(C)C]

To a solution of methyl N,N-bis(tert-butoxycarbonyl)-5,5-difluoro-6-hydroxy-L-norleucinate from Example 3, Step 4 (1.18 g, 2.70 mmol) in dichloromethane (12 mL) at −40° C. were added N,N-diisopropylethylamine (940 μL, 5.39 mmol) and trifluoromethanesulfonic anhydride (546 μL, 3.23 mmol). The reaction mixture was stirred at room temperature for 90 minutes, poured into water, and extracted with tert-butylmethyl ether (2×). The combined organics were washed with brine, dried over MgSO$_4$, filtered and concentrated in vacuo to afford 1.49 g of the title compound that was used without further purification.

Step 2: preparation of methyl 6-azido-N,N-bis(tert-butoxycarbonyl)-5,5-difluoro-L-norleucinate

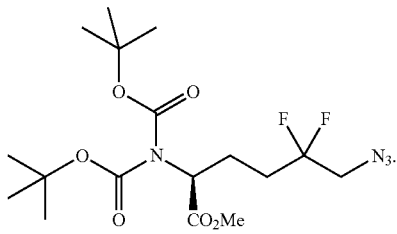 [SMILES: COC(=O)[C@H](CCC(F)(F)CN=[N+]=[N-])N(C(=O)OC(C)(C)C)C(=O)OC(C)(C)C]

To a solution of the material from Step 5 (1.49 g, 2.63 mmol) in DMF (15 mL) at room temperature was added sodium azide (1.71 g, 26.3 mmol). The reaction mixture was stirred at 50° C. for 3 hours, poured into water, and extracted with tert-butylmethyl ether (2×). The combined organics were washed with water and brine, dried over MgSO$_4$, filtered and concentrated in vacuo to afford 1.2 g of the title compound that was used without further purification.

Step 3: preparation of methyl N$^2$,N$^2$-bis(tert-butoxycarbonyl)-5,5-difluoro-L-lysinate

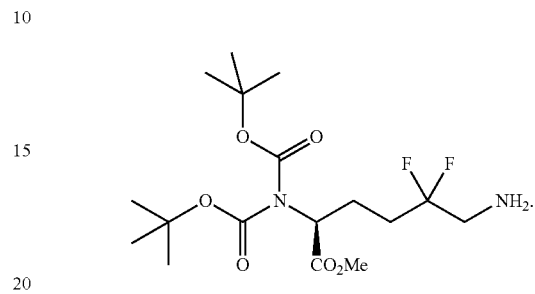

To a solution of the material from Step 6 (1.189 g, 2.45 mmol) in DMF (10 mL) at room temperature were added p-toluenesulfonic acid monohydrate (0.466 g, 2.451 mmol), ammonium chloride and zinc powder (0.321 g, 4.90 mmol). After 10 min, DMF (5 mL) was added, and the reaction mixture was stirred at room temperature for 2 hours. It was filtered on a pad of celite, rinsed with EtOAc and DMF (7 mL). The filtrate was poured into saturated aqueous NaHCO$_3$, and extracted with EtOAc (2×). The combined organics were washed with 10% LiCl (3×) and brine, dried over MgSO$_4$, filtered and concentrated in vacuo to afford 1.1 g of the title compound. $^1$H NMR (CDCl$_3$): δ 4.87 (dd, J=8.7, 5.6 Hz, 1H), 3.73 (s, 3H), 3.01-2.92 (m, 2H), 2.96 (s, 1H), 2.88 (s, 1H), 2.40-2.28 (m, 1H), 2.12-1.83 (m, 3H), 1.50 (s, 18).

Step 4: preparation of methyl N$^6$-[N-(methoxycarbonyl)-β-phenyl-L-phenylalanyl]-N$^2$,N$^2$-bis(tert-butoxycarbonyl)-5,5-difluoro-L-lysinate

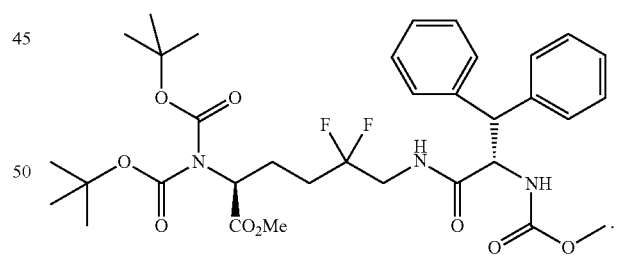

To a solution of the material from Step 7 (300 mg, 0.757 mmol) in DMF (7 mL) at 0° C. were added N-(methoxycarbonyl)-β-phenyl-L-phenylalanine (453 mg, 1.514 mmol), BOP (669 mg, 1.514 mmol) and triethylamine (0.422 mL, 3.03 mmol). The reaction mixture was stirred at room temperature overnight, poured into saturated aqueous NaHCO$_3$, and extracted with EtOAc (2×). The combined organics were washed with brine, dried over MgSO$_4$, filtered and concentrated in vacuo. The residue was purified by flash chromatography on silica gel using EtOAc-hexanes (0 to 100%) to afford 410 mg of the title compound as a colorless gum. LCMS (M+Na)=700.

Step 5: preparation of methyl $N^6$-[N-(methoxycarbonyl)-β-phenyl-L-phenylalanyl]-5,5-difluoro-L-lysinate

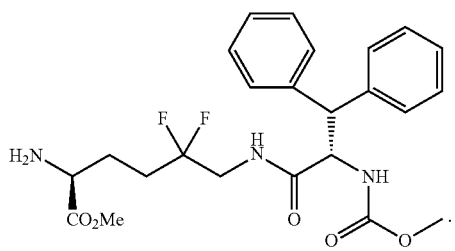 [SMILES: COC(=O)N[C@H](C(=O)NCC(F)(F)CC[C@H](N)C(=O)OC)C(c1ccccc1)c1ccccc1]

To a solution of the material from Step 8 (410 mg, 0.605 mmol) in dichloromethane (4 mL) at 0° C. were added anisole (198 μL, 1.815 mmol) and trifluoroacetic acid (560 μL, 7.26 mmol). The reaction mixture was stirred at room temperature for 3 hours, poured into saturated aqueous $NaHCO_3$, and extracted with dichloromethane (2×). The combined organics were dried over $MgSO_4$, filtered and concentrated in vacuo to afford 340 mg of the title compound as a colorless foam. LCMS (M+1)=478.

Step 6: preparation of methyl $N^6$-[N-(methoxycarbonyl)-β-phenyl-L-phenylalanyl]-$N^2$-(1,3-benzothiazol-6-ylsulfonyl)-5,5-difluoro-L-lysinate

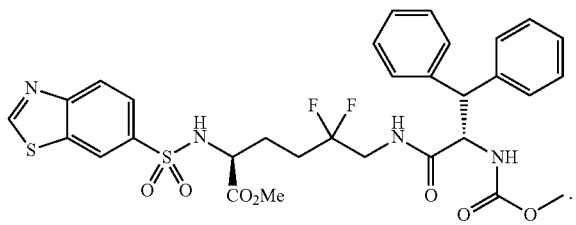 [SMILES: COC(=O)N[C@H](C(=O)NCC(F)(F)CC[C@H](NS(=O)(=O)c1ccc2ncsc2c1)C(=O)OC)C(c1ccccc1)c1ccccc1]

To a solution of the material from Step 9 (320 mg, 0.670 mmol) in pyridine (3 mL) were added 1,3-benzothiazole-6-sulfonyl chloride (235 mg, 1.0 mmol) and DMAP (16.4 mg, 0.134 mmol). The reaction mixture was stirred at 85° C. overnight, concentrated in vacuo, and the residue purified by flash chromatography on silica gel using EtOAc-hexanes (0 to 100%) to afford 178 mg of the title compound as a colorless foam. LCMS (M+1)=675.

Step 7: preparation of methyl $N^6$-[N-(methoxycarbonyl)-β-phenyl-L-phenylalanyl]-$N^2$-(1,3-benzothiazol-6-ylsulfonyl)-$N^2$-[(3,3-difluorocyclobutyl)methyl]-5,5-difluoro-L-lysinate

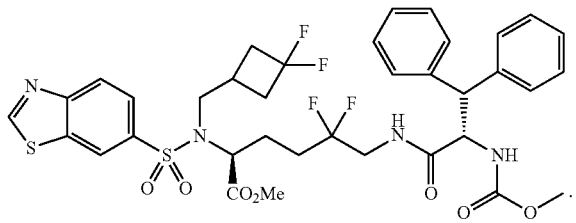 [SMILES: COC(=O)N[C@H](C(=O)NCC(F)(F)CC[C@@H](C(=O)OC)N(CC1CC(F)(F)C1)S(=O)(=O)c1ccc2ncsc2c1)C(c1ccccc1)c1ccccc1]

To a solution of the material from Step 10 (175 mg, 0.259 mmol), (3,3-difluorocyclobutyl)methanol (127 mg, 1.04 mmol) and triphenylphosphine (272 mg, 1.04 mmol) in THF (2 mL) at 0° C. was slowly added diisopropyl azodicarboxylate (202 uL, 1.04 mmol). The reaction mixture was stirred at room temperature overnight, concentrated in vacuo, and the residue purified by flash chromatography on silica gel using EtOAc-hexanes (0 to 90%) to afford 185 mg of the title compound as a colorless foam. LCMS (M+1)=779.

Step 8: preparation of $N^6$-[N-(methoxycarbonyl)-β-phenyl-L-phenylalanyl]-$N^2$-(1,3-benzothiazol-6-ylsulfonyl)-$N^2$-[(3,3-difluorocyclobutyl)methyl]-5,5-difluoro-L-lysine

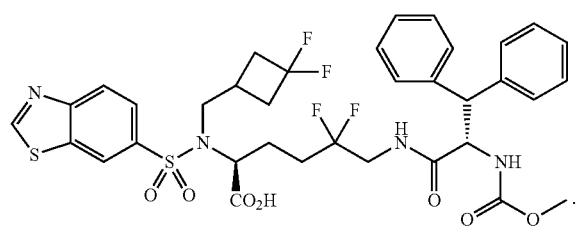 [SMILES: COC(=O)N[C@H](C(=O)NCC(F)(F)CC[C@@H](C(=O)O)N(CC1CC(F)(F)C1)S(=O)(=O)c1ccc2ncsc2c1)C(c1ccccc1)c1ccccc1]

To a solution of the material from Step 11 (85 mg, 0.109 mmol) in methanol (300 μL) and THF (600 μL) at 0° C. was added 1.0 N LiOH (125 μL, 0.125 mmol). The reaction mixture was stirred at room temperature for 3 hours, poured into sodium phosphate buffer pH=4, and extracted with EtOAc (2×). The combined organics were washed with brine, dried over $MgSO_4$, filtered and concentrated in vacuo, and the residue purified by flash chromatography on silica gel using MeOH—$CH_2Cl_2$ (0 to 10%) to afford 82 mg of the title compound as a colorless foam. LCMS (M+1)=765.

Step 9: preparation of N-[(5S)-5-{(1,3-benzothiazol-6-ylsulfonyl)[(3,3-difluorocyclobutyl)methyl]amino}-2,2-difluoro-6-hydroxyhexyl]-Nα-(methoxycarbonyl)-β-phenyl-L-phenylalaninamide

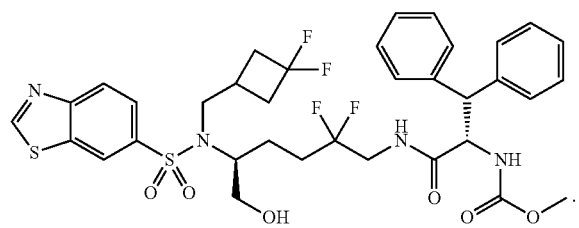 [SMILES: COC(=O)N[C@H](C(=O)NCC(F)(F)CC[C@@H](CO)N(CC1CC(F)(F)C1)S(=O)(=O)c1ccc2ncsc2c1)C(c1ccccc1)c1ccccc1]

To a solution of the material from Step 12 (82 mg, 0.107 mmol) in 1,2-dimethoxyethane (1.2 mL) at −15° C. were added N-methylmorpholine (12 μL, 0.113 mmol) and isobutyl chloroformate (15 μL, 0.113 mmol). The reaction mixture was stirred at −15° C. for 30 minutes. The solids were quickly filtered and washed with 1,2-dimethoxyethane (1 mL). The filtrate was cooled to −50° C., and a solution of sodium borohydride (5 mg, 0.129 mmol) in water (200 μL) was slowly added. After the addition of sodium borohydride, acetone (10 μL) was added followed by the addition of a saturated aqueous $NH_4Cl$ (10 mL). The reaction mixture was extracted with EtOAc (3×). The combined organics were washed with brine, dried over $MgSO_4$, filtered and concentrated in vacuo. The residue was purified by flash chromatography on silica gel using EtOAc-hexanes (0 to 100%) to afford 55 mg of the title compound as a colorless foam. LCMS (M+1)=751. $^1$H NMR (Acetone-$d_6$): δ 9.52 (s, 1H), 8.80-8.76 (m, 1H), 8.31-8.24 (m, 1H), 8.09-8.03 (m, 1H), 7.60-7.53 (m, 1H), 7.45-7.38 (m, 4H), 7.35-7.25 (m, 4H), 7.24-7.16 (m, 2H), 6.44 (d, J=8.74 Hz, 1H), 5.10-5.05 (m, 1H), 4.44 (d, J=10.97 Hz, 1H), 3.84-3.73 (m, 1H), 3.68-3.16 (m, 7H), 3.52 (s, 3H), 2.69-2.55 (m, 3H), 2.53-2.27 (m, 2H), 1.78-1.65 (m, 1H), 1.56-1.39 (m, 2H), 1.36-1.26 (m, 1H).

The following examples (Table 1) were prepared using similar procedures as described in the preparation of Example 4 with the appropriate building blocks of R¹OH.

bined organics were washed with brine, dried over MgSO$_4$, filtered and concentrated in vacuo. The residue was purified by reverse phase column using Zorbax Eclise Plus C$_{18}$ RRHT

TABLE 1

| Example No. | Name | LCMS M + 1 |
|---|---|---|
| 5 | N-{(5S)-5-[(1,3-benzothiazol-6-ylsulfonyl)(1H-pyrazol-4-ylmethyl)amino]-2,2-difluoro-6-hydroxyhexyl}-Nα-(methoxycarbonyl)-β-phenyl-L-phenylalaninamide | 727 |
| 6 | N-{(5S)-5-[(1,3-benzothiazol-6-ylsulfonyl)(4,4-difluorocyclohexyl)amino]-2,2-difluoro-6-hydroxyhexyl}-Nα-(methoxycarbonyl)-β-phenyl-L-phenylalaninamide | 765 |

Example 7

Preparation of N⁶-[N-(methoxycarbonyl)-β-phenyl-L-phenylalanyl]-N²-(1,3-benzothiazol-6-ylsulfonyl)-N²-[(3,3-difluorocyclobutyl)methyl]-5,5-difluoro-L-lysinamide

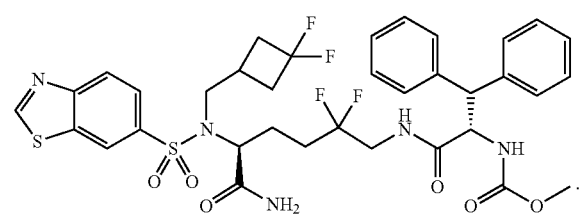 [SMILES: COC(=O)N[C@H](C(=O)NCC(F)(F)CC[C@@H](C(N)=O)N(CC1CC(F)(F)C1)S(=O)(=O)c1ccc2ncsc2c1)C(c1ccccc1)c1ccccc1]

Step 1: preparation of N⁶-[N-(methoxycarbonyl)-β-phenyl-L-phenylalanyl]-N²-(1,3-benzothiazol-6-ylsulfonyl)-N²-[(3,3-difluorocyclobutyl)methyl]-5,5-difluoro-L-lysinamide To a solution of the material from Example 4, Step 8 (98 mg, 0.128 mmol) in 1.2 mL of DMF at 0° C. were added 1-hydroxybenzotriazole (26 mg, 0.192 mmol), ammonium chloride (14 mg, 0.256 mmol), HATU (73 mg, 0.192 mmol) and N,N-diisopropylethylamine (67 µL, 0.358 mmol). The reaction mixture was stirred at 0° C. over the week-end. It was poured into water and extracted with EtOAc (2×). The com- 3×50 mm, 1.8 u column. Gradient: MeCN/H$_2$O+0.1% HCO$_2$H from 10:90 to 95:5 over 5 minutes. Flow: 1.0 mL/min. Positive ion mode. The title compound was obtained as a colorless foam. LCMS (M+1)=764. ¹H NMR (Acetone-d$_6$): δ 9.56 (s, 1H), 8.83 (d, J=12.07 Hz, 1H), 8.41-8.25 (m, 1H), 8.08 (d, J=8.22 Hz, 1H), 7.59 (s, 1H), 7.48-7.38 (m, 4H), 7.35-7.25 (m, 4H), 7.24-7.13 (m, 2H), 6.81 (s, 1H), 6.76-6.60 (m, 1H), 6.46 (d, J=8.74 Hz, 1H), 5.16-5.02 (m, 1H), 4.49-4.41 (m, 1H), 4.38-4.31 (m, 1H), 3.69-3.57 (m, 1H), 3.34 (s, 3H), 3.47-3.20 (m, 3H), 3.14-2.89 (m, 1H), 2.71-2.26 (m, 4H), 2.04-1.84 (m, 2H), 1.52-1.10 (m, 2H).

Example 8

Preparation of N-[(5S)-5-{[(4-aminophenyl)sulfonyl](propan-2-yl)amino}-3,3-difluoro-6-hydroxyhexyl]-Nα-(methoxycarbonyl)-β-phenyl-L-phenylalaninamide

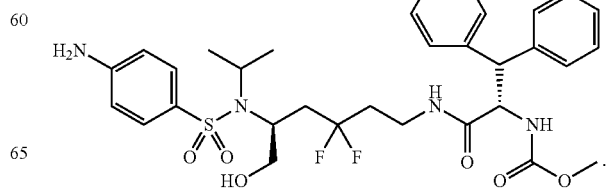

Step 1: preparation of diethyl N-(tert-butoxycarbonyl)-L-glutamate

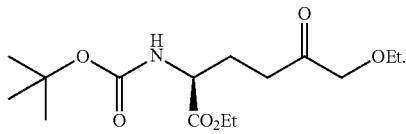 [SMILES: CCOCC(=O)CC[C@H](NC(=O)OC(C)(C)C)C(=O)OCC]

To a suspension of L-glutamic acid diethyl ester hydrochloride (15 g, 62.6 mmol) in acetonitrile (120 mL) were added triethylamine (17.44 mL, 125 mmol), di-tert-butyl dicarbonate (34.1 g, 156 mmol) and DMAP (0.765 g, 6.26 mmol). The reaction mixture was stirred at room temperature overnight, poured into water, and extracted with dichloromethane (2×). The combined organics were washed with brine, dried over MgSO$_4$, filtered and concentrated in vacuo to afford 18 g of the title compound that was used without further purification.

Step 2: preparation of diethyl N,N-bis(tert-butoxycarbonyl)-L-glutamate

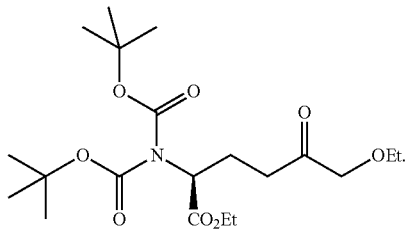 [SMILES: CCOCC(=O)CC[C@@H](C(=O)OCC)N(C(=O)OC(C)(C)C)C(=O)OC(C)(C)C]

To a solution of the material from Step 1 (18.082 g, 59.6 mmol) in acetonitrile (100 mL) were added DMAP (1.456 g, 11.92 mmol) and a solution of di-tert-butyl dicarbonate (19.5 g, 89 mmol) in acetonitrile (50 mL). The reaction mixture was stirred at room temperature for 2 days. It was concentrated to dryness, and the residue purified by flash chromatography on silica gel using EtOAc-hexanes (5 to 30%) to afford 9.93 g of the title compound as a colorless oil. $^1$H NMR (CDCl$_3$): δ 4.95-4.88 (m, 1H), 4.17 (q, J=7.01 Hz, 2H), 4.08 (q, J=7.01 Hz, 2H), 2.56-2.42. (m, 1H), 2.51-2.40 (m, 2H), 2.26-2.12 (m, 1H), 1.49 (s, 18H), 1.28 (t, J=7.01, 3H), 1.26 (t, J=7.01, 3H).

Step 3: preparation of ethyl N,N-bis(tert-butoxycarbonyl)-5-oxo-L-norvalinate

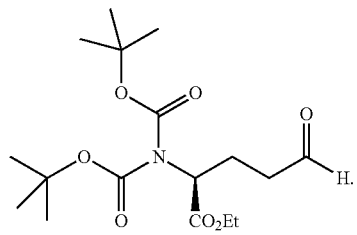

To a solution of the material from Step 2 (9.73 g, 24.12 mmol) in diethyl ether (240 mL) at −70° C. was slowly added 1.0 M Dibal-H (40.2 mL, 40.2 mmol) in toluene. The reaction mixture was stirred at −70° C. for 45 minutes. Water (10 mL) was slowly added, and the reaction mixture was allowed to warm up to room temperature and aged for 30 minutes. Additional water (80 mL) was added, and aged for 1 hour. It was filtered on a short pad of celite, rinsed with tert-butyl methyl ether (3×). The filtrate was washed with brine, dried over MgSO$_4$, filtered and concentrated in vacuo to afford 8.67 g of the title compound that was used without further purification.

Step 4: preparation of ethyl(2S,5E)-2-[bis(tert-butoxycarbonyl)amino]-4,4-difluoro-6-nitrohex-5-enoate and ethyl(2S,5E)-2-[bis(tert-butoxycarbonyl)amino]-4-fluoro-6-nitrohex-5-enoate

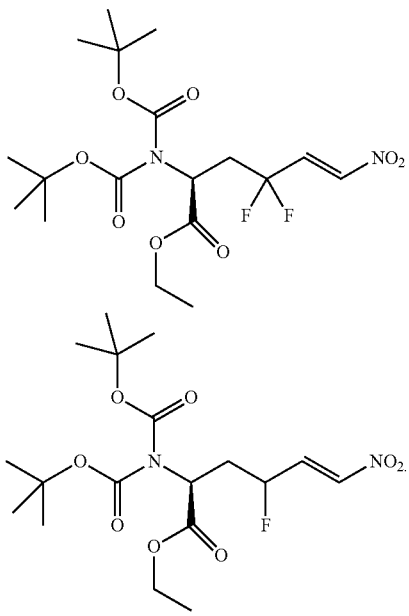

To a suspension of DL-proline (1.069 g, 9.28 mmol) and N-fluorobenzenesulfonimide (14.71 g, 46.6 mmol) in 10% i-PrOH-THF (45 mL) at 20° C. was added a solution of the material from Step 3 (8.38 g, 21.10 mmol) in 10% i-PrOH-THF (25 mL). The reaction mixture was stirred at room temperature for 24 hours. The reaction mixture was cooled to −78° C. and ether (140 mL) was added. It was vigorously stirred, filtered through Davisil silica, and eluted with ether. 30 mL of methyl sulfide was added. The reaction mixture was partitioned between ether and saturated aqueous NaHCO$_3$, extracted with ether (2×). The combined organics were washed with brine, dried over MgSO$_4$, filtered and concentrated in vacuo to afford 10.37 g of material. The residue (8.34 g, 21.10 mmol) was dissolved in toluene (84 mL), and cooled to 0° C. Nitromethane (11.38 mL, 211 mmol) and 1,1,3,3-tetramethylguanidine (0.265 mL, 2.11 mmol) were added. The reaction mixture was stirred at 0° C. overnight. The reaction mixture was cooled to 0° C., then methanesulfonyl chloride (3.29 mL, 42.2 mmol) and triethylamine (5.88 mL, 42.2 mmol) were added. It was allowed to stand at room temperature for 90 minutes. Additional methanesulfonyl chloride (1.644 mL, 21.10 mmol) and triethylamine (2.94 mL, 21.10 mmol) were added. It was stirred at room temperature for 90 minutes. The reaction mixture was poured into saturated aqueous NaHCO$_3$, and extracted with tert-butyl methyl ether (2×). The combined organics were washed with brine, dried over MgSO$_4$, filtered and concentrated in vacuo. The residue was purified by flash chromatography on silica gel using EtOAc-hexanes (0 to 50%) to afford 3.57 g of ethyl(2S,5E)-2-[bis(tert-butoxycarbonyl)amino]-4,4-difluoro-6-nitrohex-5-enoate. $^1$H NMR (Acetone-d$_6$): δ 7.61-7.50 (m, 1H), 7.40-7.32 (m, 1H), 5.28-5.23 (m, 1H), 4.15 (q, J=7.01 Hz, 2H), 3.08-2.95 (m, 1H), 2.90-2.78 (m, 1H), 1.49 (s, 18H), 1.23 (t, J=7.01, 3H).

Step 5: preparation of ethyl N,N-bis(tert-butoxycarbonyl)-4,4-difluoro-6-nitro-L-norleucinate

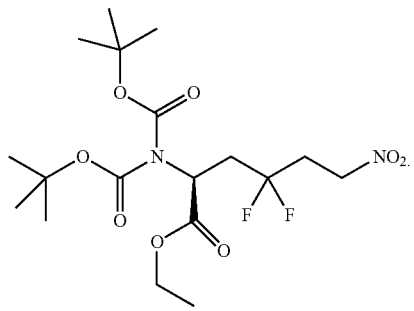 [SMILES: CCOC(=O)[C@H](CC(F)(F)CC[N+](=O)[O-])N(C(=O)OC(C)(C)C)C(=O)OC(C)(C)C]

To a solution of ethyl(2S,5E)-2-[bis(tert-butoxycarbonyl)amino]-4,4-difluoro-6-nitrohex-5-enoate, from Step 4 (2.81 g, 6.40 mmol) in THF (64 mL) at 6° C. was added sodium borohydride (1.212 g, 32.0 mmol) followed by a slow addition of water (12.8 mL). The reaction mixture was stirred at room temperature for 4 hours, poured into 10% KH$_2$PO$_4$, and extracted with EtOAc (2×). The combined organics were washed with brine, dried over MgSO$_4$, filtered and concentrated in vacuo to afford 2.725 g of the title compound (colorless oil) that was used without further purification.

Step 6: preparation of ethyl N$^2$,N$^2$-bis(tert-butoxycarbonyl)-4,4-difluoro-L-lysinate 4-methylbenzenesulfonate

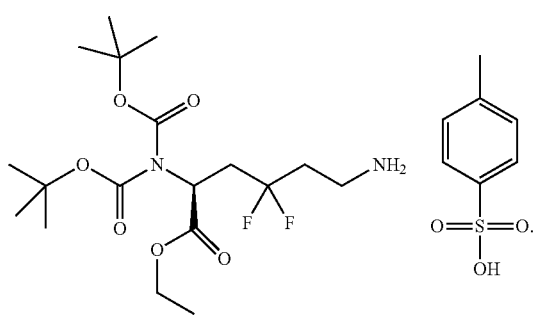 [SMILES: CCOC(=O)[C@H](CC(F)(F)CCN)N(C(=O)OC(C)(C)C)C(=O)OC(C)(C)C ; Cc1ccc(S(=O)(=O)O)cc1]

A solution of the material from Step 5 (2.725 g, 5.31 mmol), p-toluenesulfonic acid monohydrate (1.011 g, 5.31 mmol) in EtOAc (16 mL) and ethanol (16 mL) was purged with nitrogen, then 10% palladium on carbon (1.131 g, 1.063 mmol) was added. The reaction mixture was stirred under hydrogen (35 psi) for 20 hours, filtered through celite, rinsed with EtOH, and the filtrate was concentrated in vacuo to afford 2.18 g of the title compound as a grey semi-solid. $^1$H NMR (DMSO-d$_6$): δ 7.81-7.68 (b, 2H), 7.46 (d, J=7.76 Hz, 2H), 7.10 (d, J=7.76 Hz, 2H), 5.21-5.15 (m, 1H), 4.14-4.04 (m, 2H), 3.03-2.92 (b, 2H), 2.83-2.60 (m, 2H), 2.39-2.17 (m, 2H), 2.27 (s, 3H), 1.42 (s, 18H), 1.04 (t, J=7.01 Hz, 3H).

Step 7: preparation of ethyl N$^6$-[N-(methoxycarbonyl)-β-phenyl-L-phenylalanyl]-N$^2$,N$^2$-bis(tert-butoxycarbonyl)-4,4-difluoro-L-lysinate

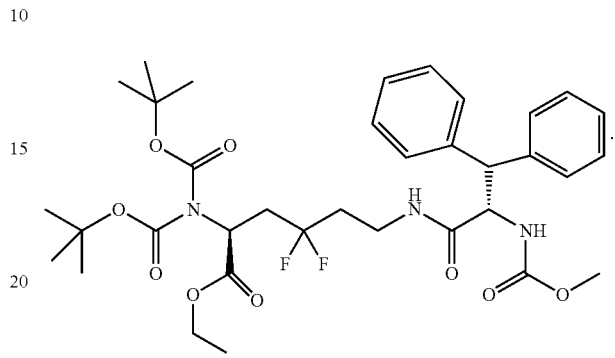

To a stirred solution of the material from the Step 6 (600 mg, 1.030 mmol) in THF (3.6 mL) and water (1.2 mL) at 0° C. were added sodium bicarbonate (433 mg, 5.15 mmol) and 2,5-dioxopyrrolidin-1-yl N-(methoxycarbonyl)-β-phenyl-L-phenylalaninate (490 mg, 1.236 mmol). The reaction mixture was stirred at room temperature overnight. It was poured into saturated aqueous NaHCO$_3$ and extracted with ethyl acetate (2×15 mL). The combined organic layers were washed with brine, dried with MgSO$_4$ and concentrated under vacuum. The residue was purified by flash chromatography on silica gel using EtOAc-hexanes (0 to 90%) to afford 434 mg of the title compound as a colorless foam. LCMS (M+Na)=714.

Step 8: preparation of ethyl N$^6$-[N-(methoxycarbonyl)-β-phenyl-L-phenylalanyl]-4,4-difluoro-L-lysinate

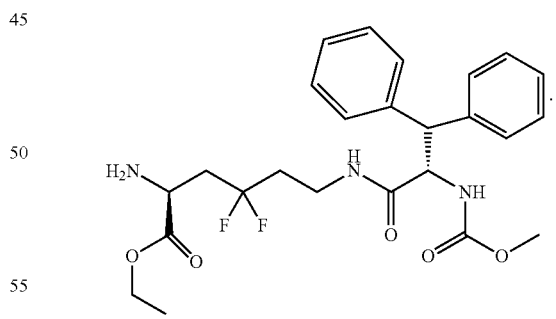

To a stirred solution of the material from Step 7 (290 mg, 0.419 mmol) in dichloromethane (1.8 mL) at 0° C. were added anisole (0.137 mL, 1.258 mmol) and TFA (0.388 mL, 5.03 mmol). The reaction mixture was stirred at room temperature for 2 hours, poured into saturated aqueous NaHCO$_3$, and extracted with dichloromethane (2×). The combined organic layers were dried over MgSO$_4$, filtered and concentrated in vacuo to afford 210 mg of the title compound as a colorless foam. LCMS (M+1)=492.

Step 9: preparation of ethyl $N^6$-[N-(methoxycarbonyl)-β-phenyl-L-phenylalanyl]-4,4-difluoro-$N^2$-[(4-nitrophenyl)sulfonyl]-L-lysinate

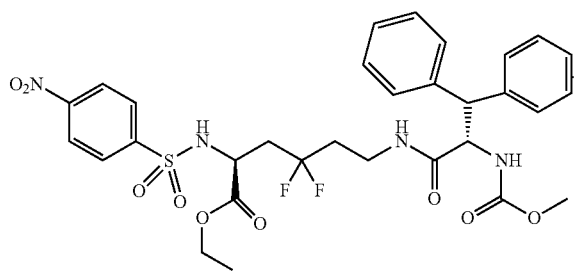 [SMILES: CCOC(=O)[C@H](CC(F)(F)CCNC(=O)[C@@H](NC(=O)OC)C(c1ccccc1)c1ccccc1)NS(=O)(=O)c1ccc([N+](=O)[O-])cc1]

To a solution of the material from Step 8 (210 mg, 0.427 mmol) in pyridine (2 mL) at room temperature were added 4-nitrobenzenesulfonyl chloride (142 mg, 0.641 mmol) and DMAP (10.44 mg, 0.085 mmol). The reaction mixture was stirred at 85° C. overnight, concentrated in vacuo, and the residue was purified by column chromatography on silica gel using ethyl acetate-hexanes (0:100 to 90:10) followed by 10% MeOH/DCM to afford 150 mg of the title compound as a yellow foam. LCMS (M+1)=677.

Step 10: preparation of ethyl $N^6$-[N-(methoxycarbonyl)-β-phenyl-L-phenylalanyl]-4,4-difluoro-$N^2$-[(4-nitrophenyl)sulfonyl]-$N^2$-propan-2-yl-L-lysinate

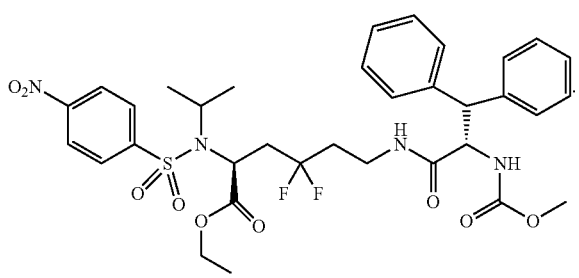 [SMILES: CCOC(=O)[C@H](CC(F)(F)CCNC(=O)[C@@H](NC(=O)OC)C(c1ccccc1)c1ccccc1)N(C(C)C)S(=O)(=O)c1ccc(N)cc1]

To a solution of the material from Step 9 (150 mg, 0.222 mmol), 2-propanol (0.034 mL, 0.443 mmol) and Ph$_3$P (116 mg, 0.443 mmol) in THF (1 mL) at 0° C. was slowly added diisopropyl azodicarboxylate (0.086 mL, 0.443 mmol). The reaction mixture was stirred at room temperature overnight. LCMS showed about 50% conversion, more 2-propanol (0.034 mL, 0.443 mmol), Ph$_3$P (116 mg, 0.443 mmol) and diisopropyl azodicarboxylate (0.086 mL, 0.443 mmol) were added, stirred for 8 hours, LCMS showed no progress. It was concentrated to dryness and the residue was purified by column chromatography on silica gel using ethyl acetate-hexanes (0:100 to 90:10) to afford 81 mg of the title compound as a colorless foam. LCMS (M+1)=719.

Step 11: preparation of ethyl $N^6$-[N-(methoxycarbonyl)-b-phenyl-L-phenylalanyl]-$N^2$-[(4-aminophenyl)sulfonyl]-4,4-difluoro-$N^2$-propan-2-yl-L-lysinate

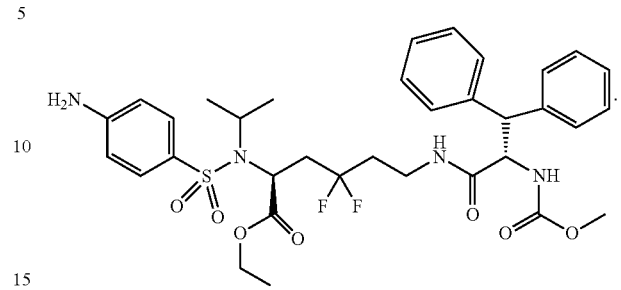

To the material from Step 10 (81 mg, 0.113 mmol) and 10% palladium on carbon (11.99 mg, 0.011 mmol) was added ethyl acetate (1.3 mL). The reaction mixture was purged with nitrogen, and stirred under hydrogen (1 atm) overnight. Upon addition of DCM, the reaction mixture was filtered through celite, washed with dichloromethane, and the filtrate was concentrated in vacuo. The residue was purified by column chromatography on silica gel using ethyl acetate-hexanes (0:100 to 90:10) to afford 50 mg of the title compound as a colorless foam. LCMS (M+1)=689.

Step 12: preparation of N-[(5S)-5-{[(4-aminophenyl)sulfonyl](propan-2-yl)amino}-3,3-difluoro-6-hydroxyhexyl]-Nα-(methoxycarbonyl)-β-phenyl-L-phenylalaninamide

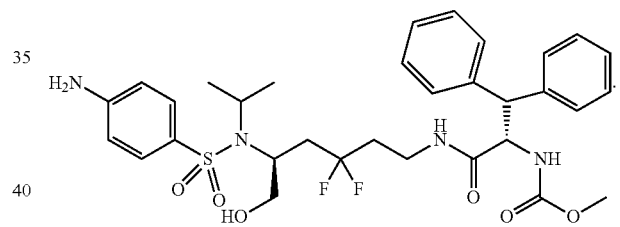

To a solution of the material from Step 11 (50 mg, 0.073 mmol) in THF (726 μL) at 0° C. were added a solution of 2 M lithium borohydride in THF (145 μL, 0.290 mmol) and methanol (11.75 μL, 0.290 mmol). The reaction mixture was stirred at room temperature for 2 hours. TLC showed not complete reaction. Additional 2 equiv of lithium borohydride was added, stirred at room temperature for 3 hours. The reaction mixture was poured into water and extracted with ethyl acetate (2×15 mL). The combined organic layers were washed with brine, dried with MgSO$_4$ and concentrated under vacuum. The residue was purified by column chromatography on silica gel using ethyl acetate-hexanes (0:100 to 100:0) to afford 26 mg of the title compound as a colorless foam. LCMS (M+1)=647. $^1$H NMR (Acetone-d$_6$): δ 7.62 (d, J=8.32 Hz, 2H), 7.46-7.36 (m, 4H), 7.34-7.25 (m, 4H), 7.23-7.15 (m, 3H), 6.76 (d, J=8.32 Hz, 2H), 6.40 (d, J=9.02 Hz, 1H), 5.49 (s, 2H), 4.97 (t, J=10.09 Hz, 1H), 4.42 (d, J=11.05 Hz, 1H), 3.93-3.81 (m, 2H), 3.80-3.69 (m, 2H), 3.66-3.59 (m, 1H), 3.50 (s, 3H), 3.34-3.14 (m, 1H), 3.12-2.95 (m, 1H), 2.46-2.29 (m, 2H), 1.81-1.44 (m, 2H), 1.20 (d, J=8.20 Hz, 6).

The following example (Table 2) was prepared using similar procedures as described in the preparation of Example 8 with the appropriate building blocks of R$^1$OH.

TABLE 2

| Example No. | Structure | LCMS M + 1 |
|---|---|---|
| 9 | N-[(5S)-5-{(1,3-benzothiazol-6-ylsulfonyl)[(3,3-difluorocyclobutyl)methyl]amino}-3,3-difluoro-6-hydroxyhexyl]-Nα-(methoxycarbonyl)-β-phenyl-L-phenylalaninamide 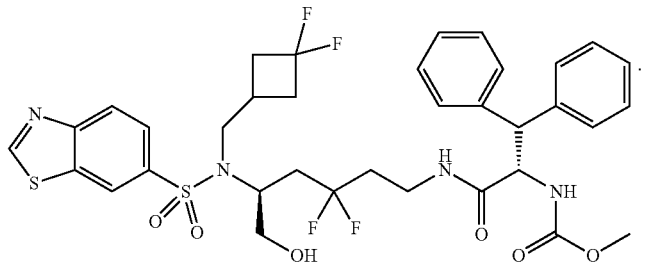 [SMILES: COC(=O)N[C@H](C(=O)NCCC(F)(F)C[C@@H](CO)N(CC1CC(F)(F)C1)S(=O)(=O)c1ccc2ncsc2c1)C(c1ccccc1)c1ccccc1] | 751 |

Example 10

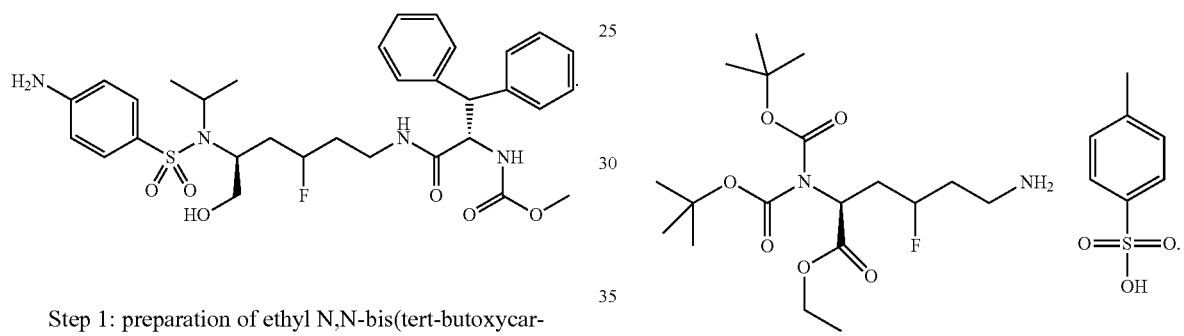

Step 1: preparation of ethyl N,N-bis(tert-butoxycarbonyl)-4-fluoro-6-nitro-L-norleucinate

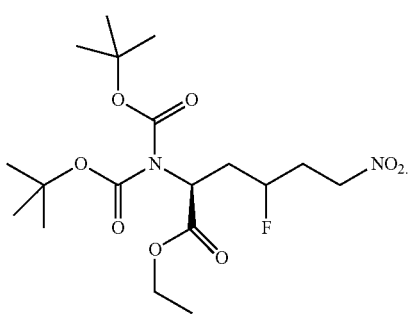 [SMILES: CCOC(=O)[C@H](CC(F)CC[N+](=O)[O-])N(C(=O)OC(C)(C)C)C(=O)OC(C)(C)C]

To a solution of ethyl(2S,5E)-2-[bis(tert-butoxycarbonyl)amino]-4-fluoro-6-nitrohex-5-enoate, from Example 8, Step 4 (2.38 g, 5.66 mmol) in THF (56.6 mL) at 6° C. was added sodium borohydride (1.071 g, 283 mmol) followed by a slow addition of water (11.32 mL). The reaction mixture was stirred at room temperature for 4 hours, poured into 10% KH$_2$PO$_4$, and extracted with EtOAc (2×). The combined organics were washed with brine, dried over MgSO$_4$, filtered and concentrated in vacuo to afford 2.391 g of the title compound (colorless oil) that was used without further purification.

Step 2: preparation of ethyl N$^2$,N$^2$-bis(tert-butoxycarbonyl)-4-fluoro-L-lysinate 4-methylbenzenesulfonate A solution of the material from Step 1 (2.421 g, 5.18 mmol), p-toluenesulfonic acid monohydrate (0.984 g, 5.18 mmol) in ethanol (25.9 mL) was purged with nitrogen, then 10% palladium on carbon (1.101 g, 1.035 mmol) was added. The reaction mixture was stirred under hydrogen (40 psi) for 22 hours, filtered through celite, rinsed with EtOH, and the filtrate was concentrated in vacuo to afford 2.031 g of the title compound as a grey solid. $^1$H NMR (CH$_3$OH-d$_4$): δ 7.70 (d, J=7.84 Hz, 2H), 7.23 (d, J=7.84 Hz, 2H), 5.11-5.04 (m, 1H), 4.92-4.55 (m, 1H), 4.21-4.15 (m, 2H), 3.30 (s, 3H), 3.13-3.04 (m, 2H), 2.58-2.42 (m, 2H), 2.36 (s, 3H), 2.29-1.90 (b, 2H), 1.50 (s, 18H), 1.17 (t, J=7.05 Hz, 3H).

Step 3: preparation of ethyl N$^6$-[N-(methoxycarbonyl)-β-phenyl-L-phenylalanyl]-N$^2$,N$^2$-bis(tert-butoxycarbonyl)-4-fluoro-L-lysinate

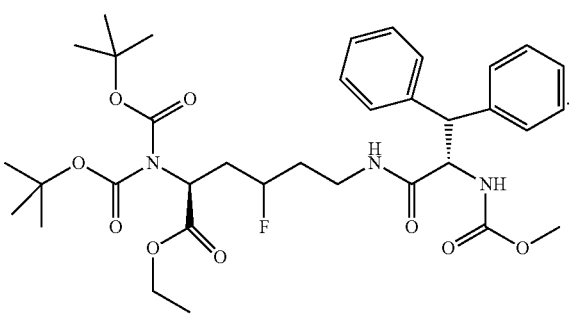 [SMILES: CCOC(=O)[C@H](CC(F)CCNC(=O)[C@@H](NC(=O)OC)C(c1ccccc1)c1ccccc1)N(C(=O)OC(C)(C)C)C(=O)OC(C)(C)C]

To a solution of the material from Step 2 (600 mg, 1.063 mmol) in THF (3.6 mL) and water (1.2 mL) at 0° C. were added sodium bicarbonate (446 mg, 5.31 mmol) and 2,5-dioxopyrrolidin-1-yl N-(methoxycarbonyl)-β-phenyl-L-phenylalaninate (505 mg, 1.275 mmol). The reaction mixture was stirred at room temperature overnight. It was poured into saturated aqueous NaHCO$_3$ and extracted with ethyl acetate (2×15 mL). The combined organic layers were washed with brine, dried over MgSO$_4$ and concentrated under vacuum. The residue was purified by column chromatography on silica gel using ethyl acetate-hexanes (0:100 to 80:20) to afford 490 mg of the title compound as a colorless foam. LCMS (M+Na)=696.

Step 4: preparation of ethyl N$^6$-[N-(methoxycarbonyl)-β-phenyl-L-phenylalanyl]-4-fluoro-L-lysinate

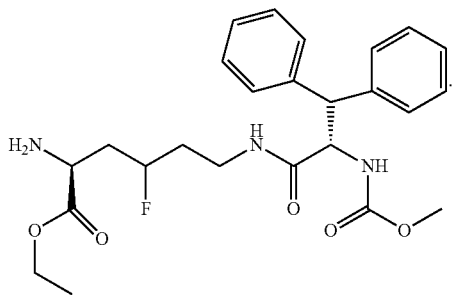 [SMILES: CCOC(=O)[C@@H](N)CC(F)CCNC(=O)[C@@H](NC(=O)OC)C(c1ccccc1)c1ccccc1]

To a solution of the material from Step 3 (476 mg, 0.706 mmol) in dichloromethane (3 mL) at 0° C. were added anisole (0.232 mL, 2.119 mmol) and TFA (0.653 mL, 8.48 mmol). The reaction mixture was stirred at room temperature for 3 hours, poured into saturated aqueous NaHCO$_3$, and extracted with dichloromethane (2×15 mL). The combined organic layers were dried over MgSO$_4$ and concentrated under vacuum to afford 370 mg of the title compound a colorless foam. LCMS (M+1)=474.

Step 5: preparation of ethyl N$^6$-[N-(methoxycarbonyl)-β-phenyl-L-phenylalanyl]-4-fluoro-N$^2$-[(4-nitrophenyl)sulfonyl]-L-lysinate

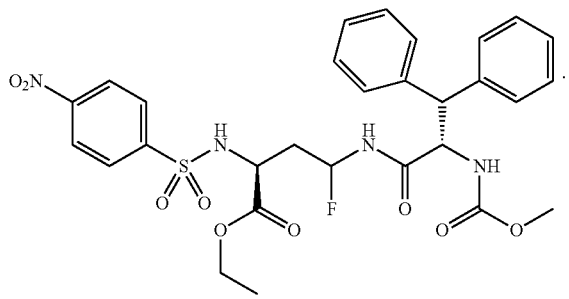 [SMILES: CCOC(=O)[C@H](CC(F)NC(=O)[C@@H](NC(=O)OC)C(c1ccccc1)c1ccccc1)NS(=O)(=O)c1ccc([N+](=O)[O-])cc1]

To a solution of the material from Step 4 (170 mg, 0.359 mmol) in pyridine (1.5 mL) at room temperature were added 4-nitrobenzenesulfonyl chloride (119 mg, 0.539 mmol) and DMAP (8.77 mg, 0.072 mmol). The reaction mixture was stirred at 85° C. overnight. Upon cooling to rt, the reaction mixture was concentrated in vacuo, and the residue was purified by column chromatography on silica gel using ethyl acetate-hexanes (0:100 to 90:10) to afford 50 mg of the title compound as a yellow foam. LCMS (M+1)=659.

Step 6: preparation of ethyl N$^6$-[N-(methoxycarbonyl)-β-phenyl-L-phenylalanyl]-4-fluoro-N$^2$-[(4-nitrophenyl)sulfonyl]-N$^2$-propan-2-yl-L-lysinate

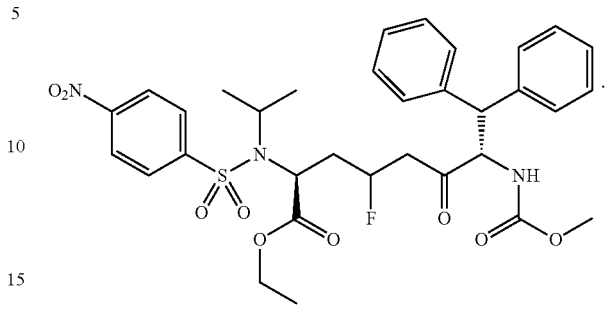

To a solution of the material from Step 5 (50 mg, 0.076 mmol), 2-propanol (0.023 mL, 0.304 mmol) and Ph$_3$P (80 mg, 0.304 mmol) in THF (1 mL) at 0° C. was slowly added diisopropyl azodicarboxylate (0.059 mL, 0.304 mmol). The reaction mixture was stirred at room temperature overnight. The reaction mixture was concentrated to dryness and the residue was purified by column chromatography on silica gel using ethyl acetate-hexanes (0:100 to 90:10) to afford 31 mg of the title compound as a colorless foam. LCMS (M+1)=701.

Step 7: preparation of ethyl N$^6$-[N-(methoxycarbonyl)-β-phenyl-L-phenylalanyl]-N$^2$-[(4-aminophenyl)sulfonyl]-4-fluoro-N$^2$-propan-2-yl-L-lysinate

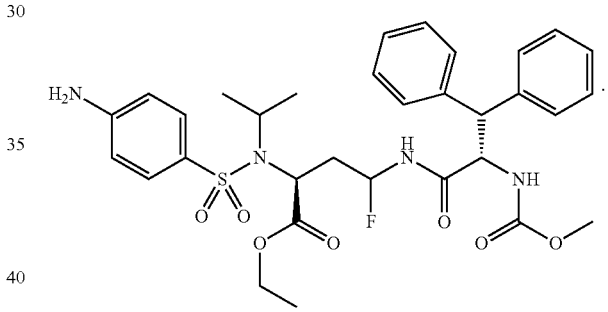

To the material from Step 6 (31 mg, 0.044 mmol) and 10% palladium on carbon (5 mg, 0.004 mmol) was added ethyl acetate (0.5 mL). The reaction mixture was purged with nitrogen, and stirred under hydrogen (1 atm) overnight. Upon addition of DCM, the reaction mixture was filtered through celite, washed with dichloromethane, and the filtrate was concentrated in vacuo. The residue was purified by column chromatography on silica gel using ethyl acetate-hexanes (0:100 to 90:10) to afford 23 mg of the title compound as a colorless foam. LCMS (M+1)=671.

Step 8: preparation of N-[(5S)-5-{[(4-aminophenyl)sulfonyl](propan-2-yl)amino}-3-fluoro-6-hydroxyhexyl]-Nα-(methoxycarbonyl)-β-phenyl-L-phenylalaninamide

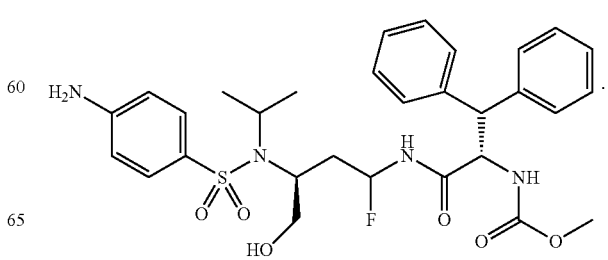

To a solution of the material from Step 7 (23 mg, 0.034 mmol) in THF (343 μL) at 0° C. were added a solution of 2 M lithium borohydride in THF (69 μL, 0.137 mmol) and methanol (6 μL, 0.137 mmol). The reaction mixture was stirred at room temperature for 2 hours. TLC showed not complete reaction. Additional 2 equiv of lithium borohydride was added, stirred at room temperature for 3 hours. The reaction mixture was poured into water and extracted with ethyl acetate (2×10 mL). The combined organic layers were washed with brine, dried with $MgSO_4$ and concentrated under vacuum. The residue was purified by column chromatography on silica gel using ethyl acetate-hexanes (0:100 to 100:0) to afford 18 mg of the title compound as a colorless foam. LCMS (M+1)=629. $^1$H NMR (Acetone-$d_6$): δ 7.60 (d, J=8.34 Hz, 1H), 7.53 (d, J=8.34 Hz, 1H), 7.46-7.36 (m, 4H), 7.33-7.24 (m, 4H), 7.23-7.15 (m, 2H), 7.16-7.08 (m, 1H), 6.77 (d, J=8.34 Hz, 2H), 6.38 (d, J=9.19 Hz, 1H), 5.52-5.44 (m, 1H), 4.97 (t, J=10.18 Hz, 1H), 4.49-4.38 (m, 1H), 4.35-4.12 (2×b, 1H), 3.94-3.83 (m, 2H), 3.81-3.67 (m, 2H), 3.50 (s, 3H), 3.42 (q, J=7.00 Hz, 1H), 3.29-3.03 (2×b, 1H), 2.98-2.88 (m, 1H), 2.17-2.05 (m, 1H), 1.88-1.71 (m, 1H), 1.45-1.24 (m, 2H), 1.20 (d, J=7.00 Hz, 3H), 1.10 (d, J=7.00 Hz, 3H).

Example 11

Assay for Inhibition of Microbial Expressed HIV Protease

The inhibition of WT HIV-1 protease was studied using the reaction of the protease (expressed in *Escherichia coli*) with a peptide substrate as described in WO 2009/042094. The test compound was first preincubated with the enzyme in assay buffer (50 mM sodium acetate, pH 5.5, 100 mM NaCl, and 0.1% BSA) for 30 minutes at room temperature. Substrate was then added to 400 micromolar in a total volume of 80 microliters containing 10 picomolar HIV-1 protease and the reaction was incubated for 1 hour at 30° C. The reaction was quenched with the addition of 120 microliters of 10% phosphoric acid. The product formation was determined after separation of product and substrate on a ZORBAX® Eclipse XDB-C18 (Agilent Technologies, Palo Alto, Calif.) column connected to an Agilent 1100 high performance liquid chromatography system with fluorescence detection (excitation 270 nanometer and emission 330 nanometer). Alternatively, the inhibitor was preincubated with enzyme and substrate as described above, but in a total volume of 20 microliters containing 20 picomolar HIV-1 protease and the reaction was incubated for 1 hour at 30° C. The reaction was quenched with the addition of 30 microliters of 1 micromolar indinavir (indinavir was also used as an internal standard), and the product formation was determined after separation of product and substrate on a ZORBAX® Eclipse XDB-C18 column connected to an API 4000 mass spectrometer (Applied Biosystems, Carlsbad, Calif.) with multiple reaction monitoring (transitions were 644.5/428.9 and 615.4/422.2 (M1/M3) for product and indinavir respectively). The extent of inhibition of the reaction was determined from the peak area of the products. HPLC of the products, independently synthesized, provided quantitation standards and confirmation of the product composition. Representative compounds of the present invention have exhibited inhibition of HIV-1 protease in this assay. For example, the compounds of Examples 1-2 and 4-10 were tested in the assay and exhibited the $IC_{50}$ values shown in Table 3 below.

Example 12

Assay for Inhibition of HIV Replication

Assays for the inhibition of acute HIV infection of T-lymphoid cells were conducted in accordance with Vacca, J. P. et al., *Proc. Natl. Acad. Sci. USA* 91: 4096-4100 (1994). Representative compounds of the present invention exhibit inhibition of HIV replication in this assay (also referred to herein as the "spread assay"). For example, as shown by their $IC_{95}$ values in Table 3 below, some of the compounds set forth in the foregoing Examples were tested in this assay and found to exhibit inhibition of HIV-1 replication.

Example 13

Cytotoxicity

Cytotoxicity was determined by microscopic examination of the cells in each well in the spread assay, wherein a trained analyst observed each culture for any of the following morphological changes as compared to control cultures: pH imbalance, cell abnormality, cytostatic changes, cytopathic changes or crystallization (i.e., the compound is not soluble or forms crystals in the well). None of the exemplified compounds that were tested in this assay were found to exhibit cytotoxicity, as described above.

TABLE 3

| | Data from assays | |
|---|---|---|
| Example | Enzyme inhibition$^a$ $IC_{50}$ (nM) | Spread$^b$ $IC_{95}$ (nM) |
| 1 | 0.03 | 10.7 |
| 1-1 | 0.24 | 42.8 |
| 1-2 | 0.01 | 19.5 |
| 2 | 0.019 | 16.3 |
| 4 | 0.59 | 181.3 |
| 5 | 0.39 | 906.6 |
| 6 | 2.73 | 355.6 |
| 7 | 0.43 | 200.5 |
| 8 | 6.07 | 299.3 |
| 9 | 5.62 | 105.0 |
| 10 | 3.90 | 245.5 |

$^a$Enzyme inhibition conducted in wild-type HIV-1 protease enzyme
$^b$Spread conducted in 10% FBS

What is claimed is:
1. A compound of Formula I:

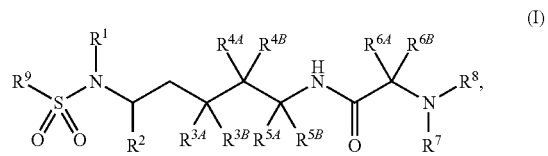

or a pharmaceutically acceptable salt thereof, wherein:
R$^1$ is C$_{1-6}$ alkyl, C$_{1-6}$ fluoroalkyl, CycA, AryA, C$_{1-6}$ alkyl substituted with CycA, HetA, C$_{1-6}$ alkyl substituted with HetA, or C$_{1-6}$ alkyl substituted with AryA;
R$^2$ is C(O)OH, C(O)NH$_2$, C(O)NH—C$_{1-6}$ alkyl, or CH(R$^J$)—Z, wherein:
  Z is OH, NH$_2$, or OR$^P$;
  R$^J$ is H, C$_{1-6}$ alkyl, C$_{1-6}$ fluoroalkyl, or C$_{1-6}$ alkyl substituted with C$_{3-5}$ cycloalkyl;

$R^P$ is PO(OH)O⁻.M⁺; PO(O⁻)₂.2M⁺; PO(O⁻)₂.M²⁺; or C(O)R$^Q$;

M⁺ is a pharmaceutically acceptable monovalent counterion;

M²⁺ is a pharmaceutically acceptable divalent counterion; and

R$^Q$ is:
(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl,
(5) O—$C_{1-6}$ alkyl substituted with O—$C_{1-6}$ alkyl,
(6) O—$C_{1-6}$ fluoroalkyl,
(7) C(O)O—$C_{1-6}$ alkyl,
(8) C(O)—$C_{1-6}$ alkylene-N(H)—$C_{1-6}$ alkyl,
(9) C(O)—$C_{1-6}$ alkylene-N(—$C_{1-6}$ alkyl)₂,
(10) $C_{1-6}$ alkyl substituted with C(O)O—$C_{1-6}$ alkyl,
(11) $C_{1-6}$ alkyl substituted with C(O)OH,
(12) $C_{1-6}$ alkyl substituted with C(O)—$C_{1-6}$ alkyl,
(13) N(H)—$C_{1-6}$ alkyl,
(14) N(—$C_{1-6}$ alkyl)₂,
(15) $C_{1-6}$ alkyl substituted with NH₂, N(H)—$C_{1-6}$ alkyl, or N(—$C_{1-6}$ alkyl)₂,
(16) AryA,
(17) $C_{1-6}$ alkyl substituted with AryA,
(18) O—$C_{1-6}$ alkyl substituted with AryA,
(19) HetA,
(20) $C_{1-6}$ alkyl substituted with HetA,
(21) O—$C_{1-6}$ alkyl substituted with HetA,
(22) HetB, or
(23) O-HetB;

$R^{3A}$ and $R^{3B}$ are each independently H, Cl, F, $C_{1-6}$ alkyl, $C_{1-6}$ fluoroalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl;

$R^{4A}$ and $R^{4B}$ are each independently H, Cl, F, $C_{1-6}$ alkyl, $C_{1-6}$ fluoroalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl;

$R^{5A}$ and $R^{5B}$ are each independently H, $C_{1-6}$ alkyl, $C_{1-6}$ fluoroalkyl, $C_{1-6}$ alkyl substituted with OH, $C_{2-6}$ alkenyl, $C_{2-6}$ alkynyl, $C_{3-6}$ cycloalkyl, or $C_{1-6}$ alkyl substituted with $C_{3-6}$ cycloalkyl, wherein the cycloalkyl is unsubstituted, or substituted with from 1 to 4 substituents each of which is independently Cl, F, or $C_{1-6}$ alkyl;

alternatively, $R^{5A}$ and $R^{5B}$ together with the carbon atom to which they are both attached form $C_{3-6}$ cycloalkyl;

and provided that at least one of $R^{3A}$, $R^{3B}$, $R^{4A}$, and $R^{4B}$ is F or Cl;

$R^{6A}$ is:

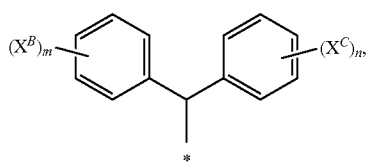

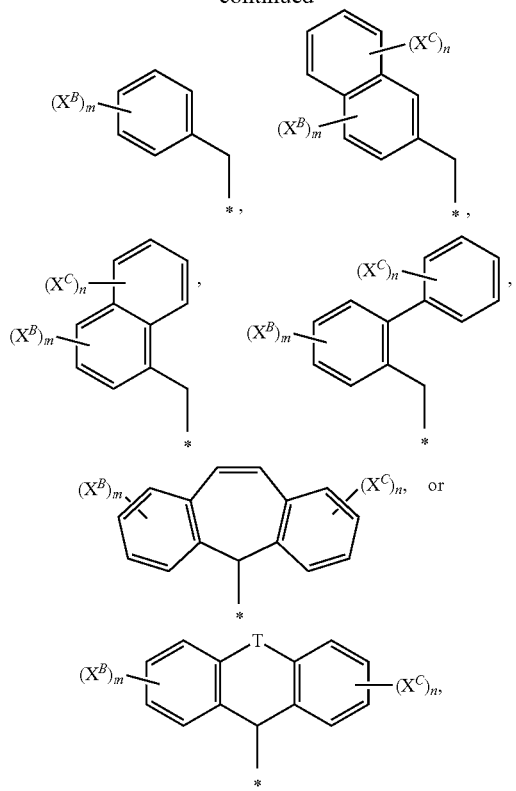

wherein the asterisk (*) denotes the point of attachment to the rest of the compound;

$R^{6B}$ is H or $C_{1-6}$ alkyl;

alternatively, $R^{6A}$ and $R^{6B}$ together with the carbon to which they are attached form a $C_{3-6}$ cycloalkyl which is unsubstituted, or substituted with phenyl, wherein the phenyl is unsubstituted, or substituted with from 1 to 3X$^B$;

each X$^B$ and each X$^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) NO₂,
(15) NH₂,
(16) N(H)—$C_{1-6}$ alkyl,
(17) N(—$C_{1-6}$ alkyl)₂,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) SO₂H,

(25) SO$_2$—C$_{1-6}$ alkyl; and
(26) C$_{1-6}$ alkyl substituted with:
 (a) C$_{1-6}$ haloalkyl,
 (b) OH
 (c) O—C$_{1-6}$ alkyl,
 (d) O—C$_{1-6}$ haloalkyl,
 (e) O—C$_{3-6}$ cycloalkyl,
 (f) SH,
 (g) S—C$_{1-6}$ alkyl,
 (h) halo,
 (i) CN,
 (j) NO$_2$,
 (k) NH$_2$,
 (l) N(H)—C$_{1-6}$ alkyl,
 (m) N(—C$_{1-6}$ alkyl)$_2$,
 (n) C(O)—C$_{1-6}$ alkyl,
 (o) C(O)OH,
 (p) C(O)O—C$_{1-6}$ alkyl, or
 (q) SO$_2$—C$_{1-6}$ alkyl;
T is O, S, S(O), or SO$_2$;
m is an integer equal to 0, 1, 2, or 3;
n is an integer equal to 0, 1, 2, or 3;
R$^7$ is H, C$_{1-6}$ alkyl, C$_{3-6}$ cycloalkyl, C$_{1-6}$ alkyl substituted with C$_{3-6}$ cycloalkyl, or C(O)—R$^K$;
R$^8$ is H or C$_{1-6}$ alkyl;
R$^K$ is:
 (1) C$_{1-6}$ alkyl,
 (2) C$_{3-6}$ cycloalkyl,
 (3) C$_{1-6}$ alkyl substituted with C$_{3-6}$ cycloalkyl,
 (4) O—C$_{1-6}$ alkyl,
 (5) O—C$_{1-6}$ alkyl substituted with O—C$_{1-6}$ alkyl,
 (6) O—C$_{1-6}$ fluoroalkyl,
 (7) C(O)O—C$_{1-6}$ alkyl,
 (8) C$_{1-6}$ alkyl substituted with C(O)O—C$_{1-6}$ alkyl,
 (9) C$_{1-6}$ alkyl substituted with C(O)OH,
 (10) C$_{1-6}$ alkyl substituted with C(O)—C$_{1-6}$ alkyl,
 (11) N(H)—C$_{1-6}$ alkyl,
 (12) N(—C$_{1-6}$ alkyl)$_2$,
 (13) C$_{1-6}$ alkyl substituted with NH$_2$, N(H)—C$_{1-6}$ alkyl, or N(—C$_{1-6}$ alkyl)$_2$,
 (14) AryA,
 (15) C$_{1-6}$ alkyl substituted with AryA,
 (16) O—C$_{1-6}$ alkyl substituted with AryA,
 (17) HetA,
 (18) C$_{1-6}$ alkyl substituted with HetA,
 (19) O—C$_{1-6}$ alkyl substituted with HetA,
 (20) HetB,
 (21) O-HetB, or
 (22) O—C$_{1-6}$ alkyl substituted with HetB;
R$^9$ is AryQ or HetQ;
AryQ is an aryl which is independently phenyl or naphthyl, wherein the phenyl or naphthyl is unsubstituted, or substituted with from 1 to 4X$^A$ each of which is independently:
 (1) C$_{1-6}$ alkyl,
 (2) C$_{3-6}$ cycloalkyl,
 (3) C$_{1-6}$ haloalkyl,
 (4) OH
 (5) O—C$_{1-6}$ alkyl,
 (6) O—C$_{1-6}$ haloalkyl,
 (7) O—C$_{3-6}$ cycloalkyl,
 (8) SH,
 (9) S—C$_{1-6}$ alkyl,
 (10) S—C$_{1-6}$ haloalkyl,
 (11) S—C$_{3-6}$ cycloalkyl,
 (12) halo,
 (13) CN,
 (14) NO$_2$,
 (15) NH$_2$,
 (16) N(H)—C$_{1-6}$ alkyl,
 (17) N(—C$_{1-6}$ alkyl)$_2$,
 (18) N(H)C(O)—C$_{1-6}$ alkyl,
 (19) N(H)CH(O),
 (20) CH(O),
 (21) C(O)—C$_{1-6}$ alkyl,
 (22) C(O)OH,
 (23) C(O)O—C$_{1-6}$ alkyl,
 (24) SO$_2$H,
 (25) SO$_2$—C$_{1-6}$ alkyl, or
 (26) C$_{1-6}$ alkyl substituted with:
  (a) C$_{3-6}$ cycloalkyl,
  (b) C$_{1-6}$ haloalkyl,
  (c) OH
  (d) O—C$_{1-6}$ alkyl,
  (e) O—C$_{1-6}$ haloalkyl,
  (f) O—C$_{3-6}$ cycloalkyl,
  (g) SH,
  (h) S—C$_{1-6}$ alkyl,
  (i) S—C$_{1-6}$ haloalkyl,
  (j) S—C$_{3-6}$ cycloalkyl,
  (k) halo,
  (l) CN,
  (m) NO$_2$,
  (n) NH$_2$,
  (o) N(H)—C$_{1-6}$ alkyl,
  (p) N(—C$_{1-6}$ alkyl)$_2$,
  (q) N(H)C(O)—C$_{1-6}$ alkyl,
  (r) N(H)CH(O),
  (s) CH(O),
  (t) C(O)—C$_{1-6}$ alkyl,
  (u) C(O)OH,
  (v) C(O)O—C$_{1-6}$ alkyl,
  (w) SO$_2$H, or
  (x) SO$_2$—C$_{1-6}$ alkyl;
HetQ is a heteroaryl which is independently (i) a 5- or 6-membered heteroaromatic ring containing from 1 to 4 heteroatoms independently selected from N, O and S, wherein each N is optionally in the form of an oxide or (ii) a 9- or 10-membered bicyclic, fused ring system containing from 1 to 4 heteroatoms independently selected from N, O and S, and wherein at least one of the rings is aromatic, each N in a ring is optionally in the form of an oxide, and each S is optionally S(O) or S(O)$_2$; and wherein the heteroaryl is unsubstituted, or substituted with from 1 to 4X$^A$ substituents each of which is independently as set forth in the definition of AryQ;
CycA is a C$_{3-7}$ cycloalkyl which is unsubstituted, or substituted with from 1 to 4 substituents each of which is independently Cl, F, or C$_{1-6}$ alkyl;
each AryA is an aryl which is independently phenyl or naphthyl, wherein the phenyl or naphthyl is unsubstituted, or substituted with from 1 to 4Y$^B$ wherein each Y$^B$ independently has the same definition as X$^B$;
each HetA is a heteroaryl which is independently (i) a 5- or 6-membered heteroaromatic ring containing from 1 to 4 heteroatoms independently selected from N, O and S, or (ii) is a fused, 9- or 10-membered heterobicyclic ring containing from 1 to 4 heteroatoms independently selected from N, O and S, and wherein at least one of the rings is aromatic, each N in a ring is optionally in the form of an oxide, and each S is optionally S(O) or S(O)$_2$; wherein the heteroaromatic ring (i) or the heterobicyclic ring (ii) is unsubstituted, or substituted with from 1 to 4 $Y^C$ wherein each $Y^C$ independently has the same definition as $X^B$;

each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is unsubstituted, or substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)NH$_2$, C(O)N(H)—$C_{1-6}$ alkyl, C(O)N(—$C_{1-6}$ alkyl)$_2$, C(O)H, C(O)—$C_{1-6}$ alkyl, CO$_2$H, CO$_2$—$C_{1-6}$ alkyl, SO$_2$H, or SO$_2$—$C_{1-6}$ alkyl.

2. A compound according to claim 1, or a pharmaceutically acceptable salt thereof, wherein $R^9$ is:

(i) AryQ, wherein AryQ is phenyl which is unsubstituted, or substituted with from 1 to 4$X^A$; or (ii) HetQ, wherein HetQ is a 9- or 10-membered bicyclic, fused ring system which is phenyl with a 5- or 6-membered, saturated or unsaturated heterocycle fused thereto, wherein the heterocycle contains from 1 to 2 heteroatoms independently selected from N, O and S, and wherein the fused ring system is unsubstituted, or substituted with from 1 to 4$X^A$.

3. A compound according to claim 2, or a pharmaceutically acceptable salt thereof, wherein $R^1$ is $C_{1-6}$ alkyl, $C_{1-6}$ fluoroalkyl, CycA, CH$_2$-CycA, CH$_2$-AryA or CH$_2$-HetA;

$R^2$ is C(O)OH, C(O)NH$_2$, CH$_2$—Z, CH(CH$_3$)—Z, CH(CF$_3$)—Z; wherein Z is OH, NH$_2$, or OR$^P$; and wherein R$^P$ is P(O)(OH)$_2$, P(O)(ONa)$_2$, P(O)(OK)$_2$, C(O)—$C_{1-6}$ alkyl, C(O)O—$C_{1-6}$ alkyl, C(O)N(—$C_{1-6}$ alkyl)$_2$, C(O)-pyridyl, or C(O)—$C_{1-6}$ alkylene-NH$_2$;

$R^{3A}$ is H, Cl, F, $C_{1-4}$ alkyl, $C_{1-4}$ fluoroalkyl, or CH$_2$—$C_{3-5}$ cycloalkyl, wherein the cycloalkyl is unsubstituted, or substituted with from 1 to 3 substituents each of which is independently F or $C_{1-6}$ alkyl;

$R^{3B}$ is H, F, or Cl;

$R^{4A}$ is H, Cl, F, $C_{1-4}$ alkyl, $C_{1-4}$ fluoroalkyl, or CH$_2$—$C_{3-5}$ cycloalkyl, wherein the cycloalkyl, is unsubstituted, or substituted with from 1 to 3 substituents each of which is independently F or $C_{1-6}$ alkyl;

$R^{4B}$ is H, F, or Cl;

and provided that at least one of $R^{3A}$, $R^{3B}$, $R^{4A}$, and $R^{4B}$ is F or Cl;

$R^{5A}$ is H, $C_{1-4}$ alkyl, $C_{1-4}$ fluoroalkyl, or CH$_2$—$C_{3-5}$ cycloalkyl, wherein the cycloalkyl, is unsubstituted, or substituted with from 1 to 3 substituents each of which is independently F or $C_{1-6}$ alkyl;

$R^{5B}$ is H;

$R^{6A}$ is:

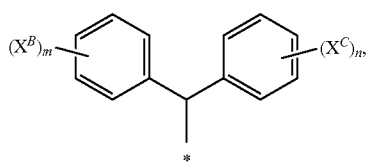

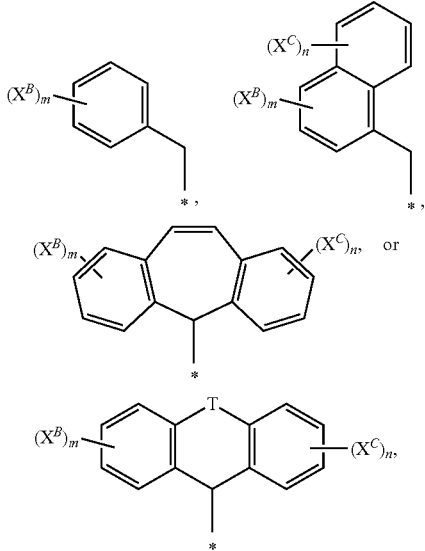

wherein the asterisk (*) denotes the point of attachment to the rest of the compound;

$R^{6B}$ is H or $C_{1-4}$ alkyl;

alternatively, $R^{6A}$ and $R^{6B}$ together with the carbon to which they are attached form a $C_{3-5}$ cycloalkyl which is unsubstituted, or substituted with phenyl, wherein the phenyl is unsubstituted, or substituted with from 1 to 2$X^B$;

each $X^B$ and each $X^C$ are independently selected from the group consisting of:

(1) $C_{1-3}$ alkyl,
(2) cyclopropyl,
(3) CF$_3$,
(4) OH,
(5) O—$C_{1-3}$ alkyl,
(6) OCF$_3$,
(7) Cl,
(8) Br,
(9) F,
(10) CN,
(11) NO$_2$,
(12) NH$_2$,
(13) N(H)—$C_{1-3}$ alkyl,
(14) N(—$C_{1-3}$ alkyl)$_2$,
(15) C(O)—$C_{1-3}$ alkyl,
(16) CO$_2$H,
(17) C(O)O—$C_{1-3}$ alkyl,
(18) CH$_2$OH, and
(19) CH$_2$O—$C_{1-3}$ alkyl;

m and n are each independently integers equal to 0, 1, or 2;

$R^7$ is H, $C_{1-6}$ alkyl, C(O)—$C_{1-6}$ alkyl, C(O)O—$C_{1-6}$ alkyl, C(O)N(—$C_{1-6}$ alkyl)$_2$, C(O)-HetA, C(O)OCH$_2$-HetA, C(O)-HetB, or C(O)OCH$_2$-HetB;

$R^8$ is H or $C_{1-4}$ alkyl;

$R^9$ is phenyl or benzothiazolyl, either of which is unsubstituted, or substituted with 1 or 2$X^A$, each of which is independently:

(1) $C_{1-3}$ alkyl,
(2) cyclopropyl,
(3) CF$_3$,
(4) OH,
(5) O—$C_{1-3}$ alkyl,
(6) OCF$_3$, (7) Cl,
(8) Br,
(9) F,
(10) CN,
(11) NO$_2$,
(12) NH$_2$,
(13) N(H)—C$_{1-3}$ alkyl,
(14) N(—C$_{1-3}$ alkyl)$_2$,
(15) C(O)—C$_{1-3}$ alkyl,
(16) CO$_2$H,
(17) C(O)O—C$_{1-3}$ alkyl, or
(18) C$_{1-3}$ alkyl substituted with
  (a) cyclopropyl,
  (b) CF$_3$,
  (c) OH,
  (d) O—C$_{1-3}$ alkyl,
  (e) OCF$_3$,
  (f) Cl,
  (g) Br,
  (h) F,
  (i) CN,
  (j) NO$_2$,
  (k) NH$_2$,
  (l) N(H)—C$_{1-3}$ alkyl,
  (m) N(—C$_{1-3}$ alkyl)$_2$,
  (n) C(O)—C$_{1-3}$ alkyl,
  (o) CO$_2$H, or
  (p) C(O)O—C$_{1-3}$ alkyl;

CycA is a C$_{3-6}$ cycloalkyl which is unsubstituted, or substituted with from 1 to 3 substituents each of which is independently F or C$_{1-4}$ alkyl;

each HetA is independently a heteroaryl selected from the group consisting of pyrrolyl, pyrazolyl, imidazolyl, triazolyl, tetrazolyl, pyridyl, pyrazinyl, quinolyl, isoquinolyl, and quinoxalinyl, wherein the heteroaryl is unsubstituted, or substituted with from 1 to 3 substituents each of which is independently CH$_3$, CF$_3$, OH, OCH$_3$, OCF$_3$, Cl, Br, F, CN, NH$_2$, N(H)CH$_3$, N(CH$_3$)$_2$, C(O)CH$_3$, CO$_2$CH$_3$, or SO$_2$CH$_3$; and HetB is a saturated heterocyclic ring selected from the group consisting of tetrahydrofuranyl, pyrrolidinyl, piperidinyl, piperazinyl, morpholinyl, or thiomorpholinyl in which the S is optionally oxidized to S(O) or S(O)$_2$, and wherein the ring is unsubstituted, or substituted with 1 or 2 substituents each of which is independently CH$_3$, CH$_2$CH$_3$, oxo, C(O)N(CH$_3$)$_2$, C(O)CH$_3$, CO$_2$CH$_3$, or S(O)$_2$CH$_3$.

4. The compound according to claim 3, or a pharmaceutically acceptable salt thereof, wherein:

$R^1$ is CH$_3$, CH$_2$CH$_3$, CH(CH$_3$)$_2$, CH$_2$CH$_2$CH$_3$, CH$_2$CH$_2$CH$_2$CH$_3$, CH$_2$CH(CH$_3$)$_2$, CH$_2$CH$_2$CH(CH$_3$)$_2$, CH$_2$CH$_2$CH$_2$F, CycA, CH$_2$-CycA, or CH$_2$-HetA;

$R^2$ is CH$_2$OH, C(O)NH$_2$, CH(CH$_3$)OH, CH$_2$NH$_2$, CH(CH$_3$)NH$_2$, CH$_2$OR$^P$, or CH(CH$_3$)—OR$^P$; wherein R$^P$ is P(O)(OH)$_2$, P(O)(ONa)$_2$, or C(O)CH$_3$;

$R^{3A}$ is H, F, Cl, or CH$_3$;
$R^{3B}$ is H, F, or Cl;
$R^{4A}$ is H, F, Cl, or CH$_3$;
$R^{4B}$ is H, F, or Cl;
and provided that at least one of $R^{3A}$, $R^{3B}$, $R^{4A}$ and $R^{4B}$ is F or Cl;
$R^{5A}$ and $R^{5B}$ are H;

$R^{6A}$ is:

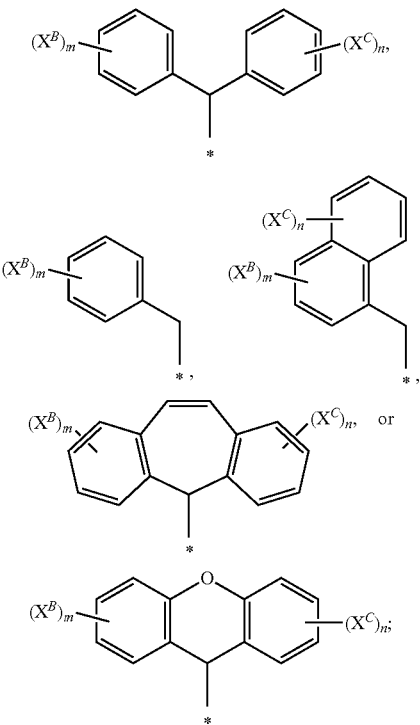

$R^{6B}$ is H;

each X$^B$ and each X$^C$ are independently selected from the group consisting of:
(1) CH$_3$,
(2) CH$_2$CH$_3$,
(3) CF$_3$,
(4) OH,
(5) OCH$_3$,
(6) OCF$_3$,
(7) Cl,
(8) Br,
(9) F,
(10) CN,
(11) NH$_2$,
(12) N(H)CH$_3$,
(13) N(CH$_3$)$_2$,
(14) C(O)CH$_3$,
(15) C(O)OCH$_3$,
(16) CH$_2$OH, and
(17) CH$_2$OCH$_3$;

$R^7$ is H, CH$_3$, C(O)CH$_3$, C(O)OCH$_3$, C(O)OC(CH$_3$)$_3$, C(O)N(CH$_3$)$_2$, C(O)-morpholinyl, C(O)-pyridyl, or C(O)O—CH$_2$-pyridyl;

$R^8$ is H or CH$_3$;

$R^9$ is phenyl or benzothiazolyl, wherein the benzothiazolyl is unsubstituted and the phenyl is unsubstituted, or substituted with 1 or 2X$^A$, each of which is independently:
(1) CH$_3$,
(2) CH$_2$CH$_3$,
(3) CF$_3$,
(4) OH,
(5) OCH$_3$,
(6) OCF$_3$,
(7) Cl, (8) Br,
(9) F,
(10) CN,
(11) $NH_2$,
(12) $N(H)CH_3$,
(13) $N(CH_3)_2$,
(14) $C(O)CH_3$,
(15) $C(O)OCH_3$,
(16) $CH_2OH$,
(17) $CH_2OCH_3$,
(18) $CH_2NH_2$,
(19) $CH_2N(H)CH_3$,
(20) $CH_2N(CH_3)_2$,
(21) $CH(CH_3)OH$,
(22) $CH(CH_3)OCH_3$,
(23) $CH(CH_3)NH_2$,
(24) $CH(CH_3)N(H)CH_3$, or
(25) $CH(CH_3)N(CH_3)_2$;

CycA is cyclopropyl or cyclobutyl, wherein the cyclopropyl or cyclobutyl is unsubstituted, or substituted with 1 or 2F; and HetA is a heteroaryl selected from the group consisting of pyrrolyl, pyrazolyl, imidazolyl, and pyridyl, wherein the heteroaryl is unsubstituted, or substituted with from 1 or 2 substituents each of which is independently $CH_3$, $CF_3$, OH, $OCH_3$, $OCF_3$, Cl, Br, F, or CN.

5. The compound according to claim 4, or a pharmaceutically acceptable salt thereof, wherein:

$R^1$ is $CH_3$, $CH_2CH_3$, $CH(CH_3)_2$, $CH_2CH_2CH_3$, $CH_2CH_2CH_2CH_3$, $CH_2CH(CH_3)_2$, $CH_2CH_2CH(CH_3)_2$, $CH_2CH_2CH_2F$, cyclobutyl, $CH_2$-cyclopropyl, $CH_2$-cyclobutyl in which the cyclobutyl is substituted with 1 or 2F, or $CH_2$-pyrazolyl in which the pyrazolyl is substituted with 1 or 2$CH_3$;

$R^2$ is $CH_2OH$, $C(O)NH_2$, $CH(CH_3)OH$, or $CH_2NH_2$;

$R^{3A}$ is H, F, or Cl;

$R^{3B}$ is H, F, or Cl;

$R^{4A}$ is H, F, or Cl;

$R^{4B}$ is H, F, or Cl;

and provided that at least one of $R^{3A}$, $R^{3B}$, $R^{4A}$ and $R^{4B}$ is F or Cl;

$R^{6A}$ is:

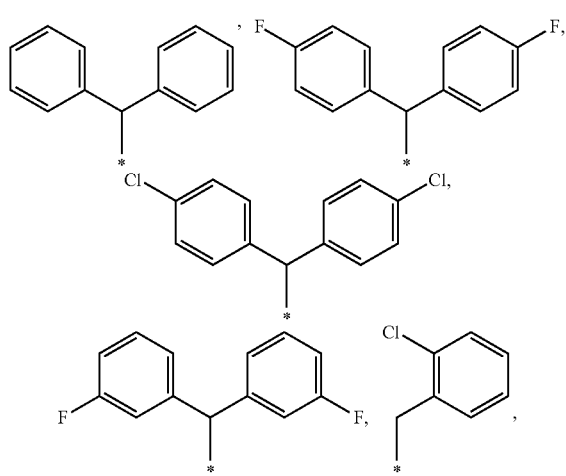

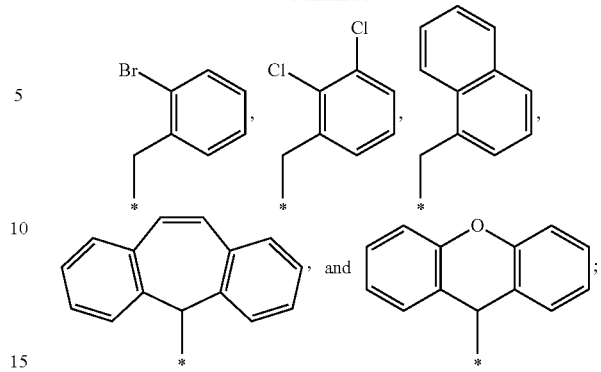

$R^7$ is H, $CH_3$, $C(O)OCH_3$, $C(O)OC(CH_3)_3$, or $C(O)O—CH_2$-pyridyl; and $R^9$ is:
(i) phenyl substituted with 1 or 2$X^A$, wherein one $X^A$ is in the para position on the phenyl ring and is $CH_3$, Cl, Br, F, $NH_2$, $C(O)CH_3$, $CH_2OH$, or $CH(CH_3)OH$; and the other, optional $X^A$ is in the meta position on the phenyl ring and is Cl, Br, or F; or

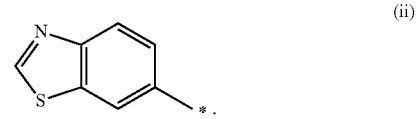

6. The compound according to claim 5, or a pharmaceutically acceptable salt thereof, wherein the definitions of $R^{3A}$, $R^{3B}$, $R^{4A}$ and $R^{4B}$ are selected from the group consisting of sets (a) to (d) as follows:
(a) $R^{3A}$ is F; $R^{3B}$ is H; $R^{4A}$ is H; and $R^{4B}$ is H;
(b) $R^{3A}$ is F; $R^{3B}$ is F; $R^{4A}$ is H; and $R^{4B}$ is H;
(c) $R^{3A}$ is H; $R^{3B}$ is H; $R^{4A}$ is F; and $R^{4B}$ is H; and
(d) $R^{3A}$ is H; $R^{3B}$ is H; $R^{4A}$ is F; and $R^{4B}$ is F.

7. The compound according to claim 5, or a pharmaceutically acceptable salt thereof, wherein the definitions of $R^{3A}$, $R^{3B}$, $R^{4A}$ and $R^{4B}$ are selected from the group consisting of sets (a) to (d) as follows:
(a) $R^{3A}$ is Cl; $R^{3B}$ is H; $R^{4A}$ is H; and $R^{4B}$ is H;
(b) $R^{3A}$ is Cl; $R^{3B}$ is Cl; $R^{4A}$ is H; and $R^{4B}$ is H;
(c) $R^{3A}$ is H; $R^{3B}$ is H; $R^{4A}$ is Cl; and $R^{4B}$ is H; and
(d) $R^{3A}$ is H; $R^{3B}$ is H; $R^{4A}$ is Cl; and $R^{4B}$ is Cl.

8. The compound according to claim 1, or a pharmaceutically acceptable salt thereof, wherein:
$R^2$ is $C(O)NH_2$ or $CH_2OH$;
$R^7$ is $C(O)OCH_3$ and
$R^8$ is H.

9. A compound according to claim 2, which is a compound of Formula II:

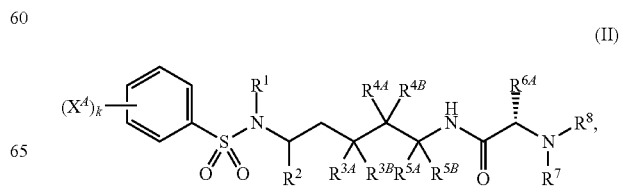

or a pharmaceutically acceptable salt thereof, wherein:
R$^1$ is C$_{1-6}$ alkyl, C$_{1-6}$ fluoroalkyl, C$_{3-6}$ cycloalkyl, or C$_{1-6}$ alkyl substituted with C$_{3-6}$ cycloalkyl;
R$^2$ is C(O)NH$_2$ or CH(R$^J$)—Z;
R$^{5A}$ is H, C$_{1-4}$ alkyl, C$_{1-4}$ fluoroalkyl, C$_{1-4}$ alkyl substituted with OH, C$_{2-4}$ alkenyl, C$_{2-4}$ alkynyl, C$_{3-5}$ cycloalkyl, or CH$_2$—C$_{3-5}$ cycloalkyl;
R$^{5B}$ is H or C$_{1-6}$ alkyl; and
alternatively, R$^{5A}$ and R$^{5B}$ together with the carbon atom to which they are both attached form C$_{3-5}$ cycloalkyl; and
k is an integer equal to 0, 1, or 2.

10. A compound according to claim 9, which is a compound of Formula III:

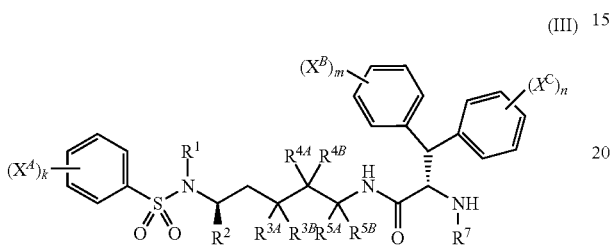

(III)

or a pharmaceutically acceptable salt thereof.

11. A compound according to claim 10 which is a compound of Formula IV:

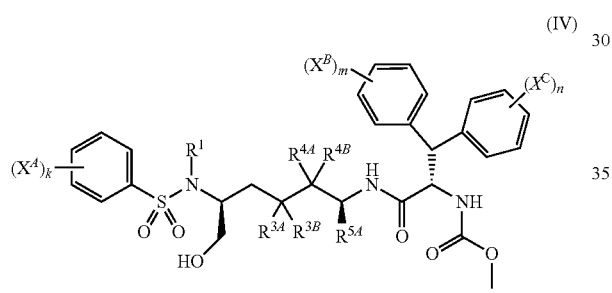

(IV)

or a pharmaceutically acceptable salt thereof.

12. The compound according to claim 10, which is a compound of Formula V:

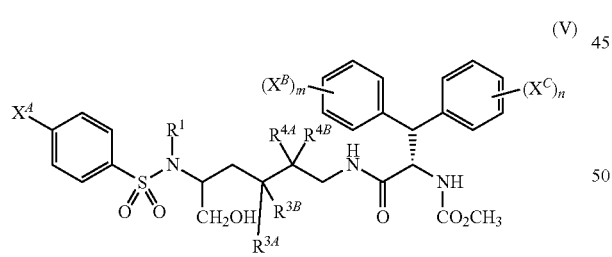

(V)

or a pharmaceutically acceptable salt thereof, wherein:
R$^1$ is CH$_3$, CH$_2$CH$_3$, CH(CH$_3$)$_2$, CH$_2$CH$_2$CH$_3$, CH$_2$CH$_2$CH$_2$CH$_3$, CH$_2$CH$_2$CH$_2$CH$_2$CH$_3$, CH$_2$CH(CH$_3$)$_2$, CH$_2$CH$_2$CH(CH$_3$)$_2$, CH$_2$CH$_2$CH$_2$F, cyclobutyl, cyclohexyl, CH$_2$-cyclopropyl, or CH$_2$-cyclobutyl substituted with 1 or 2F;
R$^{3A}$ is H, F, or Cl;
R$^{3B}$ is H, F, or Cl;
R$^{4A}$ is H, F, or Cl;
R$^{4B}$ is H, F, or Cl;
and provided that at least one of R$^{3A}$, R$^{3B}$, R$^{4A}$ and R$^{4B}$ is F or Cl;
X$^A$ is NH$_2$, C(O)CH$_3$, CH$_2$OH, or CH(CH$_3$)OH;

each X$^B$ and each X$^C$ are independently selected from the group consisting of:
(1) CH$_3$,
(2) CH$_2$CH$_3$,
(3) CF$_3$,
(4) OH,
(5) OCH$_3$,
(6) OCF$_3$,
(7) Cl,
(8) Br,
(9) F,
(10) CN,
(11) NH$_2$,
(12) N(H)CH$_3$,
(13) N(CH$_3$)$_2$,
(14) C(O)CH$_3$,
(15) C(O)OCH$_3$,
(16) CH$_2$OH, and
(17) CH$_2$OCH$_3$; and
m and n are each independently integers equal to 0, 1, or 2.

13. The compound according to claim 10, or a pharmaceutically acceptable salt thereof, wherein the definitions of R$^{3A}$, R$^{3B}$, R$^{4A}$ and R$^{4B}$ are selected from the group consisting of sets (a) to (d) as follows:
(a) R$^{3A}$ is F; R$^{3B}$ is H; R$^{4A}$ A is H; and R$^{4B}$ is H;
(b) R$^{3A}$ is F; R$^{3B}$ is Cl; R$^{4A}$ is H; and R$^{4B}$ is H;
(c) R$^{3A}$ is H; R$^{3B}$ is H; R$^{4A}$ is F; and R$^{4B}$ is H; and
(d) R$^{3A}$ is H; R$^{3B}$ is H; R$^{4A}$ is F; and R$^{4B}$ is F.

14. The compound according to claim 10, or a pharmaceutically acceptable salt thereof, wherein the definitions of R$^{3A}$, R$^{3B}$, R$^{4A}$ and R$^{4B}$ are selected from the group consisting of sets (a) to (d) as follows:
(a) R$^{3A}$ is Cl; R$^{3B}$ is H; R$^{4A}$ is H; and R$^{4B}$ is H;
(b) R$^{3A}$ is Cl; R$^{3B}$ is Cl; R$^{4A}$ is H; and R$^{4B}$ is H;
(c) R$^{3A}$ is H; R$^{3B}$ is H; R$^{4A}$ is Cl; and R$^{4B}$ is H; and
(d) R$^{3A}$ is H; R$^{3B}$ is H; R$^{4A}$ is Cl; and R$^{4B}$ is Cl.

15. The compound according to claim 12, or a pharmaceutically acceptable salt thereof, wherein
R$^1$ is CH(CH$_3$)$_2$, CH$_2$CH(CH$_3$)$_2$, CH$_2$CH$_2$CH(CH$_3$)$_2$, CH$_2$CH$_2$CH$_2$CH$_3$, or

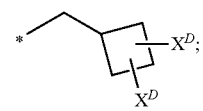

and
each X$^D$ is independently H or F.

16. The compound according to claim 12, or a pharmaceutically acceptable salt thereof, wherein m and n are either both 0 or both 1; and X$^B$ and X$^C$ are (i) both F and both para substituents, (ii) both F and both meta substituents, or (iii) both Cl and both para substituents.

17. A compound selected from the group consisting of:

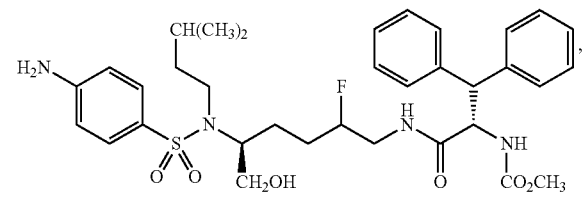

-continued

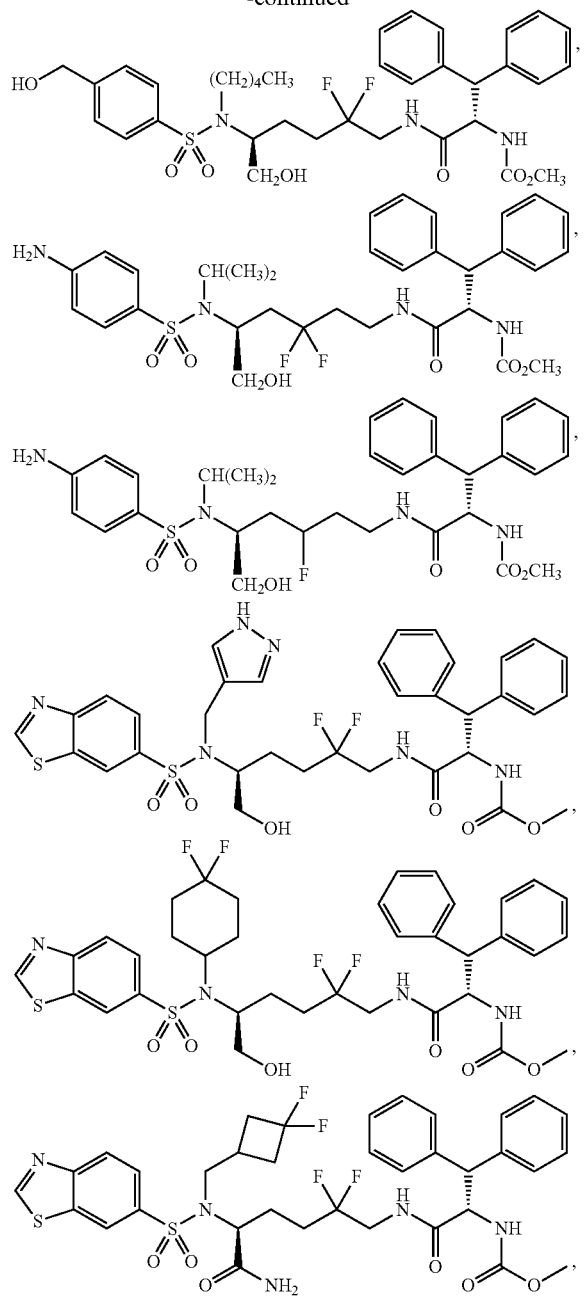

-continued

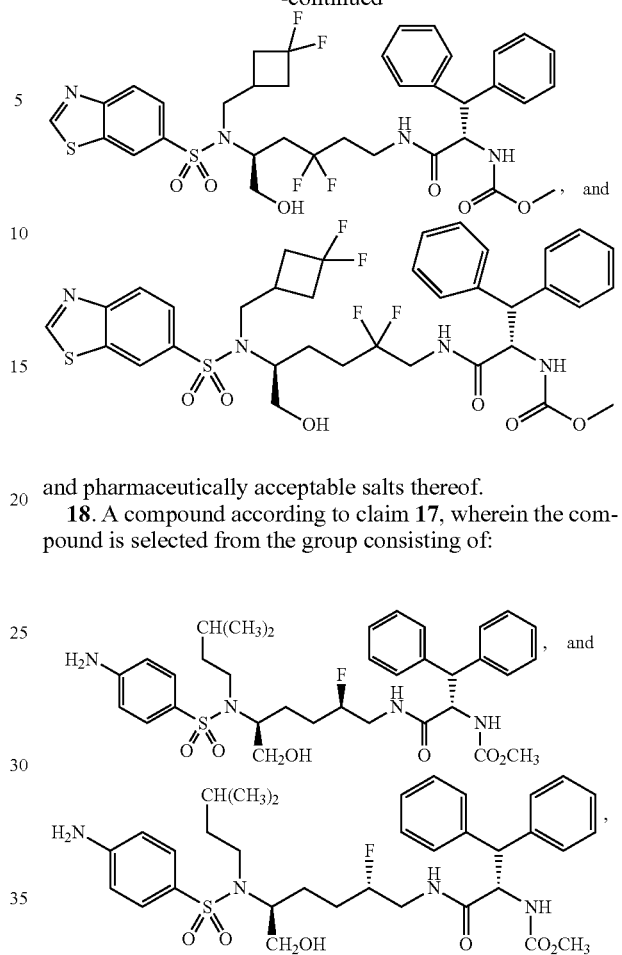

and pharmaceutically acceptable salts thereof.

18. A compound according to claim 17, wherein the compound is selected from the group consisting of:

and pharmaceutically acceptable salts thereof.

19. A pharmaceutical composition comprising an effective amount of a compound according to claim 1 or a pharmaceutically acceptable salt thereof, and a pharmaceutically acceptable carrier.

20. A method for the treatment or prophylaxis of infection by HIV or for the treatment, prophylaxis, or delay in the onset of AIDS in a subject in need thereof, which comprises administering to the subject an effective amount of a compound according to claim 1 or a pharmaceutically acceptable salt thereof.

\* \* \* \* \*